US012799494B2

(12) United States Patent
Armstrong et al.

(10) Patent No.: US 12,799,494 B2
(45) Date of Patent: Nov. 17, 2026

(54) METHODS AND COMPOSITIONS FOR GENOME EDITING VIA HAPLOID INDUCTION

(71) Applicant: Monsanto Technology LLC, St. Louis, MO (US)

(72) Inventors: Charles L. Armstrong, St. Charles, MO (US); Edward J. Cargill, Maryland Heights, MO (US); Fenggao Dong, Chesterfield, MO (US); Jonathan C. Lamb, Wildwood, MO (US); Huachun W. Larue, Chesterfield, MO (US); Richard J. Lawrence, Kirkwood, MO (US); Thomas S. Ream, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 539 days.

(21) Appl. No.: 17/748,857

(22) Filed: May 19, 2022

(65) Prior Publication Data

US 2022/0348943 A1 Nov. 3, 2022

Related U.S. Application Data

(63) Continuation of application No. 16/275,200, filed on Feb. 13, 2019, now Pat. No. 11,401,524, which is a continuation of application No. PCT/US2017/051248, filed on Sep. 13, 2017.

(60) Provisional application No. 62/394,409, filed on Sep. 14, 2016.

(51) Int. Cl.

| | |
|---|---|
| ***C12N 15/82*** | (2006.01) |
| ***A01H 1/08*** | (2006.01) |
| ***C12N 9/12*** | (2006.01) |
| ***C12N 9/22*** | (2006.01) |
| ***C12N 15/10*** | (2006.01) |
| *C07C 211/52* | (2006.01) |
| *C07C 233/61* | (2006.01) |
| *C07C 233/71* | (2006.01) |

(52) U.S. Cl.

CPC ........... *C12N 15/8213* (2013.01); *A01H 1/08* (2013.01); *C12N 9/1241* (2013.01); *C12N 9/22* (2013.01); *C12N 15/102* (2013.01); *C12N 15/8214* (2013.01); *C07C 211/52* (2013.01); *C07C 233/61* (2013.01); *C07C 233/71* (2013.01); *C07C 2603/30* (2017.05); *C12N 2310/20* (2017.05)

(58) Field of Classification Search

None

See application file for complete search history.

(56) References Cited

U.S. PATENT DOCUMENTS

| | | | | |
|---|---|---|---|---|
| 5,576,198 | A * | 11/1996 | McBride ............ | C12N 15/8214 800/298 |
| 7,078,234 | B2 | 7/2006 | Kriz et al. | |
| 7,244,876 | B1 | 7/2007 | Kuchuk et al. | |
| 8,558,061 | B2 | 10/2013 | Cui et al. | |
| 8,847,006 | B2 | 9/2014 | Jenkinson et al. | |
| 9,677,082 | B2 | 6/2017 | Chintamanani et al. | |
| 9,681,615 | B2 | 6/2017 | Bangera et al. | |
| 2005/0198711 | A1 | 9/2005 | Evans | |
| 2006/0128020 | A1 | 6/2006 | Calos | |
| 2007/0134796 | A1 | 6/2007 | Holmes et al. | |
| 2011/0203012 | A1 | 8/2011 | Dotson et al. | |
| 2014/0273235 | A1 | 9/2014 | Voytas et al. | |
| 2014/0283166 | A1 | 9/2014 | Chomet et al. | |
| 2014/0373445 | A1 | 12/2014 | Bangera et al. | |
| 2015/0082478 | A1 | 3/2015 | Cigan et al. | |
| 2015/0351340 | A1 | 12/2015 | Bundock et al. | |
| 2018/0245090 | A1 * | 8/2018 | Campbell ................ | A01H 1/08 |
| 2018/0273963 | A1 | 9/2018 | Kelliher et al. | |
| 2020/0332305 | A1 * | 10/2020 | Cigan ...................... | C12N 9/22 |

FOREIGN PATENT DOCUMENTS

| | | |
|---|---|---|
| WO | 2001011020 | 2/2001 |
| WO | 2011044132 | 4/2011 |
| WO | 2016044050 | 3/2016 |
| WO | 2017058022 | 4/2017 |
| WO | 2017058023 | 4/2017 |
| WO | 2018015956 | 1/2018 |
| WO | 2018015957 | 1/2018 |

OTHER PUBLICATIONS

Prigge et al. Production of Haploids and Doubled Haploids in Maize. Methods Mol. Biol. 2012:877:161-72 (Year: 2012).*
Chaikam et al. Doubled haploid technology for line development in maize: technical advances and prospects. Theor Appl Genet. Dec. 2019; 132(12):3227-3243. (Year: 2019).*
Isemer et al. Recombinant Whirly1 translocates from transplastomic chloroplasts to the nucleus. FEBS Lett. Jan. 2, 2012;586(1):85-8 . Epub Dec. 3, 2011. (Year: 2012).*
Nevarez et al. Mechanism of Dual Targeting of the Phytochrome Signaling Component HEMERA/pTAC12 to Plastids and the Nucleus. Plant Physiol. Apr. 2017; 173(4):1953-1966. Epub Feb. 23, 2017. (Year: 2017).*
Beurdeley et al., “Compact designer TALENs for efficient genome engineering,” Nature Communications 4:1762 (2013).
Birchler et al., “Plant minichromosomes”, Current Opinion in Biotechnology, 2016, 37:135-142.
Chaikam and Schipprack, “Development and validation of red root marker-based haploid inducers in maize,” Crop Science 56:1-11 (2016).
Chaikam et al. Development and Validation of Red Root Marker-Based Haploid Inducers in Maize. Crop Science. Jul.-Aug. 2016 . pp. 1678-1688. First published: Jul. 1, 2016.

(Continued)

*Primary Examiner* — Cynthia E Collins
(74) *Attorney, Agent, or Firm* — Dentons US LLP; William Holtz

(57) ABSTRACT

Methods and compositions for improved plant breeding using gene editing and haploid induction are provided.

15 Claims, No Drawings

Specification includes a Sequence Listing.

(56) References Cited

OTHER PUBLICATIONS

Chaudhari, "Use of Semigamy in the Production of Cotton Haploids," Bulletin of the Torrey Botanical Club 105:98-103 (1978).
Comeau et al., "Media for the in ovulo culture of proembryos of wheat and wheat-derived interspecific hybrids or haploids," Plant Science 81(1):117-125 (1992).
Dong et al., "Marker-assisted selection and evaluation of high oil in vivo haploid inducers in maize," Mol Breeding 34:1147-1158 (2014).
Dooner et al. Spontaneous mutations in maize pollen are frequent in some lines and arise mainly from retrotranspositions and deletions. Proc Natl Acad Sci U S A. May 28, 2019;116(22):10734-10743.
Evans, "The indeterminate gametophyte1 Gene of Maize Encodes a LOB Domain Protein Required for Embryo Sac and Leaf Development," Plant Cell 19(1): 46-62 (2007).
Extended European Search Report regarding Europe Application No. 17851407.1, mailed Feb. 4, 2020.
Gabsalilow et al., "Site- and strand-specific nicking of DNA by fusion proteins derived from MutH and I-SceI or TALE repeats," Nucleic Acids Research. 41: e83 (2013).
Gilles et al., "Loss of pollen—specific phospholipase Not Like Dad triggers gynogenesis in maize," EMBO J. 36(6): 707-717 (2017).
Kelliher et al., "MATRILINEAL, a sperm-specific phospholipase, triggers maize haploid induction," Nature 542:7639 (2017).
Koo et al., "Distinct DNA methylation patterns associated with active and inactive centromeres of the maize B chromosome," Genome Research 21(6):908-914 (2011).
Morgan, "Cyclin-dependent kinases: engines, clocks, and microprocessors," Annu Rev Cell Dev Biol 13:261-291 (1997).
PCT International Search Report for PCT/US2017/051248, dated Nov. 27, 2017.
PCT Written Opinion for PCT/US2017/051248, dated Nov. 27, 2017.
Ravi and Chan, "Haploid plants produced by centromere-mediated genome elimination," Nature 464:615-619 (2010).
Till et al. Discovery of induced point mutations in maize genes by Tilling. BMC Plant Biol. Jul. 28, 2004;4:12.
Wijnker and Schnittger, "Control of the meiotic cell division program in plants," Plant Reprod 26:143-158 (2013).
Yank et al., "TALE-PvuII Fusion Proteins—Novel Tools for Gene Targeting," PLoS One. 8: e82539 (2013).
Yonemaru et al., "A genomic region harboring the Pl1 allele from the Peruvian cultivar JC072A confers purple cob on Japanese flint corn (*Zea mays* L.)," Breed Sci. 68(5): 582-586 (2018).
Zhong et al., "Mutation of ZmDMP enhances haploid induction in maize," Nature Plants 5(6):575-580 (2019).

* cited by examiner

SEQUENCE LISTING

```
<160> NUMBER OF SEQ ID NOS: 151

<210> SEQ ID NO 1
<211> LENGTH: 750
<212> TYPE: DNA
<213> ORGANISM: Zea mays
<220> FEATURE:
<221> NAME/KEY: misc_feature
<222> LOCATION: (399)..(399)
```

<223> OTHER INFORMATION: n is a, c, g, or t
<220> FEATURE:
<221> NAME/KEY: misc_feature
<222> LOCATION: (597)..(599)
<223> OTHER INFORMATION: n is a, c, g, or t
<220> FEATURE:
<221> NAME/KEY: misc_feature
<222> LOCATION: (619)..(619)
<223> OTHER INFORMATION: n is a, c, g, or t
<220> FEATURE:
<221> NAME/KEY: misc_feature
<222> LOCATION: (630)..(631)
<223> OTHER INFORMATION: n is a, c, g, or t
<220> FEATURE:
<221> NAME/KEY: misc_feature
<222> LOCATION: (634)..(635)
<223> OTHER INFORMATION: n is a, c, g, or t
<220> FEATURE:
<221> NAME/KEY: misc_feature
<222> LOCATION: (637)..(639)
<223> OTHER INFORMATION: n is a, c, g, or t
<220> FEATURE:
<221> NAME/KEY: misc_feature
<222> LOCATION: (643)..(648)
<223> OTHER INFORMATION: n is a, c, g, or t
<220> FEATURE:
<221> NAME/KEY: misc_feature
<222> LOCATION: (655)..(660)
<223> OTHER INFORMATION: n is a, c, g, or t
<220> FEATURE:
<221> NAME/KEY: misc_feature
<222> LOCATION: (738)..(739)
<223> OTHER INFORMATION: n is a, c, g, or t

<400> SEQUENCE: 1
ctgcagcacc tgctggacgc cgttcaatcc ttcaccggcc tcaactggta tggtatggta 60
tgccttcggg ccttcgcgag gtttctgttt cggtttcgtt tcctgtgtga tgtaaattct 120
tgtattcctg ctccggtcat caacaggtgg gcgactattg cgctgacgac gttgatgatc 180
cggctggcga ctgtcccgct gctgatcaac cagatgaagt ccatgatgaa gttaaatgta 240
atgcgtctac tttaccacct tcttttgctg cctaatcctt tgtctttaag cgtgtttgtt 300
actggtccag gcattactgc atgagactat gggggtgccc aaacgcatag gagttgtcaa 360
atttgaacct aagcttttta aaattttcaa actcgaaant tgtgacactg ctaaagcata 420
aagatgctat ggtcaggatt tccccgccat tctaactgga cataggtctc ccatcatctg 480
gctctgcttg ggagtcgcta ctcactgctt cccctactaa tacactgagt ttggttaagc 540
gaaagattac aatctttatg tgcaacttct agtgatctgg atgctaaaaa tttatgnnnt 600
gcttggcaga gttcttagng cagttcccan nctnntnnna ctnnnnnnaa atctnnnnnn 660
ctgtacttta cagaaaatga ctctcagatg attatgtcaa ttgattatga tgattatgtc 720
aattgattat ctgaatgnnc tctgcaacat 750

<210> SEQ ID NO 2
<211> LENGTH: 746
<212> TYPE: DNA
<213> ORGANISM: Zea mays
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (326)..(326)
<223> OTHER INFORMATION: n is a, c, g, or t
<220> FEATURE:
<221> NAME/KEY: misc_feature
<222> LOCATION: (588)..(592)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (604)..(609)
<223> OTHER INFORMATION: n is a, c, g, or t
<220> FEATURE:
<221> NAME/KEY: misc_feature
<222> LOCATION: (626)..(633)
<223> OTHER INFORMATION: n is a, c, g, or t
<220> FEATURE:
<221> NAME/KEY: misc_feature
<222> LOCATION: (644)..(649)
<223> OTHER INFORMATION: n is a, c, g, or t
<220> FEATURE:
<221> NAME/KEY: misc_feature
<222> LOCATION: (652)..(661)
<223> OTHER INFORMATION: n is a, c, g, or t
<220> FEATURE:
<221> NAME/KEY: misc_feature
<222> LOCATION: (663)..(745)
<223> OTHER INFORMATION: n is a, c, g, or t

<400> SEQUENCE: 2
cgatcgtgat gaaaacttca gttggccttg tctacctgct tgcctgtctg ctatcacctt 60
tcatgccctc cttttctgat gaagtatggt cctagntgtc actgtatctt gtatgattta 120
attggactaa tgtttttcac ttgaatctca tgatgcgatc cttttgcaaa ggtattacgt 180
caattaaatt tatctccaga agaaaatttg tcattaagtg aagaaaaggg agaaattgca 240
aaggcaaaat ctccttggga ttttgtacca gcagggcaca gaatagggaa gcctgcacct 300
ctgttcaagg aattggtgcg tttttncttt tttataaata ttttcaccac ttgaccataa 360
ttttacatat cttcacttga tatatgaata cagaaagatg aagacgtagc tctccataga 420
gaaaaatatg cagggagtca agctgagaga agctcaaaag cagcagctga tgctgaagcc 480
aacaaagttg ctaatcagct caagggcaca aaattatccg gtattgatct ggacattctt 540
atttattctc cttatgctgg ttagggtgac aaacagaaaa atcttcgnnn nnangctatt 600
cttnnnnnna tcatgtattc atattnnnnn nnnctactat gacnnnnnng cnnnnnnnnn 660
ngnnnnnnnn nnnnnnnnnn nnnnnnnnnn nnnnnnnnnn nnnnnnnnnn nnnnnnnnnn 720
nnnnnnnnnn nnnnnnnnnn nnnnnt 746

<210> SEQ ID NO 3
<211> LENGTH: 585
<212> TYPE: DNA
<213> ORGANISM: Zea mays
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t
<220> FEATURE:
<221> NAME/KEY: misc_feature
<222> LOCATION: (302)..(302)
<223> OTHER INFORMATION: n is a, c, g, or t
<220> FEATURE:

<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (308)..(308)
<223> OTHER INFORMATION: n is a, c, g, or t
<220> FEATURE:
<221> NAME/KEY: misc_feature
<222> LOCATION: (310)..(310)
<223> OTHER INFORMATION: n is a, c, g, or t
<220> FEATURE:
<221> NAME/KEY: misc_feature
<222> LOCATION: (312)..(315)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t
<220> FEATURE:
<221> NAME/KEY: misc_feature
<222> LOCATION: (324)..(327)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t

<400> SEQUENCE: 3
atcaagatac ctagtggaat gcagaggtga gaatggttaa aaaacaatga tgtgtaaaga 60
tgtgantttt ttttnctttt catctgacaa gtgatcacca gaagctattg agaaaagtat 120
tggatacaag tnggctgccn ctgttatatg caccgccaga ttcgccaacc cacggagcag 180
accatggtcc atggcgctgt atggtgagct ggagacctct gaatatatca gaagtccggc 240
tcagatactg cgggctcaaa atcctgtttg gaacttgggg atcatcacct aatcaggatt 300
gnagntangn annnntgngt cncnnnnntgg atgcaaagac ataaaaacan aatttcctca 360
aggagtagag ccagcattat gtccagaaag ggctcaccag caccaagatt gtagatatga 420
tgggtcactg cattgagaac gtttggcccg gaggcctcga gaagctgagc aaaccacttt 480
tggtcataga atcctcctgg ggctacaacc agtggtttgc tggaatctcc gtatagctcg 540
ttgacgatgg tttgaagtac gactaggtct tttccatatt gctca 585

<210> SEQ ID NO 4
<211> LENGTH: 464
<212> TYPE: DNA
<213> ORGANISM: Zea mays
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t

<400> SEQUENCE: 4
gacctgaccc aactctgcca gcaagaagac agccaagaac aagaggcaca atctgcgcga 60
cgccatggcc aagtcgaagc cgaagccnaa gcnaggacct gcagcctgga gcccagcctg 120
ccatctacag agacctgcag cacgccggcg acgatcagga agagctcctc agacaaccgg 180
ctgcaaggga agcggccgcc caggctgctg atcagctcaa acaacatagc gccgctgccg 240
cccaccacgc acagcaacgc cgggccatcg cccggcggga aggacgacgt ggacccggac 300

```
tcggccatga tgggcgagtg cctcgacttc tgcaagcgaa acctgttcgc ggaggacggg    360

tacgaggacc gctacctgga tgacctcgcg gagctgccgg aggcgctgat cctgaaccgc    420

atcaactcca agcgggccat gcactcgtac cagctcggga agca                     464
```

```
<210> SEQ ID NO 5
<211> LENGTH: 628
<212> TYPE: DNA
<213> ORGANISM: Zea mays
<220> FEATURE:
<221> NAME/KEY: misc_feature
<222> LOCATION: (149)..(172)
<223> OTHER INFORMATION: n is a, c, g, or t
<220> FEATURE:
<221> NAME/KEY: misc_feature
<222> LOCATION: (369)..(410)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (605)..(606)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (613)..(613)
<223> OTHER INFORMATION: n is a, c, g, or t

<400> SEQUENCE: 5

tgggaagaaa ccagcacgca tccgtcgctg tcaggagctg atcagatcgg ctgctggagt     60

taagacggac ggacggcgta ttatggacgg ggaagattcc tgatgagatg gcgacaccaa    120

aactgaaagc cacgggcctg gatcctctnn nnnnnnnnnn nnnnnnnnnn nngattttct    180

cccggatttt catattacta ttctctacta gggatggatg gtgtatgtac acaccgatac    240

aatcaaggac cgtatcagca ggttgaataa taacaacgat aataatctac tgacacgcgc    300

aagtattttg gggctaatca tcggggtgga tgctgcatgc cgacgaggag atcgaggggg    360

aatcggacnn nnnnnnnnnn nnnnnnnnnn nnnnnnnnnn nnnnnnnnnn aagtcccaca    420

gctcgtcntg ctcctcctnc tcgggcatct gccactgctc ttgagaaatc tcgccggact    480

ccagtagctc caccacctgc ncattggtgg ccatgtgaat ccagtcagtt aagtaccaac    540

agtgccaaat ttaataaaca gcactggagc ttcaattgac cggtccagcc gtccaggtcc    600

aggannaggn gtnacctctg ccaacagc                                       628
```

```
<210> SEQ ID NO 6
<211> LENGTH: 604
<212> TYPE: DNA
<213> ORGANISM: Zea mays
<220> FEATURE:
<221> NAME/KEY: misc_feature
<222> LOCATION: (1)..(1)
<223> OTHER INFORMATION: n is a, c, g, or t
<220> FEATURE:
```

<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t

<400> SEQUENCE: 6
nagttcatgt tgttcattcc ttattgccac cttttaattt tcaagccctg cttgttgtat 60
acaatatcag ctaaaagata ggaaaaacct tcttccattc ttgtattgtg tagtctgtct 120
ccagtgcaga agttttattg ggcattgaag ctgcacattt attctgttac tacactacag 180
taatgtatta atatttctca tgatggagtg tttttattaa gtgacagaaa aaatgctatg 240
ccatgcatat ctttgcatca ttgcatgtgc attttgtttt ctgaggatta acatcatctt 300
ttgtgtggag ggttggtgca ggggacacta tagtacgatg aaataataga tggcttctcc 360
ttaacagcag tgaaacttca ttaacatttg gagttagagg agacagtaga gtacataata 420
gatggcttca cttcattgac atttggagtt agagaactca cttgtgagag acctganttg 480
gcacatgtgg ttatttttaa gcctgaaaaa tacatttaaa tggttttgaa tcagttcctg 540
ggggagttct aatgctaagg actagttttc attgacaant tcaaatggaa atagggcatg 600
tgct 604

<210> SEQ ID NO 7
<211> LENGTH: 359
<212> TYPE: DNA
<213> ORGANISM: Zea mays
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (69)..(116)
<223> OTHER INFORMATION: n is a, c, g, or t
<220> FEATURE:
<221> NAME/KEY: misc_feature
<222> LOCATION: (278)..(278)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t

<400> SEQUENCE: 7
acaagccatt ctcggcgcag aanttagtta acaagctaga cgaacccgcc gctacctgcg 60
gagaacctnn nnnnnnnnnn nnnnnnnnnn nnnnnnnnnn nnnnnnnnnn nnnnnnagag 120
aggaggagcg ggttgagccg gcggaggcag gcggacgagg agcatgagag gagagcggag 180
gacgggcgcg cgagcgccat tggcggttgg cgcggcctcg cttgagataa accctagtgg 240
gcgcgcagga gggctcggat gccgctatcg ctgagagnga gcctgtgagg gaggggtttg 300
gattcgggat aacgccggac ggcggcaccg cgggagtgtg gtgctgagca ncctgagca 359

<210> SEQ ID NO 8
<211> LENGTH: 889
<212> TYPE: DNA
<213> ORGANISM: Zea mays
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (232)..(232)
<223> OTHER INFORMATION: n is a, c, g, or t
<220> FEATURE:
<221> NAME/KEY: misc_feature
<222> LOCATION: (244)..(246)
<223> OTHER INFORMATION: n is a, c, g, or t
<220> FEATURE:
<221> NAME/KEY: misc_feature
<222> LOCATION: (472)..(472)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (843)..(845)
<223> OTHER INFORMATION: n is a, c, g, or t
<220> FEATURE:
<221> NAME/KEY: misc_feature
<222> LOCATION: (877)..(878)
<223> OTHER INFORMATION: n is a, c, g, or t

<400> SEQUENCE: 8

```
tttgcgaaga aatcccatcc cattcgtttt cgaaacgttg tgcatctttt cgctccccng      60

gtctgggntt tggagtttcg ctgcgcatta cgtttcagct agattttcct ggtagacaag     120

cgaagcgcgn gcgggaacat tcggatgggc atattcctgg acatccttcc caatatggga     180

gctctttact agtgtatgca acttttggng ccgctgtaaa ttttagtggc angagtacct     240

accnnnccac tgagttcgcg ctaacgtctg tgagttcttg ggggtgtaca agggcgggaa     300

acgggtgaaa tgcgcttgca tttctatgta atgctaatgt gctgcgcgtt cagcttcgtg     360

atgcgattag tgcacgaatt cagctgttct ttgctgattt gtgtcttctc cttggtgacg     420

tgcaggcatt tggtgtggga ggacggttcc tgcggccacg cctcatgcta tnccggatct     480

gatgctcctg aagctgggtg tgagccgggc accagtgtgt gcacgcttgt tgggaaggtt     540

atggcctcac aaattcatgt tattggtgaa gggtaagcag gaattttgtt ttgcttgtta     600

cnatgttcat agctaataag tgcttcggcg ttgttggaga agttcaaact ttgctgatgt     660

atgtatgtat gtatgctgtg cttgtattct tcagtaccat tggccgtgct gctttcactg     720

gaaatcatca atggattgtc catgatcctg ccactgccag tgatcacaat ctcagaccgg     780

aggtgcaatt ccttctccct tcccttgtga actgatataa atgtagccca atttaagttt     840

tcnnnggtcc attttgctgt caccttattt aaagtcnngt gccaaggga                 889
```

<210> SEQ ID NO 9
<211> LENGTH: 698
<212> TYPE: DNA
<213> ORGANISM: Zea mays
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (138)..(138)

<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t
<220> FEATURE:
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (311)..(311)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (413)..(413)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t
<220> FEATURE:
<221> NAME/KEY: misc_feature
<222> LOCATION: (582)..(584)
<223> OTHER INFORMATION: n is a, c, g, or t
<220> FEATURE:
<221> NAME/KEY: misc_feature
<222> LOCATION: (612)..(616)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (643)..(646)
<223> OTHER INFORMATION: n is a, c, g, or t
<220> FEATURE:
<221> NAME/KEY: misc_feature
<222> LOCATION: (654)..(656)
<223> OTHER INFORMATION: n is a, c, g, or t
<220> FEATURE:
<221> NAME/KEY: misc_feature
<222> LOCATION: (659)..(659)
<223> OTHER INFORMATION: n is a, c, g, or t
<220> FEATURE:
<221> NAME/KEY: misc_feature
<222> LOCATION: (664)..(665)
<223> OTHER INFORMATION: n is a, c, g, or t
<220> FEATURE:
<221> NAME/KEY: misc_feature
<222> LOCATION: (667)..(673)
<223> OTHER INFORMATION: n is a, c, g, or t
<220> FEATURE:
<221> NAME/KEY: misc_feature
<222> LOCATION: (679)..(683)
<223> OTHER INFORMATION: n is a, c, g, or t
<220> FEATURE:
<221> NAME/KEY: misc_feature
<222> LOCATION: (686)..(690)
<223> OTHER INFORMATION: n is a, c, g, or t
<220> FEATURE:
<221> NAME/KEY: misc_feature
<222> LOCATION: (692)..(697)
<223> OTHER INFORMATION: n is a, c, g, or t

<400> SEQUENCE: 9
aagccggcga gtgtggagga cgtcatgccc atcgccacgg ggctcgagcg ggaggagctg 60
gaggccgagc tcaaggtgag atggtccggt ctttgttcga gagggaggag ctggaatgca 120
cgtccggtgt gggnctgnaa atggcttctg attcctcgat ctggcctggg ttttgcaggg 180
gaagaagcgg tttganatgg atcccctggt cggccccttc ggtaccaagg ttagttggcc 240
gtagtagntt taaccgttct tcctgatgtt cctggatcgg attacacatg gaggctttct 300
atgtttatta naaaataatt agggttcttc atttattgnt attgcaatga aacgtctggg 360
gatgtatagt tcnggtaatg atttgataac atctgggtta ttgggtaaac tantcgcaag 420
tggtcagatt tgcattgttc tgcaaactat ttgcattatt gttagggaaa atgctatgtt 480
gggacgtcat ggtgcctcat ggccctcatc catcagtatc catgctttgt ngtcttacta 540
ctgtgctagn ataatgaaca ttaaccctgt ttatcataca tnnntctgat aatttggcat 600
catgtttttg gnnnnntntt taaaatcttt ttcatcttgt ctnnnntgcc atgnnntcng 660
ttgnntnnnn nnnctactnn nnnatnnnnn tnnnnnna 698

<210> SEQ ID NO 10
<211> LENGTH: 408
<212> TYPE: DNA
<213> ORGANISM: Zea mays
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (200)..(200)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t

<400> SEQUENCE: 10
atangcatgg actgntatat actangcttt atctgaagat ttgtgttcat ggagttgggt 60
aggaggccat cgtggagata ccacaggcgc cgacgcccat ctgtagctgc atgaaaccgt 120
tctnacccca ncctgtgccc caggagttct tgaggatcca gtactggntt ccctggtcat 180
cggcgccgta gccgatcgcn gtcactgcat ggttcatgtc cgtgccacag ccatccccgt 240
cgtatatgcc accctggtaa aactggaaag gactcgatcc gccgtcgacg ccaacagaca 300
ccggctggtt ggcgactgcg ttggcgagcg cgttctcgtc gccgctgggc aggtcctgga 360
agccgctgat ggtggcggct ggctggangt tttggcacgt cccttgga 408

<210> SEQ ID NO 11
<211> LENGTH: 716
<212> TYPE: DNA
<213> ORGANISM: Zea mays
<220> FEATURE:
<221> NAME/KEY: misc_feature
<222> LOCATION: (432)..(432)
<223> OTHER INFORMATION: n is a, c, g, or t

<400> SEQUENCE: 11
acagcgacga cccatcaaag attcttccca ggccgtacat ttgctgacgc agaaattggg 60
ggaaggccag gtcagcgccc aaaaccagtg agtgtctacg acgctggccc ggtggcccca 120
ggattctaga atcaaagcag ctaaacctaa aattaactca acgttacaaa actacaacct 180
tctgccctat aattctggaa tcaaagcaag taaacctaaa attcctgtgg taccatcgat 240
cctgaaaatt gcaaggttcc aataccccga cgtcaagagc agcccaaggt atgctcaatt 300
cacccatagc attacagctg atctcgtaag actccagctt ctacaggttt agcaatatgt 360
ccaaccaagg agtgcaggca caatttccga accctgcaaa aggcaagaca ttagacaaag 420
acaaacgatg gnaaaattac aatgaatagc acatggggaa gagaaacgtc aattcaacta 480
aagcatctac cactgaaatc aaggccaata aatggttgac atgatatatc agcaatgtaa 540
accaaaaaaa aaaagacaaa ccatgctcat aaacgtaagg tcaacacaac caaatttcca 600
gaattattga agacaaaaaa aaagagaagg aactgaccaa ctgatcacgc gcttatgtct 660
tgggaactgt aacattcaag atttttacat cttgatatgg cttgtcattc ttgtca 716

<210> SEQ ID NO 12
<211> LENGTH: 561
<212> TYPE: DNA
<213> ORGANISM: Zea mays
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (528)..(532)
<223> OTHER INFORMATION: n is a, c, g, or t
<220> FEATURE:
<221> NAME/KEY: misc_feature
<222> LOCATION: (539)..(540)
<223> OTHER INFORMATION: n is a, c, g, or t
<220> FEATURE:
<221> NAME/KEY: misc_feature
<222> LOCATION: (542)..(546)
<223> OTHER INFORMATION: n is a, c, g, or t
<220> FEATURE:
<221> NAME/KEY: misc_feature
<222> LOCATION: (551)..(555)
<223> OTHER INFORMATION: n is a, c, g, or t
<220> FEATURE:
<221> NAME/KEY: misc_feature
<222> LOCATION: (557)..(558)
<223> OTHER INFORMATION: n is a, c, g, or t

<400> SEQUENCE: 12
nttagttgag ctcctgctct tagcacttgg gaagatgctt cagggtttcc tctagtctca 60
ttggatgctg cctgttgctg ggatgacagg ttggtgcacc aagccaagag gcatgttcat 120
gttgctagcg ttctccgccg ctgcactgcc gtcacagttt ggctccaata agcgcacaag 180
cgatagaaag atctccattc tggttacgtc ccggttcgcc tgcatggaac agcntcatct 240
cattcctttg gatttccatt ctggttactg tttattactt cagattttga acttctagtt 300
actgtttttt acttcagatt ttgatctgaa agaatcctga ttattaaatt tagctgcatt 360
acctcaacag tgaaccgtgc ccagatttta cttttgcgca tttccatcac acccctcaag 420
atagtcagtc ctagtccttt gatgaaatca gctatctcca agaagattcc tctatcctcg 480
caaagcatct gtagaggcaa ccaagtcatc acaatcacat gcgttctnnn nnaaacatnn 540
tnnnnnaaac nnnnngnngt a 561

<210> SEQ ID NO 13
<211> LENGTH: 399
<212> TYPE: DNA
<213> ORGANISM: Zea mays
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (208)..(208)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (286)..(286)
<223> OTHER INFORMATION: n is a, c, g, or t
<220> FEATURE:
<221> NAME/KEY: misc_feature
<222> LOCATION: (310)..(310)
<223> OTHER INFORMATION: n is a, c, g, or t
<220> FEATURE:

```
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (361)..(361)
<223> OTHER INFORMATION: n is a, c, g, or t

<400> SEQUENCE: 13

gatcnggcca ggcactggct acaccgcntt gattggggtc ctggggctcg aaggaatacc     60

accaaacctg ttgaccagga ncttgaaaca ngggaacgaa acggcgtaca gcacgaccag    120

tacaattggt gcagcaataa gccaacccag catctgttgt cgacaatngc agtagtcttn    180

tgtcaatgtc ccagcaaagc aagagtanaa cagngctcct ancatangaa ngagcaggac    240

tgatttgngg aaaggntgtt cactcaccgc atggacgatg ctcatnagca catcctttga    300

ggcatgaccn gtgagaacat tcttcaatgc gtcggcngtc aaggggaagt gcccgctgcc    360

ngtgacggct tcacccaaac gcaagaaagg gacgatcaa                           399


<210> SEQ ID NO 14
<211> LENGTH: 499
<212> TYPE: DNA
<213> ORGANISM: Zea mays
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (362)..(362)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (475)..(475)
<223> OTHER INFORMATION: n is a, c, g, or t

<400> SEQUENCE: 14

caaaagatga ggggagtttt agaacataat agcacacaaa atggcacnac cntggtatga     60

tagtattaag aaaaagtgta gaatgatcat acaaagaagt atcataaana ttggttttga    120

ggatactgtc atcatctaca atgaggattt acacatcaag atatcgccca tggattttaa    180

gttgacttga aacagttttg gttatgtact tcaccatcta agatttttgc atcatctatg    240

gacattaggt cgaaaattct ctaaatacta gacacggttg tacacatact tccaacacng    300

atgaaacttg gttcaaacct ataaacatat actgtaacct tacaagaaaa tataattgag    360

tnaaagtgtg aagttcagta taanacctaa caatgctatg caagaatgct tcagtattga    420

aattatataa gatgacatgg aaacagcttg tgttgttgat gaaaagttcc aatgngtcaa    480

tttgttaggg tgcatttca                                                 499
```

<210> SEQ ID NO 15
<211> LENGTH: 649
<212> TYPE: DNA
<213> ORGANISM: Zea mays
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t
<220> FEATURE:
<221> NAME/KEY: misc_feature
<222> LOCATION: (448)..(449)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (560)..(570)
<223> OTHER INFORMATION: n is a, c, g, or t
<220> FEATURE:
<221> NAME/KEY: misc_feature
<222> LOCATION: (574)..(574)
<223> OTHER INFORMATION: n is a, c, g, or t
<220> FEATURE:
<221> NAME/KEY: misc_feature
<222> LOCATION: (576)..(588)
<223> OTHER INFORMATION: n is a, c, g, or t
<220> FEATURE:
<221> NAME/KEY: misc_feature
<222> LOCATION: (592)..(597)
<223> OTHER INFORMATION: n is a, c, g, or t
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (631)..(635)
<223> OTHER INFORMATION: n is a, c, g, or t
<220> FEATURE:
<221> NAME/KEY: misc_feature
<222> LOCATION: (641)..(648)
<223> OTHER INFORMATION: n is a, c, g, or t

<400> SEQUENCE: 15
tgtttatttt aataaaatct atgcaacttt tcacccaaat tgtggatttg tgattttttg 60
aataaacatg aacttgcgat atatgttgca catatgaagt tgttcttgtt ctatctatta 120
caatatctaa tacttcactg tctctcatga atttggatgg ntaaataaga gcacaccagt 180
tatccactag caaatcaggt agcaagcagc atgtttcgcc accatttttt cttttccttc 240
aaaaaanttc cctggtagct ggcgaacttt ttgtgttatg tgatgacact ttcttatatt 300
ttcttgaaac ccttggtaca tccaattctg ctcaaggttt agtttcatca agaatttcaa 360
attttgacct tagtatttgc ggggaacgat aaatcctgag gggtttgaac aatcgacaca 420
tttccccctt gccagtatgc tgaaaagnna tcatgttttc ttgcnaaaca tgatcatgtt 480
gttttaagtc tatgattaaa tttgattgca tccattattt acacttttct ttctttgaca 540
ggcaatactg aattatgagn nnnnnnnnnn gctnannnnn nnnnnnnnac annnnnncat 600
taaatcanta ttttatcttg agttcttgag nnnnnattat nnnnnnnna 649

<210> SEQ ID NO 16
<211> LENGTH: 691
<212> TYPE: DNA
<213> ORGANISM: Zea mays
<220> FEATURE:

<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (98)..(100)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (403)..(403)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (571)..(571)
<223> OTHER INFORMATION: n is a, c, g, or t
<220> FEATURE:
<221> NAME/KEY: misc_feature
<222> LOCATION: (592)..(592)
<223> OTHER INFORMATION: n is a, c, g, or t
<220> FEATURE:
<221> NAME/KEY: misc_feature
<222> LOCATION: (649)..(650)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
<220> FEATURE:
<221> NAME/KEY: misc_feature
<222> LOCATION: (658)..(658)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (676)..(676)
<223> OTHER INFORMATION: n is a, c, g, or t
<220> FEATURE:
<221> NAME/KEY: misc_feature
<222> LOCATION: (680)..(680)
<223> OTHER INFORMATION: n is a, c, g, or t
<220> FEATURE:
<221> NAME/KEY: misc_feature
<222> LOCATION: (686)..(688)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t

<400> SEQUENCE: 16
gcagctgaca agagntttgc caacagatat gttagcattt gatttctgtg atatggttta 60
gcagatgttg tggcccanct ttcatgttcc taaataannn aaggtttcnt attctggtca 120
catctttgca ggcaagagct gaggatattt tcacaagaag tcataagatt tgggaatngt 180
tgcaaagatc ctcagtggca caacctagat cgttatttct ccaagtaggg tcccactgtt 240
tacatggctt aatgattgat tgctagtgta atgatctcac tagtccttgt gtttgtttcc 300
aggctagagt cagaaattac accccaacca caattaaaag aaacggcgaa agcagatatg 360
cagcaactga tggcccttgt tcgncacact ggtgtgagta tcncacatgt tgacaaaaat 420
ctctagtgtt cttacagaaa ataaattgtg tnagactaca ttttgctcac ctttgcatgt 480
catgcaatca gtatgattca tgtagccatt cctgatgttg ttgctgttcc actttgnccc 540
ataggatctc taccatgaat tacacgcact ngatagattt gagcaagatt ancgccgaaa 600
gttggaggaa gagaaaagat cagttacatc tgaaaggggt atgtcgatnn tcatcnangt 660
atcncccntg tcgctncagn tgctannntn t 691

<210> SEQ ID NO 17
<211> LENGTH: 448
<212> TYPE: DNA
<213> ORGANISM: Zea mays
<220> FEATURE:
<221> NAME/KEY: misc_feature
<222> LOCATION: (286)..(286)
<223> OTHER INFORMATION: n is a, c, g, or t

<400> SEQUENCE: 17
aaggtcgatt gcagatgtcc tgattcctga agttgcttca tattgaagga tatcgtttga 60
actcattatc tcaataataa tcaaaggctt gctcttgtag ataaatgtat cattagagta 120
tcatggctgg cccacatatt actttcaaga acgtcttgga aaatgttcag atatgcacac 180
ttgctgaagt ttaagcattt ctgaggtagc aaattctttg gaagaaaatc agatacccac 240
cttggctcaa ataatccttt atgcagttgg aagtgtgtta cttcgntgct agaaaactca 300
gtgcttgttc ttttttaatc ttcaaactgc taattatata tttactacta cttttacagt 360
gtggaaggat agcaagcttc aactgcaaga acggaatcga cttggagcag gtaacctggc 420
cagaaatggg tgttcatgga gcaaggca 448

<210> SEQ ID NO 18
<211> LENGTH: 760
<212> TYPE: DNA
<213> ORGANISM: Zea mays
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (522)..(522)

<223> OTHER INFORMATION: n is a, c, g, or t
<220> FEATURE:
<221> NAME/KEY: misc_feature
<222> LOCATION: (587)..(589)
<223> OTHER INFORMATION: n is a, c, g, or t
<220> FEATURE:
<221> NAME/KEY: misc_feature
<222> LOCATION: (614)..(620)
<223> OTHER INFORMATION: n is a, c, g, or t
<220> FEATURE:
<221> NAME/KEY: misc_feature
<222> LOCATION: (622)..(625)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (641)..(644)
<223> OTHER INFORMATION: n is a, c, g, or t
<220> FEATURE:
<221> NAME/KEY: misc_feature
<222> LOCATION: (648)..(650)
<223> OTHER INFORMATION: n is a, c, g, or t
<220> FEATURE:
<221> NAME/KEY: misc_feature
<222> LOCATION: (653)..(653)
<223> OTHER INFORMATION: n is a, c, g, or t
<220> FEATURE:
<221> NAME/KEY: misc_feature
<222> LOCATION: (655)..(659)
<223> OTHER INFORMATION: n is a, c, g, or t
<220> FEATURE:
<221> NAME/KEY: misc_feature
<222> LOCATION: (668)..(670)
<223> OTHER INFORMATION: n is a, c, g, or t
<220> FEATURE:
<221> NAME/KEY: misc_feature
<222> LOCATION: (672)..(673)
<223> OTHER INFORMATION: n is a, c, g, or t
<220> FEATURE:
<221> NAME/KEY: misc_feature
<222> LOCATION: (677)..(687)
<223> OTHER INFORMATION: n is a, c, g, or t
<220> FEATURE:
<221> NAME/KEY: misc_feature
<222> LOCATION: (690)..(691)
<223> OTHER INFORMATION: n is a, c, g, or t
<220> FEATURE:
<221> NAME/KEY: misc_feature
<222> LOCATION: (693)..(700)
<223> OTHER INFORMATION: n is a, c, g, or t
<220> FEATURE:
<221> NAME/KEY: misc_feature
<222> LOCATION: (703)..(703)
<223> OTHER INFORMATION: n is a, c, g, or t
<220> FEATURE:
<221> NAME/KEY: misc_feature
<222> LOCATION: (707)..(711)
<223> OTHER INFORMATION: n is a, c, g, or t
<220> FEATURE:
<221> NAME/KEY: misc_feature
<222> LOCATION: (716)..(726)
<223> OTHER INFORMATION: n is a, c, g, or t
<220> FEATURE:
<221> NAME/KEY: misc_feature
<222> LOCATION: (729)..(738)
<223> OTHER INFORMATION: n is a, c, g, or t
<220> FEATURE:
<221> NAME/KEY: misc_feature
<222> LOCATION: (740)..(758)
<223> OTHER INFORMATION: n is a, c, g, or t

<400> SEQUENCE: 18

```
ggccngactg ctcctgcgaa gacgangctg acatcgagta cgacagcagc cgtatctggg     60

ttctggacnc gcccaacata ccaaagcctc caccagagac ggagaggcta gtgattatgg    120

gcggtgacta caccagaatg gacacgtatt acgtcatgcc caatgggaag cgtgcgaggt    180

gtgctggtga cgtggacaag tttctggang caaatccagc gtacaaaagc cgcatatctg    240

cttcggattt cgactttgca ccgccccgagg ttgttgagga gactgttgtt tctcacaatt    300

ttctgcctct gcaaggttgc caaggccaag aaacaggaga aggcagagag gcacacaaaa    360

taggtgaaag cagagaggca tcgatgctct gaactgtgcc tgtgccctgt gctatgtagg    420

tgatagtccg ctcaagatca cgtcacgtct cgttcctatc tagtacggtt gtctatctcg    480

gctgaagtta atgtagtagg tcttcttgcg tgttaattcc tngggaatat atgagatgtt    540

taataattag ttgcttaggc cttaaaactg tgcttcctta acttttnnnc ttcagtcatc    600

tcgtatatgc acgnnnnnnn cnnnngctag cagcntagnc nnnnactnnn cancnnnnna    660

tcatagcnnn anntctnnnn nnnnnnngcn ngnnnnnnnn ctnacannnn ntacannnnn    720

nnnnnngann nnnnnnnnan nnnnnnnnnn nnnnnnnnat                          760
```

<210> SEQ ID NO 19
<211> LENGTH: 489
<212> TYPE: DNA
<213> ORGANISM: Zea mays
<220> FEATURE:
<221> NAME/KEY: misc_feature
<222> LOCATION: (187)..(187)
<223> OTHER INFORMATION: n is a, c, g, or t

<400> SEQUENCE: 19

```
gatcctcaaa tctacctata atcatccatc aagatgcata gctacatact gttctgcgga     60

atgctgcctc agtatgatat caagaacacg aagcgcctcc agggagttct cagattcttc    120

gcctctaatg acttgaccaa tagcactcat aggaacctct gctgcaaaat ttatctccac    180

tttgaangtt ttcgtctggt atggcctcct cactctcttc ctatcaccac ctccaggact    240

gtcattacct ccagggctcc cattggcagc agtcctacaa ccacaaacaa aaaacatggc    300

aattactgat tctgggtaag cataaacaac aagaaagcag atcaaagact aaaactaact    360

ttccagtaga tacgtcctcc aagacaacgg tgaactcatt cttttttgt ggaagaccac    420

caactgtaaa caggctcttt tctccatcat atgcaaagtc cttgttagaa agctctgcac    480

gatatgtct                                                            489
```

<210> SEQ ID NO 20
<211> LENGTH: 768
<212> TYPE: DNA
<213> ORGANISM: Zea mays
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (335)..(335)
<223> OTHER INFORMATION: n is a, c, g, or t
<220> FEATURE:

```
<221> NAME/KEY: misc_feature
<222> LOCATION: (418)..(418)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (753)..(764)
<223> OTHER INFORMATION: n is a, c, g, or t

<400> SEQUENCE: 20

atgctgaaag taattccata cctagaaaca ctttcataca ctcatttgcc tcaacaccag      60

catctgcaca acaataggaa atagaaagtg gcttaaccag ttcatctgta tgtcggaaat     120

aaacaaaaac ggntgaaggc acagaaacgt gcaagggaca tccacacaga tgaacacaca     180

gcgcaattaa cntgtatgat tgtatctcat agagcaatcc ttatgggact gatagaaccc     240

caaaagcatg atatctcttc aggtttgcag aaaccaaaac aggtctacag tttnaattat     300

gtcaagtgca ctccacaaag aaagcaaaat gaagnaaaat gtaagatgaa tagaatgagg     360

ttcaccattt ccttatcaca ctttaacctg tgtgactatc caaatcctct aaagacantg     420

catnaggggc ttaaccaaac aaaaggttag atccaatgct ccacaagcag acaagcaata     480

aattacagac aatgcacagc ctcgatccag aaaacagggc aaagcctaac aatttagcaa     540

cttctttcca cctccttttt actaatagag aataaactcc ccacgcttca atgtcgcaac     600

caccaaatta agcaaggcag acacatctaa atgagaagca gcagcctctc ggctacgctc     660

cacaggcata tccggcggaa gccgccaggn caaaataaac ataaaaatga acacacgccg     720

gaacccaaca agacagcagg cgcgtcncaa cannnnnnnn nnnngcag                  768


<210> SEQ ID NO 21
<211> LENGTH: 621
<212> TYPE: DNA
<213> ORGANISM: Zea mays
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(8)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (128)..(150)
<223> OTHER INFORMATION: n is a, c, g, or t
<220> FEATURE:
<221> NAME/KEY: misc_feature
<222> LOCATION: (266)..(266)
<223> OTHER INFORMATION: n is a, c, g, or t
<220> FEATURE:
<221> NAME/KEY: misc_feature
```

<222> LOCATION: (383)..(383)
<223> OTHER INFORMATION: n is a, c, g, or t
<220> FEATURE:
<221> NAME/KEY: misc_feature
<222> LOCATION: (386)..(386)
<223> OTHER INFORMATION: n is a, c, g, or t
<220> FEATURE:
<221> NAME/KEY: misc_feature
<222> LOCATION: (500)..(503)
<223> OTHER INFORMATION: n is a, c, g, or t
<220> FEATURE:
<221> NAME/KEY: misc_feature
<222> LOCATION: (507)..(508)
<223> OTHER INFORMATION: n is a, c, g, or t
<220> FEATURE:
<221> NAME/KEY: misc_feature
<222> LOCATION: (512)..(519)
<223> OTHER INFORMATION: n is a, c, g, or t
<220> FEATURE:
<221> NAME/KEY: misc_feature
<222> LOCATION: (545)..(545)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (556)..(557)
<223> OTHER INFORMATION: n is a, c, g, or t
<220> FEATURE:
<221> NAME/KEY: misc_feature
<222> LOCATION: (561)..(570)
<223> OTHER INFORMATION: n is a, c, g, or t
<220> FEATURE:
<221> NAME/KEY: misc_feature
<222> LOCATION: (581)..(583)
<223> OTHER INFORMATION: n is a, c, g, or t
<220> FEATURE:
<221> NAME/KEY: misc_feature
<222> LOCATION: (588)..(589)
<223> OTHER INFORMATION: n is a, c, g, or t
<220> FEATURE:
<221> NAME/KEY: misc_feature
<222> LOCATION: (592)..(618)
<223> OTHER INFORMATION: n is a, c, g, or t

<400> SEQUENCE: 21
ngngnnnngt ggagcgcgcg tccgcgctgc tccgcccgca cggcgccgcc gtggtggagt 60
acaccagcca ggcctacacc aagagcatcc cnggccacta cgtcatctac tgggagctcc 120
tggccaannn nnnnnnnnnn nnnnnnnnnn tgggcgaggg gacgctggag aggtgctgcc 180
tggagatgga ggaggcgctg aacacggtgt acaggcagag ccgcgtggcg gacgggtcca 240
tcgggccgct ggagatccgg gtggtncggc cgggcacctt cgaggagctc atggactacg 300
ccatctcccg cggcgcgtcc atcaaccagt acaaggtgcc ccggtgcgtg acgttcccgc 360
ccatcatcga gctcctggac tcncgngtcg tgtccagcca cttcagcccc gcgctgccgc 420
actggacccc cggccagcgc tccgactccg actagacacg cgggccggcg tgcggcgagg 480
cgtgtccggc gcgcttaatn nnnctgnnaa tnnnnnnnnt gcgtatcgca gacgtagaat 540
atgcncntga aattannata nnnnnnnnnn ttggaatttt nnntactnnc annnnnnnnn 600
nnnnnnnnnn nnnnnnnntg t 621

<210> SEQ ID NO 22
<211> LENGTH: 562
<212> TYPE: DNA
<213> ORGANISM: Zea mays
<220> FEATURE:
<221> NAME/KEY: misc_feature
<222> LOCATION: (430)..(433)

<223> OTHER INFORMATION: n is a, c, g, or t
<220> FEATURE:
<221> NAME/KEY: misc_feature
<222> LOCATION: (488)..(488)
<223> OTHER INFORMATION: n is a, c, g, or t

<400> SEQUENCE: 22
tcgttctttt ttttattcca tctgattttg tgttatgtca cagtttatga tggtaaggga 60
acccttgagg aaggggaaac cgctgaagcg cgtttcatta agatccaagc agcgtatgag 120
ctgttgattg atggtgaaag gagaagagca tatgatagag agcatcatgt gaatccgatg 180
aaggtctgaa ttttcttggc cacttaggtt atcatttcat tatgtgcagg atgcagttcc 240
tccactccat ctttgtattt gtttgttaat tactgttgtc tgttgccacc tattttactc 300
gaggattaca cattttagtc acagtattag ttttttaatc ctgatttagc ttcatggttc 360
tcaagccaag aaaaggaagc atcattccat ccttgtcagc tactaactta caaagcagta 420
atgtgtcttn nnntgttttt cttgcttcaa aactggacta ggactgatgg aatatatcag 480
caactaanaa ctgctaatta cacgtgggtc caacattcat atgccttgaa atagttgagc 540
acttgagacc ttattatctg ca 562

<210> SEQ ID NO 23
<211> LENGTH: 768
<212> TYPE: DNA
<213> ORGANISM: Zea mays
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (596)..(598)
<223> OTHER INFORMATION: n is a, c, g, or t
<220> FEATURE:
<221> NAME/KEY: misc_feature
<222> LOCATION: (641)..(642)
<223> OTHER INFORMATION: n is a, c, g, or t
<220> FEATURE:
<221> NAME/KEY: misc_feature
<222> LOCATION: (647)..(649)
<223> OTHER INFORMATION: n is a, c, g, or t
<220> FEATURE:
<221> NAME/KEY: misc_feature
<222> LOCATION: (653)..(654)
<223> OTHER INFORMATION: n is a, c, g, or t
<220> FEATURE:
<221> NAME/KEY: misc_feature
<222> LOCATION: (656)..(662)
<223> OTHER INFORMATION: n is a, c, g, or t
<220> FEATURE:
<221> NAME/KEY: misc_feature
<222> LOCATION: (665)..(674)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t
<220> FEATURE:
<221> NAME/KEY: misc_feature
<222> LOCATION: (691)..(693)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (723)..(724)
<223> OTHER INFORMATION: n is a, c, g, or t
<220> FEATURE:
<221> NAME/KEY: misc_feature
<222> LOCATION: (731)..(735)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (747)..(751)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t

<400> SEQUENCE: 23
ctgatacagg tagctcaaaa aacacaccag gaacatgctt aaataatgct gcaaaaggga 60
atgacaagtt gatcagaggc agcagcaagc tacctgatac atatagttca caaaacacac 120
caggaacatg cctacatact gctgtaaaag ggagtggcaa gttgatcagc ggcagcagca 180
agctacctga tacagatcca ctggagtcac cttgcagcaa ctttactgag gtcgacatga 240
ttgtctcacc ttcaccactt gtctcatgga acactggatc ttgtatngtn gagagcggaa 300
agcagttgtt tctcttgaca ccactgccaa aaacaaaagc atgctcatca aggtgccaaa 360
catcaaaaac ccagatgaag acagtttcta gcactgacca attgaacaat cttctaaggc 420
ctgtttcaaa gctaaccatt tctgataata atcatcctga tctagagcaa agtgtgaagg 480
taaaggaatc atggactagc actacgacac ctcatgttgc tctagcaaac aaggcctcac 540
tagaagacaa gctctgttcg cctcgtactt tctcagttca gaagagcaga acactnnnta 600
gatcatgcct gaagacagca ttatctagca agcagcagct nntctcnnna atnncnnnnn 660
nnagnnnnnn nnnngacant gacagcaatg nnncnattgg ggatgacaaa tgctcatctg 720
atnnaatctc nnnnnatnta gcatcannnn ntgatattna tgggctta 768

<210> SEQ ID NO 24
<211> LENGTH: 626
<212> TYPE: DNA
<213> ORGANISM: Zea mays
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (470)..(470)
<223> OTHER INFORMATION: n is a, c, g, or t
<220> FEATURE:
<221> NAME/KEY: misc_feature
<222> LOCATION: (598)..(598)
<223> OTHER INFORMATION: n is a, c, g, or t
<220> FEATURE:
<221> NAME/KEY: misc_feature
<222> LOCATION: (600)..(600)

<223> OTHER INFORMATION: n is a, c, g, or t
<220> FEATURE:
<221> NAME/KEY: misc_feature
<222> LOCATION: (604)..(606)
<223> OTHER INFORMATION: n is a, c, g, or t
<220> FEATURE:
<221> NAME/KEY: misc_feature
<222> LOCATION: (611)..(616)
<223> OTHER INFORMATION: n is a, c, g, or t
<220> FEATURE:
<221> NAME/KEY: misc_feature
<222> LOCATION: (623)..(623)
<223> OTHER INFORMATION: n is a, c, g, or t

<400> SEQUENCE: 24

```
tgtgctccat attnaacaca atagcgtaaa tagtgctaat tttagcttct aaaacantta      60

acacaaatag atccaaacat gccgtaatca cgtccaacgt taancaaana gaaactatgc     120

tgaagtgtgc acaagtgaca ctgaatggta ccaatccaga gtgaaccggc tagagctaca     180

tggcaccaaa gtgcttgaac ggggagaaaa taacgcgaaa ccttggccgg tggagcagca     240

gaataaccaa gcgaagaatg tttactgaac ctcgattagg gccgcaagaa aatgcggcga     300

attaatcagc ttaaccaaaa cctgggaatt ccagagtcac gttcggctga aacgctgttg     360

ttaggcagcc tctgtattct gccagagaac tcattaacct aggcaagata taacaaacat     420

acatcaataa tggtttcacg tcaacagatt agacaattaa ttccaatgan taatcactac     480

cgctgctcca aattaaatgc atttctagac aagtacgtct aggtgcattg ccaaaaatga     540

atttatttcg gatggatgga gtaagactcc tgtgcatgaa atcatgaata catctgangn     600

catnnnaaga nnnnnntgaa atngat                                          626
```

<210> SEQ ID NO 25
<211> LENGTH: 707
<212> TYPE: DNA
<213> ORGANISM: Zea mays
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (583)..(583)
<223> OTHER INFORMATION: n is a, c, g, or t
<220> FEATURE:
<221> NAME/KEY: misc_feature
<222> LOCATION: (589)..(590)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (641)..(642)
<223> OTHER INFORMATION: n is a, c, g, or t
<220> FEATURE:
<221> NAME/KEY: misc_feature
<222> LOCATION: (646)..(661)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (668)..(670)
<223> OTHER INFORMATION: n is a, c, g, or t
<220> FEATURE:
<221> NAME/KEY: misc_feature
<222> LOCATION: (678)..(683)
<223> OTHER INFORMATION: n is a, c, g, or t
<220> FEATURE:
<221> NAME/KEY: misc_feature
<222> LOCATION: (686)..(687)
<223> OTHER INFORMATION: n is a, c, g, or t
<220> FEATURE:
<221> NAME/KEY: misc_feature
<222> LOCATION: (689)..(696)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t

<400> SEQUENCE: 25
catgcctgcn natgatgggg tgctgcaccc ccttgcggtc acacacgcgg cccacggcgg 60
ccaccacggc gcccgcgtac tcctccaggc tgtacgccac cgacatgtcg gtctgcgccg 120
agtgggtccc gtcgtagtca atgccgaggc cgccgccgac gtcgatgacg cgcatgtccg 180
cgccgaggcg ggcgagctcg cagtagatct gcgcggcctc gccgacgccg tcggagagca 240
gggcggtggt cgggatctgg gagccgatgt ggaagtgcag cagctggagg cagtcgagca 300
taccnatggc cttgagcttg gtgaccacgg acagtatctg cgcggcgctg aggccgaact 360
tgcccttctc cccggacgtg gagccgaagt ggccggcgtg cttggtgcgc agcttggcgc 420
gcatgccgac gacggggcgc acgccgaggc gncggctggc ctcgacgaca atgtcgagct 480
cctcctcctg ctcgagcacg atgacggtgt tgaggcccat ggagcgcgcc atgagcgcga 540
gcgagacgta gccgtcgtcc ttgtacccgt tgcagatgag canggcgtnn aggccgccgc 600
gcgcgncgag gcagctcatg gcgagcagca gctcnggctt nnagcnnnnn nnnnnnnnnn 660
nccnaaannn cgcgccgnnn nnnacnntnn nnnnnncgac gtanctg 707

<210> SEQ ID NO 26
<211> LENGTH: 543
<212> TYPE: DNA
<213> ORGANISM: Zea mays
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (470)..(472)
<223> OTHER INFORMATION: n is a, c, g, or t
<220> FEATURE:
<221> NAME/KEY: misc_feature
<222> LOCATION: (474)..(479)
<223> OTHER INFORMATION: n is a, c, g, or t
<220> FEATURE:
<221> NAME/KEY: misc_feature
<222> LOCATION: (487)..(493)
<223> OTHER INFORMATION: n is a, c, g, or t
<220> FEATURE:
<221> NAME/KEY: misc_feature
<222> LOCATION: (495)..(499)
<223> OTHER INFORMATION: n is a, c, g, or t
<220> FEATURE:
<221> NAME/KEY: misc_feature
<222> LOCATION: (502)..(509)

<223> OTHER INFORMATION: n is a, c, g, or t
<220> FEATURE:
<221> NAME/KEY: misc_feature
<222> LOCATION: (511)..(517)
<223> OTHER INFORMATION: n is a, c, g, or t
<220> FEATURE:
<221> NAME/KEY: misc_feature
<222> LOCATION: (522)..(531)
<223> OTHER INFORMATION: n is a, c, g, or t
<220> FEATURE:
<221> NAME/KEY: misc_feature
<222> LOCATION: (535)..(539)
<223> OTHER INFORMATION: n is a, c, g, or t

<400> SEQUENCE: 26
ctgcagtacc tttaccaaca tgatgctttt gtttttctat aagcatgtgt ggcacactag 60
ttatcagctc cgcaggaact acatcagcat tgtgaaattc atcggtagtg gactgcctag 120
ttgaagtcat atcgttgttt tcaaaattag cagccttgct tctggaaaca ttcgactcag 180
tgctagacaa gcttcttctc aagaagcccc ttcccttcat cttgaggaca ccaccaccct 240
tttggtccat tgatggctgg agaatcttcc atgtctcttc ccaatagttg ggtgtagaca 300
agagagaant tcctctcgat gaggatgaag gaagatttgc ttcaagggca aaagattgca 360
gtaacttggc tttctcaatt aagctcttta agtcaatatc ttctggaaaa tttaacaacc 420
tcactaggca agaagtcgca tgttcactcc ctaataagga ggatctgagn nngnnnnnna 480
ttgatannnn nnncnnnnna annnnnnnnc nnnnnnnaga annnnnnnnn ntaannnnnt 540
aat 543

<210> SEQ ID NO 27
<211> LENGTH: 750
<212> TYPE: DNA
<213> ORGANISM: Zea mays
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (296)..(296)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (541)..(541)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t
<220> FEATURE:
<221> NAME/KEY: misc_feature
<222> LOCATION: (676)..(677)
<223> OTHER INFORMATION: n is a, c, g, or t
<220> FEATURE:
<221> NAME/KEY: misc_feature
<222> LOCATION: (683)..(683)
<223> OTHER INFORMATION: n is a, c, g, or t
<220> FEATURE:
<221> NAME/KEY: misc_feature
<222> LOCATION: (692)..(692)
<223> OTHER INFORMATION: n is a, c, g, or t
<220> FEATURE:
<221> NAME/KEY: misc_feature
<222> LOCATION: (700)..(701)
<223> OTHER INFORMATION: n is a, c, g, or t
<220> FEATURE:
<221> NAME/KEY: misc_feature
<222> LOCATION: (706)..(711)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t

<400> SEQUENCE: 27
tcaaccctgt gcaaggtgca ggtcatgatc caaagattgc caacggtaat agttctgctc 60
acccaggctt aaattccggt gtccagtcgt caggttcccc acctaggcga acgctggcaa 120
acccaaagca ccctgatctg gccttgcagc tangaggtag ccattnacat agtttgcctt 180
agtactgtga tctgtgacag aggcatgagt tcaacactgc ttcgtccggt accttgncaa 240
gcggagcacg agaccgatcg aagaggtaag aagtgtttgg tttgtcgtca gagngnggng 300
gtggcggcng cgggacatcn tgtagggtcc ctcgatttaa ttgatcattt gaccccctgt 360
gagttgtttg taaaagggta gggtagcttc tgtacaggtt ctaatcttac tggagatgat 420
aatgcttcgg atgaaggcag cgcccgctgt ccagcttgta acattattga tagtagaaag 480
aagaggaggg aagcatacag gcgaaaaggc agtgaataat ttgtgccttt ttgttttgcc 540 nccegaccct gagtggacgc actccgtttc caaatgtacg agtggctaac ctcggtcagc 600
ttttcttgag cattcgttcg ttcatgttgc tgtcgtttgt tatgtttctt ntgcttgtta 660
ggctcactnc tngcgnnctg gcntctgtag gncatgtgan ngcgcnnnnn ngcaatgtct 720
gcatggacac atcgctgtga tcttgttnca 750

<210> SEQ ID NO 28
<211> LENGTH: 311
<212> TYPE: DNA
<213> ORGANISM: Zea mays
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (39)..(45)
<223> OTHER INFORMATION: n is a, c, g, or t
<220> FEATURE:
<221> NAME/KEY: misc_feature
<222> LOCATION: (134)..(134)

<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t

<400> SEQUENCE: 28
tttnaggact ctcttatagt cttatttcaa gttgactann nnnnntacag agaaagaggc 60
atacctgttg gaccagtgta tactgcaagc tgcctgtaca acaaccattg ggatcaaagc 120
tcaattgcat atcncaatcg ctcagctaaa ggcattggaa aaacaagtag aaagtctagc 180
agcttactca gttgcatatc ccaatcgctc agctaaaggc atnattccta gcatgctgaa 240
aagaaaaacc aatccctgca attttaatgt cacgtgaacc atgtcagcat taagttaaca 300
gggggggggg g 311

<210> SEQ ID NO 29
<211> LENGTH: 703
<212> TYPE: DNA
<213> ORGANISM: Zea mays
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (682)..(682)
<223> OTHER INFORMATION: n is a, c, g, or t

<400> SEQUENCE: 29
ctcctcaaag catttcaacg ctctatctgg cagtgacact ctagcccaac ctttaatcaa 60
cgtggtaaac gtcttgacat ttggtttcaa tccaacatct gccatttctt gaatcacatt 120
ttccgctctc tacaataaat agttcaaaca agaaattagt gaataatgtg caacaaaggc 180
caggattact tctccattca cattttcccg atgacaataa gctaagatga agccatgtag 240
gcacattgtg tgaatnaagg gcattgcaga cattgtgttc agccaccttc aaaaactcca 300
ataatgtcca actgtaacac cacaaactac taatcaaata ttttgatgca aaatgcacac 360
acctgcatgt ctccngcttt gcagcatgca tttatgtagg aagtaaatgt atggatgtta 420
ggagggattc catcctcttt catttgtttc aacaaatctg ctgcctccca gacatctcct 480
ctccgagccc aactacatga aagaatgtaa tgacacagta ttttagtctt tagattatac 540
aatactctta acagggattt gacaaactat ttttgattat aacatggctc aagtaaatca 600
taaattgaca tgatatgaaa gcaagtgtct gaattactga ggtaaataat aataattttg 660
gtccttttct atagtatttc anaaatggac atcatatatg gca 703

<210> SEQ ID NO 30
<211> LENGTH: 27
<212> TYPE: DNA
<213> ORGANISM: Zea mays

<400> SEQUENCE: 30
gagttgtcaa atttgaacct aagcttt 27

<210> SEQ ID NO 31
<211> LENGTH: 21
<212> TYPE: DNA
<213> ORGANISM: Zea mays

<400> SEQUENCE: 31
catgccctcc ttttctgatg a 21

<210> SEQ ID NO 32
<211> LENGTH: 26
<212> TYPE: DNA
<213> ORGANISM: Zea mays

<400> SEQUENCE: 32
tgatcaccag aagctattga gaaaag 26

<210> SEQ ID NO 33
<211> LENGTH: 17
<212> TYPE: DNA
<213> ORGANISM: Zea mays

<400> SEQUENCE: 33
gccatggcca agtcgaa 17

<210> SEQ ID NO 34
<211> LENGTH: 19
<212> TYPE: DNA
<213> ORGANISM: Zea mays

<400> SEQUENCE: 34
tcgccggact ccagtagct 19

<210> SEQ ID NO 35
<211> LENGTH: 29
<212> TYPE: DNA
<213> ORGANISM: Zea mays

<400> SEQUENCE: 35
acttcattga catttggagt tagagaact 29

<210> SEQ ID NO 36
<211> LENGTH: 17
<212> TYPE: DNA
<213> ORGANISM: Zea mays

<400> SEQUENCE: 36
ggctcggatg ccgctat 17

<210> SEQ ID NO 37
<211> LENGTH: 22
<212> TYPE: DNA
<213> ORGANISM: Zea mays

<400> SEQUENCE: 37
ttcgaaacgt tgtgcatctt tt 22

<210> SEQ ID NO 38
<211> LENGTH: 23
<212> TYPE: DNA
<213> ORGANISM: Zea mays

<400> SEQUENCE: 38
cccttcggta ccaaggttag ttg 23

<210> SEQ ID NO 39
<211> LENGTH: 20
<212> TYPE: DNA

<213> ORGANISM: Zea mays

<400> SEQUENCE: 39
acgcccatct gtagctgcat 20

<210> SEQ ID NO 40
<211> LENGTH: 23
<212> TYPE: DNA
<213> ORGANISM: Zea mays

<400> SEQUENCE: 40
cctgcaaaag gcaagacatt aga 23

<210> SEQ ID NO 41
<211> LENGTH: 16
<212> TYPE: DNA
<213> ORGANISM: Zea mays

<400> SEQUENCE: 41
cccggttcgc ctgcat 16

<210> SEQ ID NO 42
<211> LENGTH: 21
<212> TYPE: DNA
<213> ORGANISM: Zea mays

<400> SEQUENCE: 42
ggctcgaagg aataccacca a 21

<210> SEQ ID NO 43
<211> LENGTH: 32
<212> TYPE: DNA
<213> ORGANISM: Zea mays

<400> SEQUENCE: 43
ctaaatacta gacacggttg tacacatact tc 32

<210> SEQ ID NO 44
<211> LENGTH: 21
<212> TYPE: DNA
<213> ORGANISM: Zea mays

<400> SEQUENCE: 44
cgccaccatt ttttcttttc c 21

<210> SEQ ID NO 45
<211> LENGTH: 23
<212> TYPE: DNA
<213> ORGANISM: Zea mays

<400> SEQUENCE: 45
gatgttgttg ctgttccact ttg 23

<210> SEQ ID NO 46
<211> LENGTH: 25
<212> TYPE: DNA
<213> ORGANISM: Zea mays

<400> SEQUENCE: 46
atcctttatg cagttggaag tgtgt 25

<210> SEQ ID NO 47
<211> LENGTH: 20

<212> TYPE: DNA
<213> ORGANISM: Zea mays

<400> SEQUENCE: 47
tgctggtgac gtggacaagt 20

<210> SEQ ID NO 48
<211> LENGTH: 24
<212> TYPE: DNA
<213> ORGANISM: Zea mays

<400> SEQUENCE: 48
ggaacctctg ctgcaaaatt tatc 24

<210> SEQ ID NO 49
<211> LENGTH: 24
<212> TYPE: DNA
<213> ORGANISM: Zea mays

<400> SEQUENCE: 49
accagttcat ctgtatgtcg gaaa 24

<210> SEQ ID NO 50
<211> LENGTH: 20
<212> TYPE: DNA
<213> ORGANISM: Zea mays

<400> SEQUENCE: 50
agccaggcct acaccaagag 20

<210> SEQ ID NO 51
<211> LENGTH: 24
<212> TYPE: DNA
<213> ORGANISM: Zea mays

<400> SEQUENCE: 51
caaaactgga ctaggactga tgga 24

<210> SEQ ID NO 52
<211> LENGTH: 22
<212> TYPE: DNA
<213> ORGANISM: Zea mays

<400> SEQUENCE: 52
ccttcaccac ttgtctcatg ga 22

<210> SEQ ID NO 53
<211> LENGTH: 29
<212> TYPE: DNA
<213> ORGANISM: Zea mays

<400> SEQUENCE: 53
gtttcacgtc aacagattag acaattaat 29

<210> SEQ ID NO 54
<211> LENGTH: 18
<212> TYPE: DNA
<213> ORGANISM: Zea mays

<400> SEQUENCE: 54
ctgggagccg atgtggaa 18

<210> SEQ ID NO 55

<211> LENGTH: 25
<212> TYPE: DNA
<213> ORGANISM: Zea mays

<400> SEQUENCE: 55
cttccatgtc tcttcccaat agttg 25

<210> SEQ ID NO 56
<211> LENGTH: 18
<212> TYPE: DNA
<213> ORGANISM: Zea mays

<400> SEQUENCE: 56
ccctgatctg gccttgca 18

<210> SEQ ID NO 57
<211> LENGTH: 23
<212> TYPE: DNA
<213> ORGANISM: Zea mays

<400> SEQUENCE: 57
catatcccaa tcgctcagct aaa 23

<210> SEQ ID NO 58
<211> LENGTH: 26
<212> TYPE: DNA
<213> ORGANISM: Zea mays

<400> SEQUENCE: 58
gacaataagc taagatgaag ccatgt 26

<210> SEQ ID NO 59
<211> LENGTH: 25
<212> TYPE: DNA
<213> ORGANISM: Zea mays

<400> SEQUENCE: 59
tcctgaccat agcatcttta tgctt 25

<210> SEQ ID NO 60
<211> LENGTH: 28
<212> TYPE: DNA
<213> ORGANISM: Zea mays

<400> SEQUENCE: 60
gagattcaag tgaaaaacat tagtccaa 28

<210> SEQ ID NO 61
<211> LENGTH: 20
<212> TYPE: DNA
<213> ORGANISM: Zea mays

<400> SEQUENCE: 61
cgaatctggc ggtgcatata 20

<210> SEQ ID NO 62
<211> LENGTH: 21
<212> TYPE: DNA
<213> ORGANISM: Zea mays

<400> SEQUENCE: 62
gcgtgctgca ggtctctgta g 21

<210> SEQ ID NO 63
<211> LENGTH: 27
<212> TYPE: DNA
<213> ORGANISM: Zea mays

<400> SEQUENCE: 63
tggtacttaa ctgactggat tcacatg 27

<210> SEQ ID NO 64
<211> LENGTH: 29
<212> TYPE: DNA
<213> ORGANISM: Zea mays

<400> SEQUENCE: 64
aaccatttaa atgtattttt caggcttaa 29

<210> SEQ ID NO 65
<211> LENGTH: 19
<212> TYPE: DNA
<213> ORGANISM: Zea mays

<400> SEQUENCE: 65
ggcgttatcc cgaatccaa 19

<210> SEQ ID NO 66
<211> LENGTH: 18
<212> TYPE: DNA
<213> ORGANISM: Zea mays

<400> SEQUENCE: 66
gcgcagcgaa actccaaa 18

<210> SEQ ID NO 67
<211> LENGTH: 23
<212> TYPE: DNA
<213> ORGANISM: Zea mays

<400> SEQUENCE: 67
gtaatccgat ccaggaacat cag 23

<210> SEQ ID NO 68
<211> LENGTH: 16
<212> TYPE: DNA
<213> ORGANISM: Zea mays

<400> SEQUENCE: 68
cgccgatgac caggga 16

<210> SEQ ID NO 69
<211> LENGTH: 23
<212> TYPE: DNA
<213> ORGANISM: Zea mays

<400> SEQUENCE: 69
tcttccccat gtgctattca ttg 23

<210> SEQ ID NO 70
<211> LENGTH: 22
<212> TYPE: DNA
<213> ORGANISM: Zea mays

<400> SEQUENCE: 70
accagaatgg aaatccaaag ga 22

<210> SEQ ID NO 71
<211> LENGTH: 19
<212> TYPE: DNA
<213> ORGANISM: Zea mays

<400> SEQUENCE: 71
tgctgtacgc cgtttcgtt 19

<210> SEQ ID NO 72
<211> LENGTH: 25
<212> TYPE: DNA
<213> ORGANISM: Zea mays

<400> SEQUENCE: 72
gcattcttgc atagcattgt taggt 25

<210> SEQ ID NO 73
<211> LENGTH: 25
<212> TYPE: DNA
<213> ORGANISM: Zea mays

<400> SEQUENCE: 73
tcatcacata acacaaaaag ttcgc 25

<210> SEQ ID NO 74
<211> LENGTH: 24
<212> TYPE: DNA
<213> ORGANISM: Zea mays

<400> SEQUENCE: 74
tcttttctct tcctccaact ttcg 24

<210> SEQ ID NO 75
<211> LENGTH: 27
<212> TYPE: DNA
<213> ORGANISM: Zea mays

<400> SEQUENCE: 75
tgaagattaa aaaagaacaa gcactga 27

<210> SEQ ID NO 76
<211> LENGTH: 20
<212> TYPE: DNA
<213> ORGANISM: Zea mays

<400> SEQUENCE: 76
cgaagcagat atgcggcttt 20

<210> SEQ ID NO 77
<211> LENGTH: 23
<212> TYPE: DNA
<213> ORGANISM: Zea mays

<400> SEQUENCE: 77
ggaagagagt gaggaggcca tac 23

<210> SEQ ID NO 78
<211> LENGTH: 20
<212> TYPE: DNA
<213> ORGANISM: Zea mays

<400> SEQUENCE: 78
tggatgtccc ttgcacgttt 20

<210> SEQ ID NO 79
<211> LENGTH: 21
<212> TYPE: DNA
<213> ORGANISM: Zea mays

<400> SEQUENCE: 79
gccaggagct cccagtagat g 21

<210> SEQ ID NO 80
<211> LENGTH: 22
<212> TYPE: DNA
<213> ORGANISM: Zea mays

<400> SEQUENCE: 80
tgaatgttgg acccacgtgt aa 22

<210> SEQ ID NO 81
<211> LENGTH: 24
<212> TYPE: DNA
<213> ORGANISM: Zea mays

<400> SEQUENCE: 81
tggtgtcaag agaaacaact gctt 24

<210> SEQ ID NO 82
<211> LENGTH: 29
<212> TYPE: DNA
<213> ORGANISM: Zea mays

<400> SEQUENCE: 82
tacttgtcta gaaatgcatt taatttgga 29

<210> SEQ ID NO 83
<211> LENGTH: 19
<212> TYPE: DNA
<213> ORGANISM: Zea mays

<400> SEQUENCE: 83
tgtccgtggt caccaagct 19

<210> SEQ ID NO 84
<211> LENGTH: 24
<212> TYPE: DNA
<213> ORGANISM: Zea mays

<400> SEQUENCE: 84
agcaaatctt ccttcatcct catc 24

<210> SEQ ID NO 85
<211> LENGTH: 25
<212> TYPE: DNA
<213> ORGANISM: Zea mays

<400> SEQUENCE: 85
tgcctctgtc acagatcaca gtact 25

<210> SEQ ID NO 86
<211> LENGTH: 22
<212> TYPE: DNA
<213> ORGANISM: Zea mays

<400> SEQUENCE: 86
tgcagggatt ggtttttctt tt 22

<210> SEQ ID NO 87
<211> LENGTH: 21
<212> TYPE: DNA
<213> ORGANISM: Zea mays

<400> SEQUENCE: 87
ggctgaacac aatgtctgca a 21

<210> SEQ ID NO 88
<211> LENGTH: 16
<212> TYPE: DNA
<213> ORGANISM: Zea mays

<400> SEQUENCE: 88
aaactcgaaa attgtg 16

<210> SEQ ID NO 89
<211> LENGTH: 15
<212> TYPE: DNA
<213> ORGANISM: Zea mays

<400> SEQUENCE: 89
atggtcctag atgtc 15

<210> SEQ ID NO 90
<211> LENGTH: 13
<212> TYPE: DNA
<213> ORGANISM: Zea mays

<400> SEQUENCE: 90
caagtcggct gcc 13

<210> SEQ ID NO 91
<211> LENGTH: 14
<212> TYPE: DNA
<213> ORGANISM: Zea mays

<400> SEQUENCE: 91
tgcaggtcct ggct 14

<210> SEQ ID NO 92
<211> LENGTH: 14
<212> TYPE: DNA
<213> ORGANISM: Zea mays

<400> SEQUENCE: 92
ccacctgcac attg 14

<210> SEQ ID NO 93
<211> LENGTH: 16
<212> TYPE: DNA
<213> ORGANISM: Zea mays

<400> SEQUENCE: 93
acctgacttg gcacat 16

<210> SEQ ID NO 94
<211> LENGTH: 14
<212> TYPE: DNA
<213> ORGANISM: Zea mays

<400> SEQUENCE: 94
aggctccctc tcag 14

<210> SEQ ID NO 95
<211> LENGTH: 13
<212> TYPE: DNA
<213> ORGANISM: Zea mays

<400> SEQUENCE: 95
tccccgggtc tgg 13

<210> SEQ ID NO 96
<211> LENGTH: 19
<212> TYPE: DNA
<213> ORGANISM: Zea mays

<400> SEQUENCE: 96
cggttaaatc tactacggc 19

<210> SEQ ID NO 97
<211> LENGTH: 14
<212> TYPE: DNA
<213> ORGANISM: Zea mays

<400> SEQUENCE: 97
accgttctca cccc 14

<210> SEQ ID NO 98
<211> LENGTH: 13
<212> TYPE: DNA
<213> ORGANISM: Zea mays

<400> SEQUENCE: 98
cgatggaaaa att 13

<210> SEQ ID NO 99
<211> LENGTH: 15
<212> TYPE: DNA
<213> ORGANISM: Zea mays

<400> SEQUENCE: 99
acagcatcat ctcat 15

<210> SEQ ID NO 100
<211> LENGTH: 15
<212> TYPE: DNA
<213> ORGANISM: Zea mays

<400> SEQUENCE: 100
accaggacct tgaaa 15

<210> SEQ ID NO 101
<211> LENGTH: 16
<212> TYPE: DNA
<213> ORGANISM: Zea mays

<400> SEQUENCE: 101
caacacagat gaaact 16

<210> SEQ ID NO 102
<211> LENGTH: 14
<212> TYPE: DNA
<213> ORGANISM: Zea mays

<400> SEQUENCE: 102
taccagggaa tttt 14

<210> SEQ ID NO 103
<211> LENGTH: 16
<212> TYPE: DNA
<213> ORGANISM: Zea mays

<400> SEQUENCE: 103
cgcactagat agattt 16

<210> SEQ ID NO 104
<211> LENGTH: 15
<212> TYPE: DNA
<213> ORGANISM: Zea mays

<400> SEQUENCE: 104
cttcgctgct agaaa 15

<210> SEQ ID NO 105
<211> LENGTH: 13
<212> TYPE: DNA
<213> ORGANISM: Zea mays

<400> SEQUENCE: 105
ctggacgcaa atc 13

<210> SEQ ID NO 106
<211> LENGTH: 14
<212> TYPE: DNA
<213> ORGANISM: Zea mays

<400> SEQUENCE: 106
cagacgaaaa cttt 14

<210> SEQ ID NO 107
<211> LENGTH: 15
<212> TYPE: DNA
<213> ORGANISM: Zea mays

<400> SEQUENCE: 107
aaacggatga aggca 15

<210> SEQ ID NO 108
<211> LENGTH: 14
<212> TYPE: DNA
<213> ORGANISM: Zea mays

<400> SEQUENCE: 108
atcccgggcc acta 14

<210> SEQ ID NO 109
<211> LENGTH: 15
<212> TYPE: DNA
<213> ORGANISM: Zea mays

<400> SEQUENCE: 109
agcaactaaa aactg 15

<210> SEQ ID NO 110
<211> LENGTH: 19
<212> TYPE: DNA
<213> ORGANISM: Zea mays

<400> SEQUENCE: 110
acactggatc ttgtatagt 19

<210> SEQ ID NO 111
<211> LENGTH: 19
<212> TYPE: DNA
<213> ORGANISM: Zea mays

<400> SEQUENCE: 111
ccaatgaata atcactacc 19

<210> SEQ ID NO 112
<211> LENGTH: 16
<212> TYPE: DNA
<213> ORGANISM: Zea mays

<400> SEQUENCE: 112
cataccaatg gccttg 16

<210> SEQ ID NO 113
<211> LENGTH: 15
<212> TYPE: DNA
<213> ORGANISM: Zea mays

<400> SEQUENCE: 113
acaagagaga acttc 15

<210> SEQ ID NO 114
<211> LENGTH: 16
<212> TYPE: DNA
<213> ORGANISM: Zea mays

<400> SEQUENCE: 114
agccattcac atagtt 16

<210> SEQ ID NO 115
<211> LENGTH: 15
<212> TYPE: DNA
<213> ORGANISM: Zea mays

<400> SEQUENCE: 115
tgctaggaat tatgc 15

<210> SEQ ID NO 116
<211> LENGTH: 16
<212> TYPE: DNA
<213> ORGANISM: Zea mays

<400> SEQUENCE: 116
ttgtgtgaat aaaggg 16

<210> SEQ ID NO 117
<211> LENGTH: 15
<212> TYPE: DNA
<213> ORGANISM: Zea mays

<400> SEQUENCE: 117
tcaaactcga aactt 15

<210> SEQ ID NO 118
<211> LENGTH: 17
<212> TYPE: DNA

<213> ORGANISM: Zea mays

<400> SEQUENCE: 118
tggtcctagt tgtcact 17

<210> SEQ ID NO 119
<211> LENGTH: 13
<212> TYPE: DNA
<213> ORGANISM: Zea mays

<400> SEQUENCE: 119
caagtgggct gcc 13

<210> SEQ ID NO 120
<211> LENGTH: 15
<212> TYPE: DNA
<213> ORGANISM: Zea mays

<400> SEQUENCE: 120
tgcaggtcct agctt 15

<210> SEQ ID NO 121
<211> LENGTH: 14
<212> TYPE: DNA
<213> ORGANISM: Zea mays

<400> SEQUENCE: 121
cacctgccca ttgg 14

<210> SEQ ID NO 122
<211> LENGTH: 17
<212> TYPE: DNA
<213> ORGANISM: Zea mays

<400> SEQUENCE: 122
acctgatttg gcacatg 17

<210> SEQ ID NO 123
<211> LENGTH: 14
<212> TYPE: DNA
<213> ORGANISM: Zea mays

<400> SEQUENCE: 123
aggctcactc tcag 14

<210> SEQ ID NO 124
<211> LENGTH: 14
<212> TYPE: DNA
<213> ORGANISM: Zea mays

<400> SEQUENCE: 124
tcccctggtc tggg 14

<210> SEQ ID NO 125
<211> LENGTH: 18
<212> TYPE: DNA
<213> ORGANISM: Zea mays

<400> SEQUENCE: 125
cggttaaacc tactacgg 18

<210> SEQ ID NO 126
<211> LENGTH: 15

<212> TYPE: DNA
<213> ORGANISM: Zea mays

<400> SEQUENCE: 126
aaaccgttct gaccc 15

<210> SEQ ID NO 127
<211> LENGTH: 15
<212> TYPE: DNA
<213> ORGANISM: Zea mays

<400> SEQUENCE: 127
aaacgatggc aaaat 15

<210> SEQ ID NO 128
<211> LENGTH: 14
<212> TYPE: DNA
<213> ORGANISM: Zea mays

<400> SEQUENCE: 128
acagcgtcat ctca 14

<210> SEQ ID NO 129
<211> LENGTH: 16
<212> TYPE: DNA
<213> ORGANISM: Zea mays

<400> SEQUENCE: 129
ccaggatctt gaaaca 16

<210> SEQ ID NO 130
<211> LENGTH: 15
<212> TYPE: DNA
<213> ORGANISM: Zea mays

<400> SEQUENCE: 130
aacacggatg aaact 15

<210> SEQ ID NO 131
<211> LENGTH: 13
<212> TYPE: DNA
<213> ORGANISM: Zea mays

<400> SEQUENCE: 131
ccagggaact ttt 13

<210> SEQ ID NO 132
<211> LENGTH: 14
<212> TYPE: DNA
<213> ORGANISM: Zea mays

<400> SEQUENCE: 132
cgcactggat agat 14

<210> SEQ ID NO 133
<211> LENGTH: 16
<212> TYPE: DNA
<213> ORGANISM: Zea mays

<400> SEQUENCE: 133
acttcggtgc tagaaa 16

<210> SEQ ID NO 134

<211> LENGTH: 13
<212> TYPE: DNA
<213> ORGANISM: Zea mays

<400> SEQUENCE: 134
ctggaggcaa atc 13

<210> SEQ ID NO 135
<211> LENGTH: 15
<212> TYPE: DNA
<213> ORGANISM: Zea mays

<400> SEQUENCE: 135
cagacgaaaa cattc 15

<210> SEQ ID NO 136
<211> LENGTH: 13
<212> TYPE: DNA
<213> ORGANISM: Zea mays

<400> SEQUENCE: 136
aacggctgaa ggc 13

<210> SEQ ID NO 137
<211> LENGTH: 15
<212> TYPE: DNA
<213> ORGANISM: Zea mays

<400> SEQUENCE: 137
atccctggcc actac 15

<210> SEQ ID NO 138
<211> LENGTH: 16
<212> TYPE: DNA
<213> ORGANISM: Zea mays

<400> SEQUENCE: 138
cagcaactaa caactg 16

<210> SEQ ID NO 139
<211> LENGTH: 18
<212> TYPE: DNA
<213> ORGANISM: Zea mays

<400> SEQUENCE: 139
cactggatct tgtatggt 18

<210> SEQ ID NO 140
<211> LENGTH: 18
<212> TYPE: DNA
<213> ORGANISM: Zea mays

<400> SEQUENCE: 140
ccaatgagta atcactac 18

<210> SEQ ID NO 141
<211> LENGTH: 15
<212> TYPE: DNA
<213> ORGANISM: Zea mays

<400> SEQUENCE: 141
cataccgatg gcctt 15

<210> SEQ ID NO 142
<211> LENGTH: 14
<212> TYPE: DNA
<213> ORGANISM: Zea mays

<400> SEQUENCE: 142
caagagagaa tttc 14

<210> SEQ ID NO 143
<211> LENGTH: 16
<212> TYPE: DNA
<213> ORGANISM: Zea mays

<400> SEQUENCE: 143
agccattgac atagtt 16

<210> SEQ ID NO 144
<211> LENGTH: 15
<212> TYPE: DNA
<213> ORGANISM: Zea mays

<400> SEQUENCE: 144
tgctaggaat aatgc 15

<210> SEQ ID NO 145
<211> LENGTH: 15
<212> TYPE: DNA
<213> ORGANISM: Zea mays

<400> SEQUENCE: 145
tgtgaatgaa gggca 15

<210> SEQ ID NO 146
<211> LENGTH: 20
<212> TYPE: DNA
<213> ORGANISM: Artificial sequence
<220> FEATURE:
<223> OTHER INFORMATION: Primer

<400> SEQUENCE: 146
cccgttcaca tcaccatcca 20

<210> SEQ ID NO 147
<211> LENGTH: 24
<212> TYPE: DNA
<213> ORGANISM: Artificial sequence
<220> FEATURE:
<223> OTHER INFORMATION: Primer

<400> SEQUENCE: 147
gaacctacac agcaatacga gaaa 24

<210> SEQ ID NO 148
<211> LENGTH: 23
<212> TYPE: DNA
<213> ORGANISM: Artificial sequence
<220> FEATURE:
<223> OTHER INFORMATION: Primer

<400> SEQUENCE: 148
caagtgacag caatgctgtt tca 23

<210> SEQ ID NO 149
<211> LENGTH: 21
<212> TYPE: DNA

<213> ORGANISM: Artificial sequence
<220> FEATURE:
<223> OTHER INFORMATION: Primer

<400> SEQUENCE: 149
gtcgaaatca gtgcgttcga a 21

<210> SEQ ID NO 150
<211> LENGTH: 16
<212> TYPE: DNA
<213> ORGANISM: Artificial sequence
<220> FEATURE:
<223> OTHER INFORMATION: Probe

<400> SEQUENCE: 150
cggtgaacgt gcaaaa 16

<210> SEQ ID NO 151
<211> LENGTH: 2089
<212> TYPE: DNA
<213> ORGANISM: Zea mays

<400> SEQUENCE: 151
caccggcggt ctcatcaccg ccatgctcac cgcgcccggc aaggacaagc ggcctctcta 60
cgctgccaag gacatcaact acttttacat ggagaactgc ccgcgcatct tccctcagaa 120
gtgagtccga tgctgccgcc attgttctcg catccatcca gcatcgtacg tcctctatac 180
atctgcggat gatcatttgc gcatgtttgt ggcatgcatg tgagcaggag caggcttgcg 240
gccgccatgt ccgcgctgag gaagccaaag tacaacggca agtgcatgcg cagcctgatt 300
aggagcatcc tcggcgagac gagggtaagc gagacgctga ccaacgtcat catccctgcc 360
ttcgacatca ggctgctgca gcctatcatc ttctctacct acgacgtacg tacgtcgtca 420
cgaatgattc atctgtacgt cgtcgcatgc gaatggctgc ctacgccgtg cgctaacata 480
ctcagctctt tccgatctgc tgcgccaatt tgcaggccaa gagcacgcct ctgaagaacg 540
cgctgctctc ggacgtgtgc attggcacgt ccgccgcgcc gacctacctc ccggcgcact 600
acttccagac tgaagacgcc aacggcaagg agcgcgaata caacctcatc gacggcggtg 660
tggcggccaa caacccggta actgactagc taactgcaaa acgaacgcac agactccatg 720
tccatggcgg cccacaaggt cgatgctaat tgttgcttat gtatgtcgcc cgattgcaca 780
tgcgtagacg atggttgcga tgacgcagat caccaaaaag atgcttgcca gcaaggacaa 840
ggccgaggag ctgtacccag tgaacccgtc gaactgccgc aggttcctgg tgctgtccat 900
cgggacgggg tcgacgtccg agcagggcct ctacacggcg cggcagtgct cccggtgggg 960
catctgccgg tggctccgca acaacggcat ggcccccatc atcgacatct tcatggcggc 1020
cagctcggac ctggtggaca tccacgtcgc cgcgatgttc cagtcgctcc acagcgacgg 1080
cgactaccta cgcatccagg acaactcgct ccgtggcgcc gcggcaaccg tggacgcggc 1140
gacgccggag aacatgcgga cgctcgtcgg gatcggggag cggatgctgg cacagcgggt 1200
gtccagggtc aacgtggaga cagggagcga ggtacgaacc ggtgaccgga gaaggaagca 1260
atgccgatgc cctcggtggg ctcgctaggc agctctccga ggagaggaga acaaggctcg 1320
cgcgccgcgt ctctgccatc aaccccagaa gctctagatg tgcgccctac gatatctaag 1380
acaagtggct ttactgtcaa tcacatgctt gtaaataagt agactttatt ttaataaaat 1440
ataaatatat atatattctg ataaccaaga ttcgaaccct cacttataca caattttatc 1500
ttatttttta taaaatgaga atggaaagga ctaccgtgaa cgactataga accaatcata 1560

-continued

```
ctagtttaaa atgctcgtaa gctatgacga acctagtagg ccggtgctgg accattccaa   1620

aaaacctata aaaataaatt taatattaaa ttaaacatat ggtctatata tcagatatta   1680

aactcaaaag aataattatt ataatttatc ttagctaaaa ggttgagaaa ggtatgcgtt   1740

aaaaaagagt tttaacccat ttttatagct tatttgatcg cccgtccact tttagggagc   1800

gaggtggtac tatgcagaag tgttgcgctg tgtgcgactt actatcatgt tgggtttagg   1860

tggattctca cgacccaatg atagacgaga agtgtgggag atgaacaaac ctacgcattt   1920

cgcgtacgac acatgtgttt gaacaacgag ttagattgga aaaaatataa tgaccttttt   1980

tgcaaaaatg actacaatga aaaccaggaa aaccggtgct tcataggagt agagatttga   2040

cggtaaattg ttacgatcta ctggtatttg ctgcgaggat gtattcgct               2089
```

METHODS AND COMPOSITIONS FOR GENOME EDITING VIA HAPLOID INDUCTION

CROSS-REFERENCE TO RELATED APPLICATIONS

This application is a continuation of U.S. patent application Ser. No. 16/275,200, filed Feb. 13, 2019, which is a continuation of International Application No. PCT/US2017/051248, filed Sep. 13, 2017, which claims the priority of U.S. Provisional Application No. 62/394,409, filed Sep. 14, 2016, each of which is incorporated herein by reference in its entirety.

INCORPORATION OF SEQUENCE LISTING

A sequence listing contained in the file named "61934WO_ST25.txt" which is 65,536 bytes (measured in MS-Windows®) and was created on Sep. 7, 2017, is filed electronically herewith and incorporated by reference its entirety.

FIELD

The present disclosure provides methods and compositions for effecting genome modification using genome editing in combination with haploid induction crosses.

BACKGROUND

Delivering useful traits to diverse germplasm traditionally involves multiple rounds of backcrossing to move the trait from a donor germplasm to the line(s) of interest. This process can take years to complete, and it often requires extensive field or greenhouse space to grow the requisite plants. Furthermore, for some native traits, poor recombination around the trait of interest results in linkage drag of a substantial portion of the donor genome which may have unwanted, or even deleterious, phenotypic effects. Plant breeders can use haploid induction lines and doubled haploids to speed the integration of a desired trait into a line of interest.

Recent discoveries in genome editing technologies have revealed new systems by which mutations, including genomic rearrangements, can be targeted to specific loci within a plant genome, for example, zinc fingers, transcription activator-like effectors, and clustered regularly interspaced short palindromic repeats (CRISPR). These new tools have showed promise in allowing greater possibilities for plant scientists to enable the incorporation of specific nucleotide edits into specific target sequences within a target genome that were previously impossible, or so statistically unlikely to occur so as to be unfeasible in a high-throughput and/or industrial setting.

However, an important drawback of these systems is the persistence of mutational elements in the cell after the desired edit has been made that could further affect gene expression and/or create additional, unwanted mutations in the plant genome. Current plant breeding methods teach that to eliminate such genome editing components (GECs) from a plant after a desired edit is made, it is necessary to backcross plants containing the sequences to a recurrent parent that lacks the sequences and select for those progeny that have lost the GEC but retain the desired edit incorporated into their genome. This process is slow, laborious, and requires considerable investment in resources to accomplish.

Thus, there is a need in the art to efficiently eliminate the GEC in a cell following editing and for scaling up a GE system to efficiently produce a wide assortment and/or combination of different edits in a large number of different plant germplasms on an industrial or commercial scale, to meet the demand of modern competitive farming systems.

The methods and compositions described herein satisfy the needs in the art by exposing gene editing components in a donor line to modify the genome in a desired line without the need for multiple rounds of backcrossing and without substantial linkage drag.

SUMMARY

In one embodiment, the invention is directed to a method of modifying a plant genome that comprises providing a first plant comprising at least one genome editing component (GEC) and crossing the first plant with a second plant to generate a modified genome of the second plant wherein the genome of the second plant is modified by the at least one GEC component. A third plant is produced from the cross of the first and second plant wherein the third plant comprises the modified genome of the second plant and wherein the third plant substantially lacks the GEC. In some embodiments, the first plant is a haploid inducer plant.

In another embodiment, the invention is directed to a method of modifying a plant genome that comprises providing a first plant comprising at least one supernumerary chromosome, wherein the supernumerary chromosome comprises at least one genome edicting component (GEC). The first plant is crossed with a second plant to generate a modified genome of the second plant by action of the GEC component on the genome of the second plant. The cross between the first and second plant results in a third plant comprising the modified genome of the second plant but substantially lacking the GEC.

In a further embodiment, the invention is directed to a method of modifying a plant genome that comprises providing a first plant comprising at least one genome editing component (GEC) on a carrier DNA molecule. The first plant is crossed with a second plant, wherein the genome of the second plant is sufficiently exposed to the at least one GEC to modify the proteins encoded by the at least one GEC. The cross of the first and second plant then results in a third plant comprising the modified genome of the second plant but substantially lacking the GEC. In some embodiments, the first plant is a haploid inducer plant.

In another embodiment, the invention is directed to a method of modifying a plant genome that comprises providing a first plant of a first plant species comprising at least one genome editing component (GEC). The first plant of the first plant species is crossed with a second plant of a second plant species, wherein the at least one GEC modifies a genome of the second plant of the second plant species to generate a modified genome of the second plant. The method further comprises recovering an F1 hybrid plant from the cross of the first and second plant and further crossing the F1 hybrid plant to obtain a progeny plant comprising the modified genome of the second plant but wherein the progeny plant substantially lacks the nuclear genome of the first plant.

Further aspects and embodiments of the present invention will be apparent from the description provided herein. It should be understood that the description and examples provided are intended for purposes of illustration only and are not intended to limit the scope of Applicants' invention.

DETAILED DESCRIPTION

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York). The inventors do not intend to be limited to a mechanism or mode of action. Reference thereto is provided for illustrative purposes only.

The practice of the present disclosure employs, unless otherwise indicated, conventional techniques of biochemistry, chemistry, molecular biology, microbiology, cell biology, genomics and biotechnology, which are within the skill of the art. See Green and Sambrook, Molecular Cloning: A Laboratory Manual, 4th edition (2012); Current Protocols In Molecular Biology (F. M. Ausubel, et al. eds., (1987)); the series Methods In Enzymology (Academic Press, Inc.): PCR 2: A Practical Approach (M. J. MacPherson, B. D. Hames and G. R. Taylor eds. (1995)); Harlow and Lane, eds. (1988) Antibodies, A Laboratory Manual; Animal Cell Culture (R. I. Freshney, ed. (1987)); Recombinant Protein Purification: Principles And Methods, 18-1142-75, GE Healthcare Life Sciences; C. N. Stewart, A. Touraev, V. Citovsky, T. Tzfira eds. (2011) Plant Transformation Technologies (Wiley-Blackwell); and R. H. Smith (2013) Plant Tissue Culture. Techniques And Experiments (Academic Press, Inc.).

All references cited herein are incorporated by reference in their entireties.

As used herein, the singular form "a," "an," and "the" include plural references unless the context clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

As used herein, "plant" refers to a whole plant or a cell or tissue culture derived from a plant, comprising any of: whole plants, plant components or organs (e.g., leaves, stems, roots, etc.), plant tissues, seeds, plant cells, and/or progeny of the same. A progeny plant can be from any filial generation, e.g., F1, F2, F3, F4, F5, F6, F7, etc. A plant cell is a biological cell of a plant, taken from a plant or derived through culture from a cell taken from a plant. Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root. Plant cells, as used herein, includes protoplasts and protoplasts with a cell wall. A plant cell may be a protoplast, a gamete producing cell, or a cell or collection of cells that can regenerate into a whole plant.

As used herein, "plant genome" refers to a nuclear genome, a mitochondrial genome, or a plastid (e.g., chloroplast) genome of a plant cell.

As used herein, "transgenic" refers to a plant cell, a plant, a plant part, or a seed whose genome has been altered by the stable integration of exogenous DNA. A transgenic line includes a plant regenerated from an originally-transformed plant cell and progeny transgenic plants from later generations or crosses of a transformed plant. As used herein, a "transgene" refers to a polynucleotide that has been transferred into a genome by any method known in the art. In one aspect, a transgene is an exogenous polynucleotide. In one aspect, a transgene is an endogenous polynucleotide that is integrated into a new genomic locus where it is not normally found.

The use of the term "polynucleotide" is not intended to limit the present disclosure to polynucleotides comprising deoxyribonucleic acids (DNA). Those of ordinary skill in the art will recognize that polynucleotides and nucleic acid molecules can comprise ribonucleotides (RNAs) and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like.

Disclosed herein is the discovery that an entirely different system, used for very different purposes, could be combined with a GEC system to rapidly create a wide variety of different edits, and combinations of edits (e.g "trait stacks") among a large number of diverse germplasms. The discovery includes, among other concepts, the realization that a haploid induction system provides a means of solving many of the problems currently plaguing large-scale plant breeding programs attempting to adopt GE systems like CRISPR-Cas9.

In certain embodiments, a GEC can be placed on any one of a variety of carrier DNA molecules that are either spontaneously eliminated from a cell after an edit has been made, or that can be easily removed from a cell after an edit has been made. One important example of a carrier DNA molecule is the genome of a plant that is used as a haploid inducer. Other examples include supernumerary chromosomes, for example, a B chromosome. Other important examples are provided elsewhere herein.

In certain embodiments, a plant is produced that contains a carrier chromosome comprising a GEC, e.g. a GEC transformed into the genome of a maize maternal haploid inducer, and then this inducer plant can be used as a male parent in a large number of different crosses to a wide range of germplasms. Important advantages revealed by the discovery of this system include that 1) a large number of different edits (i.e. mutations) and combinations of mutations (i.e. "stacks") can be rapidly deployed to a large number of different germplasms without having to custom design each edit for each germplasm each time, and 2) the GEC, and the editing activities it encodes, are rapidly eliminated (e.g. spontaneously through the usual mechanisms of inducer genome elimination) after the edit has been made, eventually yielding a haploid cell whose genome is substantially identical to its female parent, aside from the edit that was generated by the GEC. For example, once a maize haploid inducer has been transformed with a desired GEC (in certain embodiments capable of altering many genes), it can then be used repeatedly as a parent in induction crosses with a wide range of different germplasms to create a discrete, desired edit in a wide range of genomes very rapidly, and with much less investment than is required using current methods.

Haploids/Haploid Induction Lines/Doubling Haploids

The instant disclosure provides methods and compositions useful for modifying a genome using haploid induction techniques.

As used herein, a "haploid" cell or nucleus comprises a single set of unpaired chromosomes (x). In contrast, a "diploid" cell or nucleus comprises two complete sets of chromosomes (2×) that are capable of homologous pairing. The haploid number of chromosomes can be represented by "n," and the diploid number of chromosomes can be represented by "2n." For example, in a diploid species such as corn, n=x=10, and 2n=2x=20. A polyploid cell or nucleus comprises more than two complete sets of chromosomes. For example, some wheat lines are hexaploids, meaning they contain three sets of paired chromosomes (2n=6x=42). Both diploid and polyploid cells and nuclei can be reduced to haploid states.

As used herein, a "haploid plant" describes a sporophyte comprising a plurality of cells comprising a haploid nuclear genome. Occasionally, sectors of an otherwise haploid plant can spontaneously double to form diploid or polyploid sectors. The frequency of spontaneous chromosome doubling varies depending on the species. Rates of spontaneous chromosome doubling up to 70-90% in barley, up to 25-70% in wheat, up to 50-60% in rice, up to 50-90% in rye, and up to 20% in corn have been reported.

An haploid plant provided herein can be a maternal haploid plant, meaning it has lost its paternal nuclear genome while retaining its maternal nuclear genome. Alternatively, a haploid plant provided herein can be a paternal haploid plant, meaning it has lost its maternal nuclear genome while retaining its paternal nuclear genome. Typically, maternal mitochondria and plastid (e.g., chloroplast) genomes are retained in both maternal and paternal haploid plants.

Haploid plants provided herein can originate spontaneously, or they can be produced by using various haploid induction techniques. In one aspect, haploid plants provided herein are generated by pollinating a female plant with pollen from a "haploid induction" (HI) line of the same species. As used herein, a "haploid induction (HI) plant" is a plant capable of inducing haploidization in a progeny plant by eliminating one set of chromosomes. HI lines typically produce maternal haploids at low frequencies (10%). As a non-limiting example, pollen from a plant of the haploid-inducing corn line Stock 6 can be used to generate maternal haploids in progeny plants via elimination of the Stock 6 chromosomes. As another non-limiting example, a corn plant harboring a mutation in the indeterminate gametophyte1 (ig1) locus is capable of inducing paternal haploids upon fertilization via elimination of the maternal chromosomes; the maternal mitochondrial and plastid genomes are retained in ig1-induced paternal haploids. As a further non-limiting example, pollen from a cotton plant harboring a mutation in the semigamy (se) locus is capable of producing either a paternal or a maternal haploid upon fertilization. However, haploid cotton plants are only generated when the maternal parent harbors the requisite se mutation. See, for example, Chaudhari. 1978. Bulletin of the Torrey Botanical Club. 105:98-103. In one aspect, this disclosure provides a HI plant. As another non-limiting example, it has been shown that manipulation of the centromere-specific histone CENH3 can induce the formation of haploids in *Arabidopsis thaliana*. See, for example, Ravi and Chan 2010. Nature. 464:615-619. In one aspect, an HI line provided herein comprises a modified CENH3 protein. As another non-limiting example, it was also found that plants with loss of functional Msi2 protein due to a nucleotide polymorphism resulting in the introduction of a premature stop codon in the Msi2 protein, are able to induce haploid offspring after a cross to or with a wild type plant comprising a functional Msi2 protein (WO 2017058023 A1). In another aspect, an HI line provided herein comprises a modified Msi2 protein. As another non-limiting example, it was found that plants comprising modified CENPC protein comprising one or more active mutations which affect the functioning of CENPC protein yet allow plants expressing said modified CENPC protein to be viable, are able to induce haploid offspring after a cross to or with a wild type plant comprising an endogenous CENPC protein (WO 2017058022 A1). In another aspect, an HI line provided herein comprises a modified CENPC protein. As another non-limiting example, it was found that plants with a silenced patatin-like phospholipase 2A are able to induce haploid offspring (U.S. Pat. No. 9,677,082 B2). In another aspect, an HI line provided herein comprises a silenced patatin-like phospholipase 2A gene.

In one aspect, an HI plant provided herein is of a species selected from the group consisting of a corn plant, a rye plant, a wheat plant, a barley plant, a Tripsacum plant, a sorghum plant, a pearl millet plant, a soybean plant, an alfalfa plant, a sugarcane plant, a cotton plant, a canola plant, a potato plant, and a rice plant.

In another aspect, haploid induction can be achieved by pollinating a domesticated plant variety with pollen from a wild relative in an intragenic and/or interspecific cross. In yet another aspect, haploid induction is achieved by pollinating an egg cell of a first species from a first genus with pollen from a plant of a second species in a second genus in an "intergenic cross." Such intragenic and intergenic crosses are often referred to as "wide crosses" or "wide hybridizations." In one aspect, a wide cross provided herein results in the loss of the paternal nuclear genome. In another aspect, a wide cross provided herein results in the loss of the maternal nuclear genome. Those skilled in the art will recognize that in some instances hybrid progeny resulting from a wide cross must be backcrossed to the parent species comprising the desired nuclear genome in order to eliminate the nuclear genome of the second, undesired species. In one aspect, the first species in a wide cross is selected from the group consisting of wheat, rye, oat, barley, and Tripsacum, and the second species is corn. In another aspect, the first species in a wide cross is Tripsacum and the second species is corn. In another aspect, the first species in a wide cross is wheat, and the second species is corn. In another aspect, the first species in a wide cross is a wild species of barley and the second species is a domesticated species of barley. In another aspect, the first species in a wide cross is wheat, and the second species is selected from the group consisting of sorghum and pearl millet. In yet another aspect, the first species in a wide cross is a wild potato species (e.g., *Solanum phreja*), and the second species is a domesticated potato species. In another aspect, the first species in a wide cross is a species of the genus *Orychophragmus* and the second species is canola. In another aspect, the first species in a wide cross is *Glycine tomentella* and the second species is soybean. In another aspect, the first species in a wide cross is Oryza minuta and the second species is rice.

In one aspect, a haploid plant provided herein is produced by pollinating a plant using irradiated pollen. In another aspect, a haploid plant provided herein is produced in vitro. In another aspect, a maternal haploid plant provided herein is produced from the in vitro culturing of unpollinated female flower parts (e.g., ovules, placenta attached ovules, ovaries, whole flower buds). In yet another aspect, a paternal haploid plant provided herein is produced from the in vitro culturing of immature anthers.

In one aspect, in vitro embryo rescue is required to recover a haploid plant provided herein following a haploid induction event. In another aspect, a trait (e.g., color marker, such as an athocyanin marker like R1-nj, and/or an oil content marker, such as that described in PCT Application PCT/US2015/049344, titled Improved Methods of Plant Breeding Using High-Throughput Seed Sorting, filed Sep. 10, 2015 and corresponding U.S. patent application Ser. No. 14/206,238, the disclosure of each being incorporated by reference herein in their entirety, and/or a morphological marker capable of distinguishing haploid embryos from diploid embryos) is incorporated into a genome of a HI plant provided herein, a recipient plant provided herein, or both to facilitate the identification, differentiation and/or sorting of haploid embryos from diploid embryos. Haploid induction can be confirmed by the presence/absence of a phenotypic marker in the seed coat, aleurone, embryo, endosperm, or a combination thereof. As a non-limiting example, the corn R-nj color marker (R is a locus that conditions red and purple anthocyanin pigmentation), which colors the crown portion of the seed aleurone and the embryo red or purple, can be incorporated into a HI inducing corn line. When the HI line comprising R-nj is crossed as a male onto a colorless female line, haploid candidates can be selected by choosing seeds that have a R-nj pattern in the endosperm coupled with a colorless embryo. Haploid induction can also be confirmed by molecular markers that indicate a lack of heterogeneity. Such markers can be examined by techniques known in the art such as, without being limiting, sequence analysis (e.g., Sanger, 454, Illumina, Pac-Bio), PCR, Southern hybridization, fluorescence in situ hybridization (FISH), and ELISA.

Haploid plants often form aberrant floral structures and are unable to proceed through meiosis due to the absence of one set of homologous chromosomes. It is often desirable to convert a haploid plant to a diploid plant (a "doubled haploid") in a process known as "haploid doubling" or "chromosome doubling." Haploid doubling allows the generation of a plant that is homozygous at all loci in the nuclear genome in a single generation. In one aspect, a haploid plant provided herein is converted to a doubled haploid plant. In one aspect, a method of chromosome doubling provided herein comprises the use of a chromosome doubling agent selected from the group consisting of nitrous oxide (N20) gas, colchicine, oryzalin, amiprophosmethyl, trifluralin, caffeine, and pronamide See for example, Doubled Haploid Production in Crop Plants: A Manual (Eds. M. Maluszynski, K. J. Kasha, B. P. Forster, and I. Szarejko (2003), Kluwer Academic Publishers); Prigge and Melchinger, 2012, Plant Cell Culture Protocols, 877: 161-172; and Kato and Geiger, 2002, Plant Breeding, 121: 370-377 (each of which are incorporated by reference herein in their entireties). In another aspect, a method of chromosome doubling provided herein comprises the use of colchicine. In yet another aspect, a method of chromosome doubling provided herein comprises the use of N20 gas. In still another aspect, a method of chromosome doubling provided herein comprises the use of colchicine or nitrous oxide gas. As used herein, when referring to chromosome count, "doubling" refers to increasing the chromosome number by a factor of two. For example, a haploid nuclear genome comprising 10 chromosomes is doubled to become a diploid nuclear genome comprising 20 chromosomes. As another example, a diploid nuclear genome comprising 20 chromosomes is doubled to become a tetraploid nuclear genome comprising 40 chromosomes. Confirmation of chromosome doubling can be carried out by FISH or other molecular biology techniques known in the art.

In one aspect, a haploid plant provided herein undergoes spontaneous chromosome doubling. Spontaneous chromosome doubling can produce diploid sectors that give rise to normal diploid floral structures. Such spontaneously doubled sectors are desirable because diploid floral structures resulting from spontaneous chromosome doubling produce normal eggs and pollen that can be self-pollinated or used to perform crosses with other plants.

Genome Modification/Recombination

In one aspect, the instant disclosure provides methods for modifying a plant genome. As used herein, "modifying" a plant genome refers to the insertion, substitution, deletion, duplication, inversion, or translocation of one or more nucleotides in a plant genome. In one aspect, a genome modification provided herein is a stable modification. A "stable modification" is a modification that is capable of being transferred to the next generation of a cell.

In one aspect, a nuclear genome provided herein is a haploid nuclear genome. In another aspect, a nuclear genome provided herein is a diploid nuclear genome. In yet another aspect, a nuclear genome provided herein is a triploid nuclear genome. In still another aspect, a nuclear genome provided herein is a tetraploid nuclear genome. In one aspect, a nuclear genome provided herein comprises at least 1, 2, 3, 4, 5, 6, 7, 8, 9, or at least 10 supernumerary chromosomes.

As used herein, the term "genomic rearrangement" refers to a translocation, inversion, deletion, or duplication of two or more nucleotides in a genome. As used herein, the term "translocation" refers to a change in position of a chromosomal segment from a first region to a second region on either the same chromosome or to a second chromosome. As used herein, the term "chromosomal segment" refers to at least 2, 5, 50, 100, 250, 500, 1000, 2500, 5000, 10,000, 25,000, 50,000, 100,000, 250,000, 500,000, 1,000,000, 2,500,000, 5,000,000, 10,000,000, 25,000,000, or at least 50,000,000 contiguous nucleotides of a chromosome, a plastid genome, or a mitochondrial genome. In one aspect, a chromosomal segment provided herein comprises at least 1, 2, 3, 4, 5, 6, 7, 8, 9, or at least 10 megaloci. In another aspect, a chromosomal segment provided herein comprises at least 1, 2, 3, 4, 5, 6, 7, 8, 9, or at least 10 genes. As used herein, "gene" refers to a sequence that encodes a protein, or a sequence encoding a non-protein-coding RNA. As used herein, "protein-coding" refers to a polynucleotide encoding for the amino acids of a polypeptide. As used herein, "encoding" refers to a polynucleotide that can produce a functional unit (without being limiting, for example, a protein, a microRNA (miRNA), a transfer RNA (tRNA), a ribosomal RNA (rRNA), a small interfering RNA (siRNA), a trans-acting small interfering RNA (ta-siRNA), a guide RNA (gRNA), a tracer RNA (tcRNA), a single-guide RNA (sgRNA)) via transcription and/or translation. Non-limiting examples of non-protein-coding RNAs include a miRNA, a miRNA precursor, a siRNA, a small RNA (18-26 nucleotides in length) and precursor encoding the same, a heterochromatic siRNA (hcRNA), a Piwi-interacting RNA (piRNA), a hairpin double-stranded RNA, a naturally occurring antisense siRNA (nat-siRNA), a tcRNA, a gRNA, and a sgRNA.

As used herein, "megalocus" (or the plural form, "megaloci") refers to a block of genetically linked transgenic traits, native traits, or a combination thereof, that are normally inherited as a single unit. A megalocus according to the instant disclosure may provide to a plant one or more desired traits, which may include, but are not limited to, enhanced growth, enhanced yield, drought tolerance, salt tolerance, herbicide tolerance, insect resistance, pest resistance, disease resistance, enhanced nitrogen utilization and the like. In some aspects, a megalocus comprises at least about 2, 3, 4, 5, 6, 7, 8, 9, 10, 11, 13 or 15 transgenic loci (events) that are physically separated but genetically linked such that they can are inherited as a single unit. Each transgenic locus in a megalocus can be 0.1, 0.2, 0.3, 0.4, 0.5, 0.6, 0.7, 0.8, 0.9, 1, 1.5, 2, 2.5, 3, 5, 10, 15, or 20 cM apart from one another. In an aspect, at least 1, 2, 3, 4, 5, 6, 7, 8, 9, or 10 megaloci are transferred or translocated from an HI line, a supernumerary chromosome, or both to a genome of a recipient line. Without being limiting, the transfer or translocation of a megalocus from an HI line or supernumerary chromosome to a recipient line can be confirmed by sequence (e.g., Sanger, 454, Illumina, Pac-Bio) analysis; molecular marker analysis (e.g., FISH, PCR, ELISA, DART); or any applicable molecular biology method known to those skilled in the art. Phenotypic analysis can also be used to confirm the transfer or translocation of a megalocus from an HI line or a supernumerary chromosome to a recipient line. For example, if a transferred or translocated megalocus comprises an herbicide tolerance trait, the application of the herbicide can be used to confirm the presence of the megalocus.

In one aspect, a translocation provided herein is an intrachromosomal translocation. As used herein, an "intrachromosomal translocation" refers to the translocation of a chromosomal segment from a first locus to a second locus within the same chromosome. In another aspect, a translocation provided herein is an interchromosomal translocation. As used herein, an "interchromosomal translocation" refers to the translocation of a chromosomal segment from a first locus on a first chromosome to a second locus on a second chromosome. In another aspect, a translocation provided herein translocates a chromosomal segment from a paternal chromosome or genome to a maternal chromosome or genome. In a further aspect, a translocation provided herein translocates a chromosomal segment from a maternal chromosome or genome to a paternal chromosome or genome. In yet another aspect, a translocation provided herein translocates a chromosomal segment from a mitochondrial or plastid genome to a nuclear genome. In a further aspect, a translocation provided herein translocates a chromosomal segment from a nuclear genome to a mitochondrial or plastid genome. In one aspect, a translocation provided herein translocates a chromosomal fragment from a supernumerary chromosome to an A chromosome, a plastid genome, or a mitochondrial genome. As used herein, an "A chromosome" refers to any of the normally occurring chromosomes in the nuclear genome of a cell. In another aspect, a translocation provided herein translocates a chromosomal fragment from an A chromosome to a supernumerary chromosome. In still another aspect, a translocation provided herein translocates a chromosomal fragment from a mitochondrial or plastid genome to a supernumerary chromosome.

In one aspect, a genomic rearrangement provided herein is selected from the group consisting of a reciprocal translocation and a non-reciprocal translocation. In one aspect, a genomic rearrangement provided herein is selected from the group consisting of a reciprocal translocation, a non-reciprocal translocation, a Robertsonian translocation, a paracentric inversion, and a pericentric inversion. A reciprocal translocation comprises exchanging acentric fragments of genomic material between two non-homologous chromosomes so that the fragments essentially trade positions. A non-reciprocal translocation comprises a one-way transfer of a chromosomal segment from a first chromosome or genome to a second chromosome or genome. A Robertsonian translocation comprises the translocation of an entire chromosome arm from a first chromosome to a second chromosome and often results in the loss of one or more chromosome arms. A paracentric inversion comprises an inversion of a region of a single chromosome where the centromere is not included in the inverted region. A pericentric inversion comprises an inversion of a region of a single chromosome that includes the centromere in the inverted region.

Skilled artisans can use any relevant molecular biology technique to confirm the presence of a modified genome. For example, without being limiting, haploid plants, seeds, or cells can be identified via sequence (e.g., Sanger, 454, Illumina, Pac-Bio) analysis; ELISA; FISH; DNA mismatch analysis using Cell or a similar enzyme; or high resolution melting curve analysis of PCR amplicons containing the modified sequence.

In one aspect, a genomic rearrangement provided herein is effected by one or more GECs provided herein.

As used herein, the term "recombination" refers to the exchange of nucleotides between two nucleic acid molecules. The term "homologous recombination" (HR) refers to the exchange of nucleotides at a conserved region shared by two nucleic acid molecules. HR includes symmetric homologous recombination and asymmetric homologous recombination. Asymmetric homologous recombination can also mean unequal recombination. As used herein, "non-homologous end joining" (NHEJ) refers to the ligation of two ends of double-stranded DNA without the need of a homologous sequence to direct the ligation. Modification of a plant genome provided herein can comprise HR or NHEJ.

Gene Editing Components

As used herein, a "Gene Editing Component (GEC)" refers to an enzyme and/or a donor polynucleotide template capable of eliciting a genome modification. In one aspect, a GEC provided herein elicits a targeted genome modification. In another aspect, a GEC provided herein elicits a non-targeted genome modification. As used herein, "targeted genome modification" refers to the use of site-specific enzymes to direct the editing of a pre-determined, targeted polynucleotide sequence. In one aspect, a GEC provided herein comprises 0, 1, 2, 3, 4, 5, 6, 7, 8, 9, or 10 or more enzymes; 0, 1, 2, 3, 4, 5, 6, 7, 8, 9, or 10 or more donor polynucleotide templates; or both that are capable of eliciting a modification in a plant genome. In one aspect, a plant, a plant cell, or a plant genome provided herein comprises at least 1, 2, 3, 4, 5, 6, 7, 8, 9, or at least 10 GECs. In another aspect, a pollen cell provided herein comprises at least 1, 2, 3, 4, 5, 6, 7, 8, 9, or at least 10 GECs. In another aspect, a plant egg cell provided herein comprises at least 1, 2, 3, 4, 5, 6, 7, 8, 9, or at least 10 GECs. In one aspect, an HI plant provided herein comprises at least 1, 2, 3, 4, 5, 6, 7, 8, 9, or at least 10 GECs. In another aspect, a plant genome provided herein is modified by 1, 2, 3, 4, 5, 6, 7, 8, 9, or 10 or more GECs. In one aspect, the instant disclosure provides 1, 2, 3, 4, 5, 6, 7, 8, 9, or 10 or more nucleic acids encoding a GEC. In one aspect, a GEC provided herein comprises 1, 2, 3, 4, 5, 6, 7, 8, 9, or 10 or more site-specific enzymes. In another aspect, a GEC provided herein comprises a nucleic acid sequence encoding 1, 2, 3, 4, 5, 6, 7, 8, 9, or 10 or more site-specific enzymes. In one aspect, a GEC provided herein comprises a nucleic acid sequence encoding 1, 2, 3, 4, 5, 6, 7, 8, 9, or 10 or more donor polynucleotide templates. As used herein, a "donor polynucleotide template" refers to a polynucleotide that comprises a desired polynucleotide sequence to be inserted into a genome of a recipient line.

In one aspect, the Genome Editing Component in the present disclosure comprises at least one viral replicon. Viral replicon systems have been developed that are based on RNA viruses. Viral replicon systems comprise two essential components: a replicase gene and the target sequence(s) of the replicase protein. The replicase gene product ("replicase protein") acts on the target sequence(s) to amplify the target sequences and any associated sequences, collectively referred to as the replicon. A replicon precursor may be stably inserted into a genome in a manner that allows replicon formation and amplification to be subsequently activated. In an aspect, a viral replicon precursor provided herein comprises at least one nucleic acid sequence encoding at least one replicase gene, at least one target sequence of a replicase gene product, and at least one GEC; when expressed or amplified, this nucleic acid sequence is referred to as a "replicon." A replicase protein can bind to target sequences of a replicon, thereby generating additional replicons. At least one replicase gene is included on the sequence to be amplified in addition to the at least one GEC so that additional copies of the replicase protein are produced. The production of additional copies of the replicon and replicase protein allow replicons to persist over multiple cellular divisions, although known replicons do not persist throughout the entire life cycle of a plant. Because replicons are not physically located on a chromosome, they may persist in cells following the loss of a paternal or maternal nuclear genome following fertilization of an egg cell by a pollen cell. In one aspect, a plant cell provided herein comprises 1, 2, 3, 4, 5, 6, 7, 8, 9, or 10 or more viral replicons after loss of a paternal nuclear genome or a maternal nuclear genome. In another aspect, a replicon provided herein is present in a nucleus of a cell. In yet another aspect, a replicon provided herein is present in a cytoplasm of a cell.

A viral replicon provided herein is operably linked to a promoter that is used to drive replicase expression, subsequent replicon formation, and amplification. In an aspect, an HI plant comprising one or more viral replicons is crossed to a non-HI plant, where one or more replicons are present before, during, or after fertilization. In one aspect, this disclosure provides a transformation construct comprising a selectable marker and a viral replicon.

In one aspect, a genome provided herein comprises 0, 1, 2, 3, 4, 5, 6, 7, 8, 9, or 10 or more viral replicons. In another aspect, a genome provided herein comprises a nucleic acid sequence encoding 0, 1, 2, 3, 4, 5, 6, 7, 8, 9, or 10 or more viral replicons. In one aspect, a genome provided herein comprises multiple viral replicons positioned at multiple loci within the genome. In another aspect, a genome provided herein comprises multiple viral replicons positioned at one locus within the genome. In one aspect, a viral replicon provided herein is amplified in a plant cell upon release from its host genome.

In an aspect, a viral replicon provided herein is a geminivirus replicon or a nanovirus replicon. In the case of a geminivirus replicon system, the precursor comprises two target sequences, called LIRs (NVRs in nanovirus replicon systems), direct orientation that can be acted upon by a replicase protein to create a replicon comprising an LIR and any sequence present between the two LIRs. Nanovirus replicon systems work in a similar manner to geminivirus replicon systems. Alternatively, a replicon can be generated by flanking a single copy of a replicase target sequence (e.g., LIR, NVR) and one or more GECs with a pair of site-specific recombinase target sequences. When the appropriate recombinase is provided it excises a circular DNA molecule that can be replicated by a replicase protein that recognizes the replicase target sequence.

In one aspect, a GEC provided herein modifies a plant genome. In another aspect, a GEC provided herein modifies a plant genome selected from the group consisting of a nuclear genome, a mitochondrial genome, and a plastid genome. In another aspect, a GEC provided herein modifies a maternal plant genome or a paternal plant genome. In one aspect, a nucleic acid sequence encoding a GEC provided herein is positioned in a maternal genome. In another aspect, a nucleic acid sequence encoding a GEC provided herein is positioned in a paternal genome. In one aspect, a GEC provided herein does not elicit a modification in a genome of an HI plant or cell. In another aspect, a GEC provided herein does elicit a modification in a genome of an HI plant or cell provided that the modification is not lethal to the HI plant or cell.

In an aspect, a donor polynucleotide template provided herein is flanked by nucleic acid sequences that are at least 80%, 85%, 90%, 91%, 92%, 93%, 94%, 95%, 96%, 97%, 98%, 99%, or 100% identical to a target site in a recipient line. As used herein, a "recipient line" refers to a plant line or variety comprising a genome that is to be edited.

In one aspect, a donor polynucleotide template provided herein is inserted from an HI line genome into a corresponding genomic region in a recipient line. In another aspect, a donor polynucleotide template provided herein is inserted from an HI line genome into a non-targeted genomic region in a recipient line. In one aspect, a donor polynucleotide template provided herein is present in 2, 3, 4, 5, 6, 7, 8, 9, or 10 or more copies in an HI line genome.

In one aspect, a donor polynucleotide template that is at least 80%, 85%, 90%, 91%, 92%, 93%, 94%, 95%, 96%, 97%, 98%, 99%, 99.5%, or at least 99.9% identical to a targeted genomic sequence of interest. As used herein, a "targeted genomic sequence of interest" refers to a nucleic acid sequence in a genome that is capable of being edited by a site-specific enzyme. In an aspect, a donor polynucleotide template provided herein is 100% identical to a targeted genomic sequence of interest except for a desired modification. A desired modification can comprise the insertion, deletion, duplication, substitution, or inversion of at least 1, 2, 5, 10, 25, 50, 100, 250, 500, 1000, 2500, 5000, or at least 10,000 nucleotides compared to the unmodified state of the locus. In one aspect, a donor polynucleotide template comprises an endogenous allele of a targeted genomic sequence of interest. In another aspect, a donor polynucleotide template provided herein is an exogenous nucleic acid sequence. In another aspect, a donor polynucleotide template provided herein comprises a transgene. In one aspect, a donor polynucleotide template modifies at least 1, 2, 3, 4, 5, 6, 7, 8, 9, or at least 10 targeted genomic sequences of interest.

Types of Enzymes

In one aspect, an enzyme provided herein is a site-specific enzyme. As used herein, a "site-specific enzyme" refers to any enzyme that can cleave a nucleotide sequence in a site-specific manner. In an aspect, a site-specific enzyme provided herein is selected from the group consisting of an endonuclease (without being limiting, for example, a meganuclease, a zinc-finger nuclease (ZFN), a transcription activator-like effector nuclease (TALEN), an RNA-guided nuclease (without being limiting, for example, a clustered regularly interspaced short palindromic repeats (CRISPR) Cas9 nuclease, or a Cpf1 nuclease); a recombinase (without being limiting, for example, a serine recombinase attached to a DNA recognition motif, a tyrosine recombinase attached to a DNA recognition motif); a transposase (without being limiting, for example, a DNA transposase attached to a DNA binding domain); or any combination thereof.

In one aspect, a site-specific enzyme provided herein recognizes and binds to and/or cleaves a nucleic acid sequence flanking a sequence selected from the group consisting of a targeted genomic sequence of interest, a megalocus, a donor polynucleotide template, an endogenous gene, or a transgene.

In one aspect a site-specific enzyme provided herein is selected from the group consisting of a recombinase, an endonuclease, and a transposase.

In one aspect, a recombinase provided herein is a tyrosine recombinase attached to a DNA recognition motif or a serine recombinase attached to a DNA recognition motif. As used herein, a "DNA binding domain" or a "DNA recognition motif" is a polypeptide domain that is capable of recognizing and/or binding to specific sequences of single stranded and/or double stranded DNA. In one aspect, a tyrosine recombinase attached to a DNA recognition motif provided herein is selected from the group consisting of a Cre recombinase, a Gin recombinase, a FLP recombinase, and a Tnp1 recombinase. In another aspect, a Cre recombinase or a Gin recombinase provided herein is tethered to a zinc-finger DNA biding domain. In one aspect, a serine recombinase attached to a DNA recognition motif provided herein is selected from the group consisting of a Bxb1 integrase, a phiC31 integrase, an R4 integrase, and a TP-901 integrase. In one aspect, a recombinase provided herein is tethered or otherwise attached to a DNA recognition motif.

Site-specific endonucleases (e.g., meganucleases, ZFNs, TALENs, Cas9 nucleases, Cpf1 nucleases) induce a double-strand DNA break at the target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of nucleic acid sequences by HR.

In one aspect, an endonuclease provided herein is selected from the group consisting of a CRISPR-associated nuclease, a TALEN, a TALE-like protein, a zinc finger nuclease, and a meganuclease.

In an aspect, a site-specific endonuclease provided herein is a zinc finger nuclease. Zinc finger nucleases are synthetic proteins consisting of an engineered zinc finger DNA-binding domain fused to the cleavage domain of the Fold restriction endonuclease. Zinc finger nucleases can be designed to cleave almost any long stretch of double-stranded DNA for modification of the zinc finger DNA-binding domain. Zinc finger nucleases form dimers from monomers composed of a non-specific DNA cleavage domain of Fold endonuclease fused to a zinc finger array engineered to bind a target DNA sequence. The Fold nuclease domain requires dimerization to cleave DNA and therefore two zinc finger nucleases with their C-terminal regions are needed to bind opposite DNA strands of the cleavage site (separated by 5-7 bp).

The DNA-binding domain of a zinc finger nuclease is typically composed of 3-4 zinc-finger arrays. The amino acids at positions −1, +2, +3, and +6 relative to the start of the zinc finger Go-helix, which contribute to site-specific binding to the target DNA, can be changed and customized to fit specific target sequences. The other amino acids form the consensus backbone to generate zinc finger nucleases with different sequence specificities. Rules for selecting target sequences for zinc finger nucleases are known in the art. A zinc finger nuclease monomer can cut the target site if the two-zinc finger-binding sites are palindromic. The term "zinc finger nuclease", as used herein, is broad and includes a monomeric zinc finger nuclease that can cleave double stranded DNA without assistance from another zinc finger nuclease. The term "zinc finger nuclease" is also used to refer to one or both members of a pair of zinc finger nucleases that are engineered to work together to cleave DNA at the same site.

Because the DNA-binding specificities of zinc finger domains can in principle be re-engineered using one of various methods, customized zinc finger nucleases can theoretically be constructed to target nearly any gene sequence. Publicly available methods for engineering zinc finger domains include Context-dependent Assembly (CoDA), Oligomerized Pool Engineering (OPEN), and Modular Assembly.

In an aspect, a site-specific endonuclease provided herein is a TALEN or TALE-like nuclease. TALENs are artificial restriction enzymes generated by fusing the transcription activator-like effector DNA binding domain to a nuclease domain. In some embodiments, the nuclease domain of a TALEN or TALE-like nuclease provided herein is selected from a group consisting of PvuII, MutH, TevI and Fold. When each member of a TALEN pair binds to the DNA sites flanking a target site, the nuclease domain monomers (e.g., FokI) dimerize and cause a double-stranded DNA break at the target site. The term "TALEN," as used herein, is broad and includes a monomeric TALEN that can cleave double stranded DNA without assistance from another TALEN. The term "TALEN" is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The Fold domain functions as a dimer, requiring two constructs with unique DNA binding domains for sites in the target genome with proper orientation and spacing. Both the number of amino acid residues between the TALEN DNA binding domain and the Fold cleavage domain and the number of bases between the two individual TALEN binding sites are parameters for achieving high levels of activity. PvuII, MutH, and TevI cleavage domains are useful alternatives to Fold and FokI variants for use with TALEs. PvuII functions as a highly specific cleavage domain when coupled to a TALE (see Yank et al. 2013. PLoS One. 8: e82539). MutH is capable of introducing strand-specific nicks in DNA (see Gabsalilow et al. 2013. Nucleic Acids Research. 41: e83). TevI introduces double-stranded breaks in DNA at targeted sites (see Beurdeley et al., 2013. Nature Communications. 4: 1762).

The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., Nucleic Acids Research (2012) 40: W117-122; Cermak et al., Nucleic Acids Research (2011). 39:e82; and tale-nt.cac.cornell.edu/about.

In an aspect, a site-specific endonuclease provided herein is a meganuclease. Meganucleases, which are commonly identified in microbes, are unique enzymes with high activity and long recognition sequences (>14 bp) resulting in site-specific digestion of target DNA. Engineered versions of naturally occurring meganucleases typically have extended DNA recognition sequences (e.g., 14 to 40 bp).

The engineering of meganucleases is more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

In an aspect, a site-specific endonuclease provided herein comprises a Cas9 or Cpf1 nuclease. In another aspect, a site-specific endonuclease provided herein comprises any combination of an RNA-guided Cas9 nuclease or an RNA-guided Cpf1 nuclease; CRISPR-associated proteins Csc1 and Csc2; Cas6, Cas6e, and Cas6f; and a guide RNA necessary for targeting the respective nucleases.

Cas9 nucleases are part of the adaptive immune system of bacteria and archaea, protecting them against invading nucleic acids such as viruses by cleaving the foreign DNA in a sequence-dependent manner. The immunity is acquired by the integration of short fragments of the invading DNA known as spacers between two adjacent repeats at the proximal end of a CRISPR locus. The CRISPR arrays, including the spacers, are transcribed during subsequent encounters with invasive DNA and are processed into small interfering CRISPR RNAs (crRNAs) approximately 40 nt in length, which combine with the trans-activating CRISPR RNA (tracrRNA) to activate and guide the Cas9 nuclease. This cleaves homologous double-stranded DNA sequences known as protospacers in the invading DNA. A prerequisite for cleavage is the presence of a conserved protospacer-adjacent motif (PAM) downstream of the target DNA, which usually has the sequence 5-NGG-3 but less frequently NAG. Specificity is provided by the so-called "seed sequence" approximately 12 bases upstream of the PAM, which must match between the RNA and target DNA. Cpf1 acts in a similar manner to Cas9, but Cpf1 does not require a tracrRNA.

Non-limiting examples of site-specific transposases provided herein include any DNA transposase attached to a DNA binding domain, such as a TALE-piggyBac of TALE-Mutator.

Promoters

In one aspect, the Genome Editing Component in the present disclosure comprises at least one promoter.

A "promoter" contains a sequence of nucleotide bases that signals RNA polymerase to associate with the DNA and to initiate transcription into mRNA using one of the DNA strands as a template to make a corresponding complementary strand of RNA. In one aspect, a promoter provided herein is operably linked to DNA encoding at least 1, 2, 3, 4, 5, 6, 7, 8, 9, or at least 10 GECs. As used herein, "operably linked" means that the operably linked nucleic acid sequences exhibit their desired function. For example, in an aspect of this disclosure, a provided DNA promoter sequence can initiate transcription of an operably linked DNA sequence into RNA. A nucleic acid sequence provided herein can be upstream or downstream of a physically or operably linked nucleic acid sequence. In an aspect, a first nucleic acid molecule provided herein is both physically linked and operably linked to a second nucleic acid molecule provided herein. In another aspect, a first nucleic acid molecule provided herein is neither physically linked nor operably linked to a second nucleic acid molecule provided herein. As used herein, "upstream" means the nucleic acid sequence is positioned before the 5' end of a linked nucleic acid sequence. As used herein, "downstream" means the nucleic acid sequence is positioned after the 3' end of a linked nucleic acid sequence.

In one aspect, a GEC provided herein is operably linked to at least one promoter. In another aspect, a nucleic acid molecule encoding a GEC is transiently expressed. As used herein, "transiently expressed" refers to temporally restricted expression. In yet another aspect, a nucleic acid molecule encoding a GEC provided herein is constitutively expressed.

In one aspect, a promoter provided herein is selected from the group consisting of a constitutive promoter, an inducible promoter, and a tissue-specific promoter. In another aspect, a promoter provided herein is a constitutive promoter. In another aspect, a promoter provided herein is an inducible promoter. In another aspect, a promoter provided herein is a tissue-specific promoter. In one aspect, a tissue-specific promoter provided herein is selected from the group consisting of an embryo-specific promoter, a gamete-specific promoter, and an early zygote-specific promoter. In a one aspect, a promoter provided herein is functional in a zygote at the time of the first cellular division following fertilization of an ovule by a pollen grain. In one aspect, a promoter provided herein is functional in a pollen cell or an egg cell within 48 hours of fertilization.

A number of promoters that are active in plant cells have been described in the literature. Such promoters include, but are not limited to, the nopaline synthase (NOS) and octopine synthase (OCS) promoters that are carried on Ti plasmids of *Agrobacterium tumefaciens*, the caulimovirus promoters such as the cauliflower mosaic virus (CaMV) 19S and 35S promoters, the Figwort mosaic virus (FMV) 35S promoter, and the enhanced CaMV35S promoter (e35S). A variety of other plant gene promoters that are regulated in response to environmental, hormonal, chemical, and/or developmental signals, also can be used for expression of heterologous genes in plant cells, including, for instance, promoters regulated by (1) heat (Callis et al., Plant Physiology, (1988) 88: 965-968), (2) light (e.g., pea RbcS-3A promoter, Kuhlemeier et al., Plant Cell, (1989) 1: 471-478; maize RbcS promoter, Schaffner et al., Plant Cell (1991) 3: 997-1012); (3) hormones, such as abscisic acid (Marcotte et al., Plant Cell, (1989) 1: 969-976), (4) wounding (e.g., Siebertz et al., Plant Cell, (1989) 961-968); or other signals or chemicals.

In some embodiments, a promoter is capable of causing sufficient expression to result in the production of an effective amount of the gene product of interest. Examples describing such promoters include without limitation U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. patent application Ser. No. 09/757,089 (maize chloroplast aldolase promoter). Additional promoters that can find use are a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., Plant Molecular Biology (1987) 9: 315-324), the CaMV 35S promoter (Odell et al., Nature (1985) 313: 810-812), the figwort mosaic virus 35S-promoter (U.S. Pat. Nos. 6,051,753; 5,378,619), the sucrose synthase promoter (Yang and Russell, Proceedings of the National Academy of Sciences, USA (1990) 87: 4144-4148), the R gene complex promoter (Chandler et al., Plant Cell (1989) 1: 1175-1183), and the chlorophyll a/b binding protein gene promoter, PC1SV (U.S. Pat. No. 5,850, 019), and AGRtu.nos (GenBank Accession V00087; Depicker et al., Journal of Molecular and Applied Genetics (1982) 1: 561-573; Bevan et al., 1983) promoters.

In some embodiments, promoter hybrids can be constructed to enhance transcriptional activity (U.S. Pat. No. 5,106,739), or to combine desired transcriptional activity, inducibility and tissue specificity or developmental specificity. Promoters that function in plants include but are not limited to promoters that are inducible, viral, synthetic, constitutive, temporally regulated, spatially regulated, and spatio-temporally regulated. Other promoters that are tissue-enhanced, tissue-specific, or developmentally regulated are also known in the art and envisioned to have utility in the practice of this disclosure.

Promoters used in the provided nucleic acid molecules and vectors of this disclosure can be modified, if desired, to affect their control characteristics. Promoters can be derived by means of ligation with operator regions, random or controlled mutagenesis, etc. Furthermore, the promoters can be altered to contain multiple "enhancer sequences" to assist in elevating gene expression.

Without being limiting, exemplary constitutive promoters include the core promoter of the Rsyn7 promoter and other constitutive promoters disclosed in U.S. Pat. No. 6,072,050; the core CaMV 35S promoter (Odell et al. (1985) Nature 313:810-812); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J 3:2723-2730); ALS promoter (U.S. Pat. No. 5,659, 026), and the like.

Without being limiting, exemplary chemical-inducible promoters include the tobacco PR-la promoter, which is activated by salicylic acid. Other chemical-inducible promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible promoters (see, for example, Gatz et al. (1991) Mol. Gen. Genet. 227:229-237, and U.S. Pat. Nos. 5,814,618 and 5,789,156). Additional exemplary promoters that can be used herein are those responsible for heat-regulated gene expression, light-regulated gene expression (for example, the pea rbcS-3A; the maize rbcS promoter; the chlorophyll alb-binding protein gene found in pea; or the Arabssu promoter), hormone-regulated gene expression (for example, the abscisic acid (ABA) responsive sequences from the Em gene of wheat; the ABA-inducible HVA1 and HVA22, and rd29A promoters of barley and Arabidopsis; and wound-induced gene expression (for example, of wunl), organ specific gene expression (for example, of the tuber-specific storage protein gene; the 23-kDa zein gene from maize described by; or the French bean (β-phaseolin gene), or pathogen-inducible promoters (for example, the PR-1, prp-1, or (β-1,3 glucanase promoters, the fungal-inducible wirla promoter of wheat, and the nematode-inducible promoters, TobRB7-5A and Hmg-1, of tobacco arid parsley, respectively).

Without being limiting, exemplary tissue-specific promoters include those disclosed in Yamamoto et al. (1997) Plant J. 12(2):255-265; Kawamata et al. (1997) Plant Cell Physiol. 38(7):792-803; Hansen et al. (1997) Mol. Gen. Genet. 254(3):337-343; Russell et al. (1997) Transgenic Res. 6(2): 157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol. Biol. 23(6):1129-1138; Matsuoka et al. (1993) Proc Natl. Acad. Sci. USA 90(20):9586-9590; and Guevara-Garcia et al. (1993) Plant J. 4(3):495-505.

Transformation

Methods of transforming plant cells are well known by persons of ordinary skill in the art. For instance, specific instructions for transforming plant cells by microprojectile bombardment with particles coated with recombinant DNA are found in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153, 812 (wheat); U.S. Pat. No. 6,002,070 (rice); U.S. Pat. No. 7,122,722 (cotton); U.S. Pat. No. 6,051,756 (Brassica); U.S. Pat. No. 6,297,056 (Brassica); US Patent Publication 20040123342 (sugarcane) and Agrobacterium-mediated transformation is described in U.S. Pat. No. 5,159,135 (cotton); U.S. Pat. No. 5,824,877 (soybean); U.S. Pat. No. 5,591,616 (corn); U.S. Pat. No. 6,384,301 (soybean); U.S. Pat. No. 5,750,871 (Brassica); U.S. Pat. No. 5,463,174

(Brassica); and 5,188,958 (Brassica), all of which are incorporated herein by reference. Methods for transforming other plants can be found in, for example, Compendium of Transgenic Crop Plants (2009) Blackwell Publishing. Any appropriate method known to those skilled in the art can be used to transform a plant cell with any of the nucleic acid molecules provided herein.

In one aspect, a plant cell provided herein is stably transformed with at least 1, 2, 3, 4, 5, 6, 7, 8, 9, or at least 10 GECs. As used herein, "stably transformed" refers to a transfer of DNA into a genome of a targeted cell that allows the targeted cell to pass the transferred DNA to the next generation. In another aspect, a plant cell provided herein is transiently transformed with at least 1, 2, 3, 4, 5, 6, 7, 8, 9, or at least 10 GECs. As used herein, "transiently transformed" is defined as a transfer of DNA into a cell that is not integrated into a genome of the transformed cell. In one aspect, a plant capable of inducing haploidization provided herein comprises at least 1, 2, 3, 4, 5, 6, 7, 8, 9, or at least 10 stably transformed GECs. In another aspect, a plant capable of inducing haploidization provided herein comprises at least 1, 2, 3, 4, 5, 6, 7, 8, 9, or at least 10 transiently transformed GECs. In an aspect, a method of transforming a plant cell provided herein comprises a biolistic transformation or a bacteria-mediated transformation. In an aspect, a method of transforming a plant cell provided herein comprises bacteria-mediated transformation that further comprises contacting the plant cell with at least one Agrobacterium cell, where the Agrobacterium cell is capable of transforming the plant cell.

Transformation methods to provide transgenic plant cells and transgenic plants containing stably integrated nucleic acid molecules provided herein are preferably practiced in tissue culture on media and in a controlled environment. As used herein, "media" refers to the numerous nutrient mixtures that are used to grow cells in vitro, that is, outside of the intact living organism.

In one aspect, this disclosure provides plant cells that are not reproductive material and do not mediate the natural reproduction of the plant. In another aspect, this disclosure also provides plant cells that are reproductive material and mediate the natural reproduction of the plant. In another aspect, this disclosure provides plant cells that cannot maintain themselves via photosynthesis. In another aspect, this disclosure provides somatic plant cells. Somatic cells, contrary to germline cells, do not mediate plant reproduction.

Recipient cell targets for transformation include, but are not limited to, a seed cell, a fruit cell, a leaf cell, a cotyledon cell, a hypocotyl cell, a meristem cell, an embryo cell, an endosperm cell, a root cell, a shoot cell, a stem cell, a pod cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, a phloem cell, a bud cell, or a vascular tissue cell. In another aspect, this disclosure provides a plant chloroplast. In a further aspect, this disclosure provides an epidermal cell, a stomata cell, a trichome cell, a root hair cell, a storage root cell, or a tuber cell. In another aspect, this disclosure provides a protoplast. In another aspect, this disclosure provides a plant callus cell. Any cell from which a fertile plant can be regenerated is contemplated as a useful recipient cell for practice of this disclosure. Callus can be initiated from various tissue sources, including, but not limited to, immature embryos or parts of embryos, seedling apical meristems, microspores, and the like. Those cells which are capable of proliferating as callus can serve as recipient cells for transformation.

Practical transformation methods and materials for making transgenic plants of this disclosure (e.g., various media and recipient target cells, transformation of immature embryos, and subsequent regeneration of fertile transgenic plants) are disclosed, for example, in U.S. Pat. Nos. 6,194,636 and 6,232,526 and U. S. Patent Application Publication 2004/0216189.

In one aspect, the instant disclosure provides a plant cell transformed by any method provided herein. In an aspect, a plant cell provided herein is selected from the group consisting of an Acacia cell, an alfalfa cell, an aneth cell, an apple cell, an apricot cell, an artichoke cell, an arugula cell, an asparagus cell, an avocado cell, a banana cell, a barley cell, a bean cell, a beet cell, a blackberry cell, a blueberry cell, a broccoli cell, a Brussels sprout cell, a cabbage cell, a canola cell, a cantaloupe cell, a carrot cell, a cassava cell, a cauliflower cell, a celery cell, a Chinese cabbage cell, a cherry cell, a cilantro cell, a citrus cell, a clementine cell, a coffee cell, a corn cell, a cotton cell, a cucumber cell, a Douglas fir cell, an eggplant cell, an endive cell, an escarole cell, an eucalyptus cell, a fennel cell, a fig cell, a forest tree cell, a gourd cell, a grape cell, a grapefruit cell, a honey dew cell, a jicama cell, kiwifruit cell, a lettuce cell, a leek cell, a lemon cell, a lime cell, a Loblolly pine cell, a mango cell, a maple tree cell, a melon cell, a mushroom cell, a nectarine cell, a nut cell, an oat cell, an okra cell, an onion cell, an orange cell, an ornamental plant cell, a papaya cell, a parsley cell, a pea cell, a peach cell, a peanut cell, a pear cell, a pepper cell, a persimmon cell, a pine cell, a pineapple cell, a plantain cell, a plum cell, a pomegranate cell, a poplar cell, a potato cell, a pumpkin cell, a quince cell, a radiata pine cell, a radicchio cell, a radish cell, a rapeseed cell, a raspberry cell, a rice cell, a rye cell, a sorghum cell, a Southern pine cell, a soybean cell, a spinach cell, a squash cell, a strawberry cell, a sugar beet cell, a sugarcane cell, a sunflower cell, a sweet corn cell, a sweet potato cell, a sweetgum cell, a tangerine cell, a tea cell, a tobacco cell, a tomato cell, a turf cell, a vine cell, watermelon cell, a wheat cell, a yam cell, and a zucchini cell. In another aspect, a plant cell provided herein is selected from the group consisting of a corn or maize cell, a soybean cell, a canola cell, a cotton cell, a wheat cell, and a sugarcane cell.

In another aspect, a plant cell provided herein is selected from the group consisting of a corn immature embryo cell, a corn mature embryo cell, a corn seed cell, a soybean immature embryo cell, a soybean mature embryo cell, a soybean seed cell, a canola immature embryo cell, a canola mature embryo cell, a canola seed cell, a cotton immature embryo cell, a cotton mature embryo cell, a cotton seed cell, a wheat immature embryo cell, a wheat mature embryo cell, a wheat seed cell, a sugarcane immature embryo cell, a sugarcane mature embryo cell, a sugarcane seed cell.

In one aspect, transformation of a plant cell is performed by an Agrobacterium-mediated method (U.S. Pat. Nos. 6,265,638, 5,731,179; U.S. Patent Application Publications 2005/0183170; 2003/110532). The DNA constructs used for transformation in the methods of present disclosure generally also contain plasmid backbone DNA segments that provide replication function and antibiotic selection in bacterial cells, for example, an Escherichia coli origin of replication such as ori322, an Agrobacterium origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tume-*

*faciens* ABI, C58, LBA4404, AGLO, AGL1, EHA101, or EHA105 carrying a plasmid having a transfer function for the expression unit. Other strains known to those skilled in the art of plant transformation can function in this disclosure.

To confirm the presence of integrated DNA in a transformed cell or genome a variety of assays can be performed. Such assays include, for example, molecular biological assays (e.g., Southern and northern blotting, PCR™); biochemical assays, such as detecting the presence of a protein product (e.g., by immunological means (ELISAs and western blots), or by enzymatic function (e.g., GUS assay)); pollen histochemistry; plant part assays, (e.g., leaf or root assays); and also, by analyzing the phenotype of the whole regenerated plant.

The instant disclosure also provides a transgenic plant cell comprising a sequence of interest integrated into a genome of the plant cell according to the methods disclosed herein. Also provided is a transgenic plant produced by the methods disclosed herein.

B Chromosomes

As used herein, the term "supernumerary chromosome" refers to an extra chromosome found in addition to the normal complement of A chromosomes. In one aspect, a HI line provided herein comprises at least 1, 2, 3, 4, 5, 6, 7, 8, 9, or at least 10 supernumerary chromosomes. In another aspect, a recipient line provided herein comprises at least 1, 2, 3, 4, 5, 6, 7, 8, 9, or at least 10 supernumerary chromosomes. In one aspect, a supernumerary chromosome provided herein is a B chromosome. In another aspect, a supernumerary chromosome provided herein is an artificially derived chromosome. In yet another aspect, an artificially derived chromosome provided herein is a truncated chromosome or a de novo generated chromosome.

In an aspect, a B chromosome provided herein is a maize B chromosome. In another aspect, a B chromosome provided herein is a rye B chromosome. In an aspect, a B chromosome provided herein is a *Tripsacum* B chromosome. B chromosomes are found in addition to the normal diploid complement of chromosomes in a cell. For example, in maize, the normal diploid complement of chromosomes is 20. B chromosomes are dispensable and are not required for normal plant development. When two B chromosomes are present in a single plant, the two B chromosomes can pair with each other at meiotic prophase and recombination can occur. B chromosomes do not pair with or recombine with A chromosomes.

In one aspect, a method provided herein comprises the incorporation of a DNA of interest into a supernumerary chromosome. In another aspect, a method provided herein comprises the modification at least one locus on a supernumerary chromosome. In another aspect, a method provided herein comprises the translocation of a nucleic acid molecule from a supernumerary chromosome to an A chromosome, a plastid genome, or a mitochondrial genome.

In one aspect, a supernumerary chromosome provided herein comprises at least 1, 2, 3, 4, 5, 6, 7, 8, 9, or at least 10 GECs. In one aspect, a supernumerary chromosome provided herein comprises at least 1, 2, 3, 4, 5, 6, 7, 8, 9, or at least 10 donor polynucleotide templates. In one aspect, a supernumerary chromosome provided herein comprises at least 1, 2, 3, 4, 5, 6, 7, 8, 9, or at least 10 site-specific enzymes. In yet another aspect, a supernumerary chromosome provided herein comprises at least 1, 2, 3, 4, 5, 6, 7, 8, 9, or at least 10 megaloci. In one aspect, a supernumerary chromosome provided herein comprises at least 1, 2, 3, 4, 5, 6, 7, 8, 9, or at least 10 transgenes. In another aspect, a supernumerary chromosome provided herein is bound and/or cleaved by a site-specific enzyme.

In one aspect, a GEC positioned on an A chromosome, a mitochondrial genome, or a plastid (e.g., chloroplast) genome provided herein modifies at least one nucleic acid sequence of a supernumerary chromosome. In another aspect, a GEC positioned on a supernumerary chromosome provided herein modifies at least one nucleic acid of an A chromosome, a mitochondrial genome, or a plastid (e.g., chloroplast) genome.

In one aspect, a cell comprising a supernumerary chromosome provided herein is subjected to irradiation to generate 1, 2, 3, 4, 5, 6, 7, 8, 9, or 10 or more genomic rearrangements.

In an aspect, a supernumerary chromosome provided herein is a B-A chromosome or an A-B chromosome. B-A and A-B chromosomes result from reciprocal translocations between normal A chromosomes and supernumerary B chromosomes in corn. A B-A translocation results in a B-A chromosome and an A-B chromosome, with the second listed chromosome denoting the chromosome arm without its native centromere. For example, a 9S-B chromosome comprises a B chromosome arm attached to a normal short arm of chromosome 9 and the chromosome 9 centromere; the reciprocal B-9L chromosome comprises a B chromosome arm and centromere attached to the long arm of normal chromosome 9. B-A and A-B chromosomes can meiotically recombine with corresponding normal A chromosomes. As a non-limiting example, a 9S-B chromosome can meiotically recombine with the short arm of normal chromosome 9.

In one aspect, a megalocus provided herein is positioned on a B-A or an A-B chromosome. In another aspect, a transgene provided herein is positioned on a B-A or an A-B chromosome. In yet another aspect, a GEC provided herein is positioned on a B-A or an A-B chromosome. In one aspect, a donor polynucleotide template provided herein is positioned on a B-A or an A-B chromosome. In yet another aspect, a site-specific enzyme provided herein is positioned on a B-A or an A-B chromosome.

In one aspect, this disclosure provides a method of translocating a megalocus, transgene, or GEC from a B-A or an A-B chromosome to a corresponding normal chromosome via meiotic recombination.

One or more B chromosomes, according to certain aspects of the present disclosure, can be delivered to a progeny plant without the rest of the paternal or maternal genome (e.g., via a haploid induction cross that retains the B chromosome), allowing complete conversion to a new variety in a single cross. In another aspect, a B chromosome may be transferred from a first plant species to a second plant species, allowing testing of the transgene or transgenes in other crops. For example, transmission of a B chromosome to oat has been demonstrated, as well as transmission of a corn chromosome to wheat (Koo et al., Genome Research 21(6):908-914, 2011; Comeau et al., Plant Science 81(1):117-125, 1992).

In certain cases, such as in corn and rye, B chromosomes have "accumulation mechanisms" that allow them to transmit at greater than Mendelian frequencies. For example, in corn, the sister chromatids of the B chromosome fail to separate during the second pollen (first generative) division. As a result, both sister chromatids are delivered to one of the sperm, while the other receives neither. This effect, called non-disjunction, means that a plant with only a single B chromosome can deliver zero, one, or two B chromosomes to the next generation when used as a male. Such an effect may be desirable during the trait introgression process, since it allows individuals that are homozygous (as opposed to hemizygous) for a megalocus carried on a B chromosome to be recovered in a backcross, as long as the B chromosome is delivered from the pollen.

The non-disjunction effect requires that specific portions of the B chromosome be present. A trans-acting piece at the tip of the long arm and a cis-acting piece near the centromere are required. Very small deletions at the tip of the long arm of the B chromosome are recoverable and the resulting B chromosomes do not exhibit non-disjunction. In certain embodiments of the disclosure, such a deletion variant of the B chromosome may be desired, for instance, for the purpose of delivering a megalocus for commercial traits. In an aspect, a supernumerary chromosome provided herein undergoes non-disjunction.

Crossing

Certain aspects of these methods comprise "crossing" one parent plant with another to create progeny plants. Crossing also includes "selfing" in which the same plant (or a genetically similar relative) is used as both the male and female parent. Those of ordinary skill in the art will also understand that various different types of crosses may be employed herein, often depending on the types of parent(s) selected, to create a cross. Other manners of complex crossing schemes known in the art may further be used to create a population of crosses, including, for example, 3-way crosses, 4-way crosses, 5-way crosses, etc., within and among different groups of hybrids, inbreds, heterotic designations, races, ploidy levels (e.g., haploids, diploids, doubled-haploids, triploids, polyploids, etc.), species, etc. In addition, a variety of different manners of creating offspring between two plants or plant cells may also be used in connection with creating progeny cells.

In certain aspects, a cross is made when pollen makes contact the female reproductive structures (e.g. the stigma, pollen tube, megagametophyte, ovule, etc.). In certain aspects, the result of making a cross is to produce a progeny zygote cell. The zygote cell need not contain genetic material from both parents, for example, a progeny plant produced from a cross with a haploid inducer line may not contain DNA inherited from the inducer parent, yet a progeny plant cell produced from such methods are still considered progeny of the inducer parent.

One aspect of this invention is that the GEC is brought close enough to the target genome that the products it encodes are able to act upon a target genome that is nearby. For instance, examples of the methods described herein explain how this may be accomplished by fertilization and/or syngamy to deliver a GEC contained in a sperm cell into the nucleus of an egg cell where a genome that a user wishes to edit resides. One can easily understand that expression of a GEC in the same nucleus as a target genome can result in a desired edit. However, it is also known in the art that the products of GEC transcription and/or translation can be transported across membranes, so that the GEC need not make it all the way inside of the same nucleus as the target genome for the products it encodes to diffuse, and/or be transported, or otherwise migrate across the nuclear envelope to the target genome where they can then create a desired edit. Furthermore, it is even possible that the GEC is not expressed in the same cell as a target genome, as it is also known in the art that the products of transcription and/or translation can diffuse, migrate, and/or be transported across a cell membrane and into a cell, and from there, across the nuclear envelope to create a desired edit in a target genome.

Certain aspects of the methods disclosed herein include making crosses between types of plants whose genomes are known to not persist in the cells of the progeny and/or whose genomes are known to recombine very little or not at all with the genome of another parent in the progeny, or not at all, during the time that the two genomes do persist in the same cell of the progeny. For instance, polyploid varieties of soybean have been described (Beversdorf W D. (1979) Can J Plant Sci. 59:945-948), so it is anticipated that instead of using a maize haploid inducer genome as a carrier chromosome, for example, one could place a GEC in the genome of a diploid soybean and then cross that plant to a tetraploid soybean plant in order to make a desired edit in a genome of the tetraploid soybean plant. Crossing the two plants will produce triploid offspring; one genome inherited from the diploid parent that contains the GEC, and two genomes inherited form the tetraploid parent, one or both of which could be targets for the GEC. The two genomes will exist within editing distance of one another (e.g. in the same cell) for long enough that the GEC makes the desired edit, but since it is known in the art that the genome inherited from the diploid parent in a 2××4× cross is soon eliminated in the offspring, one can understand that the GEC on a chromosome of the 2× parent would also be eliminated, and that it would be possible to eventually recover diploid progeny that contained only the genomes inherited from the tetraploid parent, at least one of which contains the desired edit. Depending on the nature of the edit, and the homology between genomes, the desired edit may be made in one or both of the genomes inherited from the tetraploid parent. It is anticipated that with this disclosure, plant breeders will now recognize how this idea is not limited to diploid and tetraploids, but could be applied to a host of other crosses between plants of differing ploidy levels without altering the fundamental concept of how the chromosome elimination mechanisms of inter-ploidy crosses could be used to bring a GEC within editing distance of a target genome, and/or how this mechanism could be used to remove a GEC from progeny cells.

Thus, a cross, as used herein, is a broad term that includes any situation where a carrier chromosome containing a GEC is brought close enough to a target genome that products expressed by the GEC are capable of creating a desired edit in a target genome. Those of skill in the art will understand that there are methods of extending this distance, but that the principle remains the same.

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. The initial cross gives rise to the F1 generation. The term "BC1" refers to the second use of the recurrent parent, "BC2" refers to the third use of the recurrent parent, and so on. In one aspect, a backcross is performed repeatedly, with a progeny individual of each successive backcross generation being itself backcrossed to the same parental genotype. In one aspect, a plant comprising a modified genome provided herein is backcrossed or self-fertilized to remove a supernumerary chromosome.

As used herein, "elite variety" means any variety that has resulted from breeding and selection for superior agronomic performance.

As used herein, "selecting" or "selection" in the context of breeding refer to the act of picking or choosing desired individuals, normally from a population, based on certain pre-determined criteria.

In one aspect, plants provided herein are hybrid plants. Hybrids can be produced by preventing self-pollination of female parent plants (e.g., seed parents) of a first variety, permitting pollen from male parent plants of a second variety to fertilize the female parent plants, and allowing F1 hybrid seeds to form on the female plants. Hybrid plants can also be produced by crossing plants from two different species.

An unstable hybrid is characterized by the elimination of one parent's chromosomes during meiosis, resulting in a gamete that retains chromosomes from just one parent. Progeny of a backcross with the desired parent of interest produces a plant where the genome of one parent is substantially not present. A donor species that forms an unstable hybrid with the desired species by transformation is prepared by adding GECs and/or polynucleotides of interest, and/or genomic segments. The desired components are added by transformation or by introgression. The donor species is crossed with the desired recipient species to form an unstable hybrid that comprises the GECs.

EXAMPLES

The following examples provide illustrative embodiments of the instant disclosure. However, those of skill in the art should, in light of the present disclosure, appreciate that many changes can be made in specific aspects of these embodiments without departing from the concept, spirit, and scope of the present disclosure. Moreover, it is apparent that certain agents which are both chemically and physiologically related may be substituted for the agents described herein while the same or similar results would be achieved. All such similar substitutes and modifications apparent to those skilled in the art are deemed to be within the spirit, scope, and concept of the present disclosure as defined by the appended claims.

Example 1. Genome Modification Using a Haploid Inducer Genome as a GEC Carrier Chromosome Modification of a genome of a plant of interest can be carried out via the use of a maternal haploid induction cross to transiently express a genome editing component (GEC) in the proximity of a genome inherited from the plant of interest.

For example, a Cas9/gRNA construct can be transformed into the genome of a plant known for its ability to induce the production of haploid offspring, for example, a maize maternal haploid inducer comprising a high-oil phenotype like CAUHOI (X Dong, X Xu, L Li, C Liu, X Tian, W Li, S Chen (2014) Mol Breeding 34:1147-1158) using any transformation method known in the art (e.g. GA de la Riva, J Gonzalez-Cabrera, R Vasquez-Padron, and C Ayra-Pardo, Elec J of Biotech (1998) 115:12). The gRNA can be designed to target a gene or locus of the genome of a target maize line, for example, a knock-out mutation of the Waxy (Wx) gene sequence (M Shure, S Wessler, N Fedoroff, Cell (1983) 35:225-233) in the genome of corn line B73. The Cas9 can be operably linked to a promoter, e.g maize Ubi-1 (A H Christensen, R A Sharrock, P H Quail, Plant Mol boil (1992) 18:675-689) and the gRNA can be operably linked to a promoter capable of expressing the Cas9 and gRNA in a pollen cell, and/or an egg cell, and/or a zygote cell, and/or an embryo cell before, and/or during, and/or after fertilization (e.g. the rice U6 promoter, PU6.1).

The transformed haploid inducer line comprising the Cas9-gRNA can then be cultivated to produce pollen also comprising the Cas9-gRNA, and this pollen can be used to fertilize a female parent of corn line B73. After pollen from the male haploid inducer parent contacts the female parent, there will be a period of time during which the Cas9-gRNA sequences inherited from the inducer parent will exist in close proximity to the genome inherited from the female parent (e.g. near the time of syngamy), and so shortly before, and/or during, and/or after fertilization of the egg, the Cas9-gRNA will be expressed from the inducer-inherited genome and the products will subsequently be able to modify the nearby genome that was inherited from the female parent, eg. by modifying the Wx gene of B73. In certain embodiments, the genome editing process occurs while the progeny of the induction cross is in the zygote phase of its life cycle. In certain embodiments, the genome editing process requires a longer period of time, potentially spanning several rounds of mitotic divisions in the tissues of the progeny plant.

Following the editing of the B73 genome, the inducer genome and the Cas9-gRNA it contains, will be lost from the cells in a certain frequency of progeny via one of the spontaneous mechanisms of genome elimination that is characteristic of maize maternal haploid inducers, thus yielding a corresponding frequency of haploid progeny plants containing the edited B73 genome. From a plant breeding perspective, it follows that the B73 genome edited by the Cas9-gRNA and inherited by the haploid progeny will be identical to the B73 genome contained in the haploid progeny's female parent, aside from the types of natural and/or spontaneous (e.g. random) mutations that are expected to occur during cell division and/or DNA replication.

Thus, in this example, a certain frequency of haploid progeny plants will be produced comprising B73 genomes that are substantially identical to the original B73 genome of the progeny's female parent, except for the Wx knock-out mutation that was created by the transient, trans-acting Cas9-gRNA (the Cas9-gRNA being eliminated along with the inducer parent's genome sometime during or after fertilization).

Haploid progeny can be identified using any method known in the art (e.g. a visible athocyanin marker like R1-nj). If a high-oil inducer like CAUHOI was utilized, then an automated system can be used to identify and sort haploid progeny seeds from diploid progeny using high-oil seed sorting methods described herein.

Haploid progeny containing specifically the edited B73 genome can be identified using any marker known to be associated with the edit (either positively associated, or otherwise) using a wide range of methods known in the art. In certain embodiments, haploid seeds can be subjected to seed chipping and molecular characterization using the methods described in U.S. patent application Ser. No. 11/213,430, which was filed on Sep. 26, 2005 and published as US20060048247 and issued as U.S. Pat. No. 7,502,113, herein incorporated by reference in its entirety. These and other methods and markers known in the art could be used in conjunction with this invention to screen and/or identify haploid progeny containing the desired edit, including, but not limited to, any method of detecting or determining nucleotide and/or amino acid sequences produced in or by plant cells and/or tissues (e.g. phenotypic screening, DNA sequencing, protein sequencing, DNA mismatch analysis using the Cell, or similar, enzyme, a high resolution melting curve analysis of PCR amplicons containing the target sequence, or other molecular methods, etc.).

The methods described herein are not limited to any activity that might be performed on the haploid progeny following generation of the edit. In certain embodiments, a user may desire to double the chromosomes of a cell in the haploid progeny, in which case, any chromosome doubling method could be used for this purpose. For example, a user may desire to a highly-effective doubling method like those described in U.S. Provisional Patent Application 61/687, 260, filed May 1' 2014 and corresponding PCT Application PCT/US2015/028955, filed on May 1, 2015 and titled Aided Delivery of Plant Treatment Agents, herein incorporated by reference in its entirety. A wide range of alternative methods could also be used to double the cells of haploid progeny generated using methods described herein, including any type of doubling agent and/or doubling technique described in the art.

The methods described herein are not limited to any activities that might be used to affect the frequency and/or efficiency with which haploid progeny are produced. For example, a user may desire to increase the efficiency of haploid induction using the methods described in U.S. Provisional Patent Application 61/987,260 and corresponding PCT Application PCT/US2016/042471, filed Jul. 15, 20116 and titled Methods for Creating Doubled Haploid Plants. Furthermore, any type of inducer could be used as a parent in crosses described herein and/or as a carrier of a GEC. A user of these methods may select inducers for any reason that seems appropriate for various situations, including some threshold of frequency with which a possible inducer's genome is eliminated in progeny cells. In certain embodiments, a user may induce haploidy at various frequencies by performing a wide cross to a related species. It is assumed that using the disclosure herein, one of ordinary skill in the art can now immediately realize that any number of different GECs and gRNAs could be transformed into the genome of a wide range of plants capable of generating haploid embryos in a crop of interest, e.g. transforming a *Tripsacum* plant with a Cas9 and a gRNA encoding a mutational knock-out of the maize Wx gene, and then using that plant as a parent in a cross with B73 to produce haploid offspring comprising a B73 genome containing a Wx gene knock-out edit (e.g. by incorporating methods described by RV Sairam, C Wilber, J Franklin. et al. (2002) In Vitro Cell Dev Biol-Plant 38: 435).

Nor are the methods herein limited in any way to certain GEC or gRNA types or sequences. Any GEC or gRNA capable of being encoded by nucleotide sequences could be used in conjunction with the methods described herein, including transgenes, native genes, or any other process that alters the nucleotide sequences (i.e. mutations). Based on this disclosure, one of ordinary skill in the art of plant molecular biology can use even relatively complicated systems in conjunction with this invention, for example, transforming a haploid inducer with a viral replicon precursor comprising a GEC, which in turn comprises a replicase gene operably-linked to appropriate promoters and flanked by LIR geminivirus sequences, then using that plant to pollinate a B73 plant, and then recovering haploid progeny comprising a B73 genome that contains a desired edit encoded by the GEC.

Furthermore, it is anticipated that plant breeders of ordinary skill will immediately recognize that even very large sections of DNA, e.g. QTLs, megaloci, chromosome intervals spanning several (dozen) centimorgans, and even substantial sections of a chromosome arm can be translocated into and/or out of a target genome using the methods described herein. In certain embodiments, methods and compositions described in U.S. Provisional Patent Application 61/787,894, filed Mar. 15, 2013 and/or corresponding U.S. patent application Ser. No. 14/209,731, titled Creation and Transmission of Megaloci and filed Mar. 13, 2014, can be used. In certain examples, the edit created in the target genome comprises a transgenic nucleotide sequence operably-linked to a promoter that can be used to drive and/or control expression of the transgene, for example, a CaMV 35S promoter operably-linked to the insecticidal protein Cry 1 Ab.

Alternatively, a haploid inducer line carrying a GEC and a recipient line carrying the target edit can both be doubled to create tetraploid plants. The tetraploid inducer line can then be crossed with the tetraploid recipient line to create dihaploid progenies carrying the desired edit. The inducer genome and the GEC are both eliminated during the tetraploid crossing process. Therefore, the method does not require any further doubling after genome editing occurs.

Example 2. Modifying a Plant Genome Using a Supernumerary Chromosome as a GEC Carrier Chromosome A genome edit can be created in a target plant genome by crossing a plant to a haploid inducer line comprising a supernumerary chromosome, e.g. a B chromosome, containing an expression cassette encoding a GEC, such as the Cas9 and associated gRNA system.

Analogous to the transient expression of a GEC from the inducer genome shortly before, and/or during, and/or after fertilization described Example 1, cells of a haploid inducer in this example contain a supernumerary chromosome, e.g. a B chromosome, that comprises a gRNA designed to target a gene or locus of a target maize line, for example, the Wx gene in a target B73 genome. The Cas9 can be operably linked to a promoter, e.g maize Ubi-1 and the gRNA can be operably linked to a promoter capable of expressing the Cas9 and gRNA in a pollen cell, and/or an egg cell, and/or a zygote cell, and/or an embryonic cell shortly before, and/or during, and/or after fertilization (e.g. the rice U6 promoter, PU6.1).

Pollen of the haploid inducer comprising this B chromosome can then be used to fertilize a female parent of corn line B73. After pollen from the male haploid inducer parent contacts the female parent, there will be a period of time during which the Cas9-gRNA sequences carried by the B chromosome and inherited from the inducer parent will exist in close proximity to the genome inherited from the female parent (e.g. near the time of syngamy), and so shortly before, and/or during, and/or after fertilization of the egg, the Cas9-gRNA will be expressed from the inducer-inherited B chromosome and the products will subsequently be able to modify the nearby A genome that was inherited from the female parent, eg. by modifying the Wx gene of B73. In certain embodiments, the genome editing process occurs while the progeny of the induction cross is in the zygote phase of its life cycle.

Because B chromosomes can undergo non-disjunction when crossed as a male, progeny resulting from a male parent with one B chromosome can comprise zero, one, two, or more B chromosomes when crossed with a female plant containing zero B chromosomes even after the A genome of the inducer parent has been eliminated in the progeny. So, in certain embodiments, the supernumerary chromosome persists in the cells of the progeny beyond the zygote phase, e.g. for several rounds of mitotic divisions, providing an extended window for the genome editing process to take place before the supernumerary chromosome is eliminated in the progeny. Progeny that contain at least one B chromosome inherited from the inducer parent can be identified and isolated using any method desired by the user, e.g. nucleotide sequencing, molecular marker detection, etc.

In certain embodiments, it may be desired and/or necessary to "breed out" the supernumerary chromosome contained in the progeny plants after the edit is made, e.g. by outcrossing or selfing the progeny plants and analyzing and selecting (e.g. by molecular marker(s) and/or nucleotide and/or amino acid sequence analysis, and/or some other method) those progenies that have lost the supernumerary chromosome.

In certain embodiments, following the editing of the B73 genome, the B chromosome, and the Cas9-gRNA it contains, may be eliminated from the cells of a certain frequency of progeny via one of the spontaneous mechanisms of elimination that is characteristic of maize supernumerary chromosome elimination, thus yielding a corresponding frequency of haploid progeny plants containing the edited B73 genome.

From a plant breeding perspective, it follows that the B73 genome edited by the Cas9-gRNA and inherited by the haploid progeny will be identical to the B73 genome contained in the haploid progeny's female parent, aside from the types of natural and/or spontaneous (e.g. random) mutations that are expected to occur during cell division and/or DNA replication.

As described in Example 1 and elsewhere herein, these methods are not limited to any manner of additional activities can be can be conducted before, during, or after the edit is made. Depending on the objectives of the user, for example, chromosome doubling, and/or genotypic and/or phenotypic analysis and screening, and/or steps to improve haploid induction, and/or selfing to confirm doubling, etc. can also be performed, e.g. similar to those described in Example 1 herein. One of ordinary skill in the art of plant genetics will immediately appreciate the applications of a haploid plant containing an elite genome comprising a certain, specific edit, for example, a B73 genome with a knock-out mutation in the Wx locus.

Nor are the methods described herein limited in any way to the process by which a supernumerary chromosome containing a GEC is derived. A wide range of possible options for creating supernumerary chromosomes comprising desired sequences have been described. For example, it is anticipated that one can cross a first parent plant containing a B chromosome to a second parent plant that encodes a recombinase and/or a nuclease operably-linked to a promoter that is capable of incorporating a specific sequence in the A genome into the B chromosome in the progeny. Other examples include irradiating pollen containing a B chromosome to generate one or more spontaneous (e.g. random) breaks in the B chromosome and/or A chromosomes, which can, at some frequency, recombine to form a new B chromosome containing a GEC and a desired template DNA sequence. Still other examples include using a B-A translocation mechanism, e.g. a GEC positioned on the short arm of chromosome 9 of the A genome which is capable of translocating a DNA sequence from the A genome into the B chromosome. One of skill in the art will immediately appreciate that these and other methods for creating supernumerary (e.g. B) chromosomes with desired sequences can be used in conjunction with this invention.

Example 3. Haploid Induction Coupled with Delivery of Exogenous Nucleic Acids to a Recipient Line Transgenic traits can be delivered to a plant of interest via the use of a haploid induction cross. A nucleic acid sequence encoding transgene of interest ("donor transgene") and a site-specific enzyme are introduced to a HI corn plant via standard breeding or plant transformation techniques. The site-specific enzyme is operably linked to a promoter capable of expressing the GEC in a pollen cell, an egg cell, and/or a zygote before, during, or after fertilization.

The HI corn plant comprising the donor transgene and GEC is crossed as a male to a second corn plant, and the GEC is transiently expressed shortly before, during, or after fertilization. The GEC translocates the donor transgene from the HI corn plant's genome into a targeted location within a maternal genome of the egg cell before the paternal nuclear genome is lost.

Induced haploid seed comprising are identified as described in Example 1. Receipt of the donor transgene in the induced haploid seed is confirmed via PCR, ELISA, or other molecular methods known to those skilled in the art. Following confirmation of donor transgene integration and haploid induction, the haploid seed can be subjected to chromosome doubling using any method known in the art, if desired.

Example 4. Modifying a Plant Genome Using a Chloroplast Genome as a GEC Carrier Chromosome A corn chloroplast genome is transformed to comprise a Wx-targeting gRNA and Cas 9 operably linked to a promoter capable of expressing the GEC in an egg cell, and/or a zygote before, during, or after fertilization according to standard molecular biology techniques. A transfer peptide may be operably linked to Cas9 to allow it to be transferred from the chloroplast to the nucleus. An example of such a peptide is a portion of the whirly protein (Isemer R, Mulisch M, Schafer S K, Koop H U, Krupinska K. (2012) FEBS Letters 58:85-55). Corn plants comprising successfully transformed chloroplasts are identified using standard molecular biology techniques (e.g., sequence analysis, PCR) or phenotypic screening. Corn plants comprising transformed chloroplast genomes are bred into an indeterminate gametophyte1 (ig1) background by crossing the corn line comprising a transformed chloroplast genome as a female and an ig1 corn plant as a male, followed by self-pollination or further backcrosses to ig1 plants (using ig1 as the male parent) in order to obtain a plant that is homozygous for ig1 that also comprises the transformed chloroplast. Corn plants homozygous for the ig1 mutation are capable of generating paternal haploids after fertilization by eliminating the maternal nuclear genome.

An ig1 plant comprising the chloroplast genome transformed with a Wx-targeting gRNA and Cas 9 GEC is crossed as a female to a corn plant of a recipient line, e.g. B73. The maternal nuclear genome is lost after fertilization, thus producing haploid progeny comprising a the B73 nuclear genome and the transformed chloroplast genome. The Wx-targeting gRNA and Cas 9 is expressed from the chloroplast genome after fertilization and throughout development of the subsequent haploid or dihaploid plant, which results in modification of the B73 nuclear genome. Resultant haploid progeny carrying the desired modification in their paternally-derived B73 genome can be identified as described in Example 1 and elsewhere herein and in the art.

In certain embodiments, the Wx-targeting gRNA and Cas9 components can be "bred out" of the progeny by crossing them with a plant comprising a second ig1 mutation but lacking the gRNA and/or Cas9 sequences and recovering offspring that contain the Wx modification but not the gRNA and/or Cas9 sequences. Alternatively, the Wx-targeting gRNA and Cas9 components can be "bred out" of the B73 progeny comprising the Wx modification by crossing them as males to B73 or other lines and recovering offspring that contain the Wx modification. Because chloroplast are not efficiently transferred via pollen, offspring that lack the gRNA and/or Cas9 sequences are recovered.

Example 5. Native Genes as Templates to Direct DNA Repair

Native gene variants (alleles) can be used to guide the modification of the corresponding gene in a desired line. A native allele is excised from a nuclear genome using a nuclease, and then the excised DNA is repaired via homologous recombination using the native allele from a HI line as repair template.

TALENs are designed to excise the defective transparent testa glabra1 (ttg1-1) allele from *Arabidopsis thaliana*, with one TALEN designed to bind at the site of the mutation present in the ttg1-1 allele. Such a design allows the TALEN to bind and excise the ttg1-1 allele, but not the functional wildtype TTG1 allele. Expression of TTG1 provides pigmentation to Arabidopsis seeds.

A transformation construct is generated where nucleic acid sequences encoding the pair of TALENs are operably linked to a modified version of the egg/zygote-specific promoter EC1.2en_EC1.1p. The transformation construct further comprises a nucleic acid sequence encoding a green fluorescent protein (GFP) and a selectable marker to provide herbicide tolerance. The transformation construct is transformed into an Arabidopsis plant heterozygous for a null allele for the CENH3 gene (encoding the centromere-specific histone CENH3 protein), homozygous for the GFP-tailswap-CenH3 transgene (see Ravi and Chan. 2010. Nature. 464:615-619), and homozygous for the wildtype TTG1 allele.

Resulting progeny are screened using an herbicide; transformants comprising the transformation construct are resistant to the herbicide. Herbicide-tolerant transformants are then genotyped to identify transgenic events that are heterozygous for the CENH3 null allele. Plants comprising the transformation construct and that are heterozygous for the CENH3 null allele are self-pollinated.

Resulting progeny are selected for haploid induction individuals that are homozygous for the CENH3 null allele and homozygous for the transformation construct. Selected individuals are grown and crossed as females to male ttg1-1 mutant lines. The resulting seed are screened for individuals that lack GFP expression, but have wildtype TTG1 pigmentation in the seed. Such plants are grown and examined using standard molecular biology techniques (e.g., sequence analysis, PCR, DART) to confirm that the ttg1-1 allele has been converted to the wildtype TTG1 allele.

Example 6. Extending the Period of Time During which Genome Editing Elements can Function to Create Edits in a Target Genome It is envisioned that any method in the art known for altering cell growth, cell division, and/or cell development in a plant could be used in conjunction with the methods disclosed herein. In certain embodiments, a user can use any method known to slow, delay, and/or halt cell division in a plant to prolong the period of time during which a carrier molecule containing a GEC remains close enough to a target genome that the products of the GEC can complete a desired edit. These methods include the use of various PGRs (e.g. cytokinins) and other chemical treatments, as well as altering other aspects of a plant's growing environment. For example, by reducing the temperature under which an embryo is cultivated, one can reduce the rate of cell division. Thus, it is anticipated that one can use a maize haploid inducer line transformed to comprise a GEC comprising a Wx knockout mutation operably-linked to a promoter (e.g. Ubi-1) in its genome, e.g. as described in Example 1, to pollinate a plant containing a genome in which a user desires to create an edit, e.g. B73. Following pollination by the inducer, the haploid embryo and/or zygote are cultivated in a reduced temperature, thereby reducing the likelihood that the inducer genome and the GEC it contains are lost before the GEC is able to create the desired edit.

These methods are not limited to specific types of regulatory sequences and any nucleotide sequence known to regulate the expression of plant genome could be used in conjunction with these methods, including any post transcription or post translation regulation and/or silencing sequence and/or mechanism known in the art. One aspect of these method is that the regulation encoded by these type of sequences would not necessarily create a genetic change in the target genome, permitting recovery of offspring that contain genomes substantially identical to one parent, aside from the edit encoded by the GEC, without successive backcrossing.

In certain embodiments, plants carrying transgenic sequences that slow cell division can be used, e.g. a transgenic plant carrying a mutation in the CDKA; 1 (Morgan D O (1997) Annu Rev Cell Dev Biol 13:261-291; E Wijnker, A Schnittger (2013) Plant Reprod 26:143-158) gene could be used. This mutation could be encoded by either a female or a male plant used in a cross, for example, in a maternal haploid induction cross. This transgenic control can be encoded by cells of the female parent near progeny cells, and/or encoded by the pollen of the male parent, and/or by the progeny zygote and/or embryo. This transgenic control can slow, delay, and or halt cell division in the progeny plant, thereby extending the window during which the inducer genome carrying a GEC remains close enough to the target genome for the expressed GEC products to create a desired edit.

In certain embodiments, a carrier chromosome is created that contains sequences other than, and/or in addition to, GEC sequences, and this carrier chromosome is used to not only to create edits in a target genome, but also to regulate the expression of certain genes in a target genome.

For example, a maize haploid inducer line can be transformed to comprise a GEC comprising a Wx knockout mutation operably-linked to a promoter (e.g. Ubi-1) in its genome, e.g. as described in Example 1. This inducer is also transformed to contain DNA sequences that can slow/disrupt cell division and/or the cell cycle of a plant zygote and/or embryo cell, for example, a cyclin-dependent kinase sequence such as CDKA; 1. A user may then use this transformed haploid inducer as a male parent in a cross with a female parent containing a genome that the user wishes to edit, e.g. B73. After pollen from the male haploid inducer parent contacts the female parent, there will be a period of time during which the cell cycle regulation sequences inherited from the inducer parent will exist in close proximity to the genome inherited from the female parent (e.g. near the time of syngamy), and so shortly before, and/or during, and/or after fertilization of the egg, both the genes of the GEC and the cell cycle genes will be expressed from the inducer-inherited genome and the products will subsequently be able to modify expression of the nearby genome that was inherited from the female parent, eg. by creating a knockout mutation in the Wx gene of a B73 genome comprising a CDKA: 1 mutation.

An advantage of this example is that the cell cycle of the zygote and/or embryo can be slowed, delaying the elimination of the inducer genome and the GEC it contains, thereby extending the window during which the GEC on the carrier chromosome remains in proximity to the target genome. In certain examples, cell division in the progeny zygote can be arrested for many hours or even days, providing a much longer time for the GEC editing components to perform their function of creating a desired edit.

Clearly, these methods are not limited to specific sequences encoded in a carrier chromosome or to certain mechanisms of regulation. Although this example highlights the utility of using certain elements that ultimately delay the elimination of GEC sequences in cells, methods in the art describe how one of ordinary skill can transform the genome of an inducer plant with any manner of DNA sequences. Any gene known to affect the growth, development, or performance of a plant could be transformed into an inducer plant, whether stably-integrated into the inducer plant's nuclear genome, stably-integrated in a supernumerary chromosome, and or transiently integrated in the inducer plant cells.

Furthermore, these aspects are not limited to the type of carrier chromosome containing the DNA sequences capable of trans-regulating expression in a target genome. Any molecule containing a GEC could also contain a regulatory element designed to function in the zygote and/or embryo and/or seedling of a plant could be used in conjunction with this invention. However, the regulatory DNA sequences are not required to be on the same carrier chromosome, as it is envisioned that a plant cell containing a GEC on one carrier molecule (e.g. a haploid inducer's nuclear A genome) and containing additional regulatory elements on a different carrier molecule (e.g. a B chromosome), or vice versa, could be used to accomplish similar objectives without falling outside of the scope of the methods described herein.

Furthermore, the regulatory elements need not be provided by the same parent as the GEC. In certain examples, a plant containing the genome the user wants to edit is transformed to contain the regulatory elements. For example, B73 plant can be transformed with a cyclin-dependent kinase sequence, such as CDKA; 1 operably-linked to a zygote- or embryo-specific promoter, for example, an embryo-specific promoter from the 5' regulatory region of an emb5 gene, as described in U.S. Pat. No. 7,078,234, titled "Maize embryo-specific promoter compositions and methods for use thereof", granted Jul. 18, 2006, and corresponding U.S. patent application Ser. No. 10/732,721, filed Dec. 10, 2003, and published as US Patent Application No. US20040163144 under the same title. This plant can then be pollinated by a haploid inducer line transformed with a GEC, e.g. one comprising a Wx knockout mutation operably-linked to a promoter (e.g. Ubi-1) in its genome as described in Example 1. There will be a period of time after pollen from the male haploid inducer parent contacts the female parent during which the GEC sequences inherited from the inducer parent will be expressed in close proximity to the genome inherited from the female parent at or about the same time that CDKA-1 is expressed from the genome inherited from the female parent. Thus, the cell-cycle gene in the genome inherited from the female parent will function to slow or halt cell division in the zygote and/or embryo, thereby also delaying the chromosome elimination mechanisms that might otherwise cause the carrier chromosome containing the GEC to be lost before the GEC components have had sufficient time to complete the desired edit in the B73 genome.

In certain embodiments, the genome editing process occurs while the progeny of the induction cross is in the zygote phase of their life cycle. In certain embodiments, the genome editing process requires a longer period of time, potentially spanning several rounds of mitotic divisions in the tissues of the progeny plant.

Example 7. Successful Genome Editing Via Haploid Induction

Embryogenic callus was produced from seedling-derived explants of the proprietary high oil, redroot haploid inducer line and used for *Agrobacterium*-mediated transformation essentially as described by Sidorov et al. (2006). Briefly, 125 mature seed were surface-sterilized for 20 minutes in a 50% Clorox® solution containing a few drops of Tween®20 as a surfactant. The container was vacuum infiltrated briefly several times during the Clorox® treatment to help remove trapped air from the seed. Following 5 rinses in sterile water, seed was plated onto either MS3 or MSVS34 medium (Sidorov et al., 2006) at 6 seed per 100×25 mm Petri plate, placed into clear plastic sweater boxes, and incubated at 28° C., with a light intensity of 100 μmol $m^{-2}$ $sec^{-1}$ provided by cool white fluorescent bulbs, and a 16:8 photoperiod.

After 7 days on the germination medium, nodal sections were prepared and plated cut-surface down onto MSW57 or CM4C medium (Sidorov et al., 2006). These plates were returned to clear plastic sweater boxes and incubated at 28° C., 100 μmol $m^2$ $sec^{-1}$, 16:8 photoperiod as for germination. 25 days later, cultures were examined under a dissecting microscope and any regions showing signs of embryogenic callus development were subcultured to fresh medium of the same composition, and then returned to the sweater boxes and incubated in the dark at 28° C. Four additional subcultures were performed at 2 week intervals, selecting for high quality embryogenic callus, to proliferate a large quantity for transformation. Embryogenic callus was used for transformation 7 days after the final subculture.

*Agrobacterium* strain ABI derived from C58 (Koncz and Schell, 1986) harboring the binary vector Construct-630 was used for transformation. Construct-630 contains a neomycin phosphotransferase II gene (nptII; Bevan et al., 1983) driven by the cauliflower mosaic virus 35S promoter (Odell et al., 1985) as a plant selectable marker, and the Cre recombinase gene (Zhang et al., 2003) driven by the rice actin promoter (McElroy et al., 1990). The ABI::Construct-630 *Agrobacterium* strain was grown in LB medium (Sambrook et al., 1989), induced in modified AB minimal medium (Zhang et al., 2003) with 200 μM acetosyringone, and resuspended in inoculation medium (Sidorov et al., 2006, but to a final $OD_{660}$ of 0.5 instead of 1.0). Immediately prior to use, 1 μl of a 10% Pluronic® acid solution was added per 1 ml of *Agrobacterium.*

2.77 grams of embryogenic callus was placed into a 50 ml centrifuge tube, followed by addition of 12 mls of *Agrobacterium* inoculum. The tube was inverted several times to mix thoroughly mix, and then centrifuged at 1270 rpms for 30 min. The *Agrobacterium* solution was poured off, and the tissue dumped onto sterile filter papers and blotted to remove excess *Agrobacterium*. Tissue was then placed onto two sterile Whatman #1 filter papers in a 100×25 mm petri dish, sealed with parafilm, and incubated at 23° C. in the dark. Following a 4-day co-culture period during which the tissue becomes partly desiccated (Cheng et al., 2003), the tissue was divided into smaller pieces of 2-3 mm in diameter following natural breakage points, and transferred onto selection medium. For this purpose, the tissue was split evenly across four individual 9 cm diameter sterile Whatman #1 filters, which were each placed on top of two sterile 2 cm×2 cm squares of acrylic white felt saturated with liquid selection medium (MSW57 per Sidorov et al, 2006, but with 500 mg $L^{-1}$ carbenicillin to control *Agrobacterium* growth and 100 mg $L^{-1}$ paromomycin for plant selection). Plates were incubated (unsealed) in plastic sweater boxes in the dark at 28° C. Two weeks later, medium was aspirated from the felts using a pipet, and 15 mls of fresh liquid selection medium added. Fresh selection medium was again added one week later to keep the felts saturated but without excess liquid pooling on the tissue. Nine days later, the tissue was moved to regeneration medium as described in Sidorov et al. 2006 (MS=Murashige and Skoog, 1962, basal plus 3.5 mg $L^{-1}$ 6-benzylaminopurine plus 250 mg $L^{-1}$ carbenicillin). Six days later, the tissue was moved to hormone-free MS medium with 250 mg $L^{-1}$ carbenicillin and 100 mg $L^{-1}$ paromomycin. Small shoots developing on this medium were transferred to fresh hormone-free MS medium in Phytatrays™ for continued shoot growth and root development. Rooted shoots were moved to propagation plugs (International Horticultural Technologies, Hollister CA, USA) and transferred to a growth chamber.

A total of seven plants were recovered. All originated from the same paromomycin-resistant callus sector and were presumed to be clonal. Of these 7 plants, 4 survived transfer to propagation plugs. Leaf samples were taken for DNA extraction, and analyzed for copy number of the Cre and nptII genes, and the left border sequence region of the T-DNA, by real-time Taqman. All four plants contained 1-2 copies of each tested region. Presence or absence of the OriV sequence in the vector backbone was tested by PCR, and all four plants lacked this sequence. Three of the four plants were successfully self-pollinated, and were also testcrossed as males onto female plants homozygous for a single-copy transgenic insert from the Construct-133. Construct-133 contains a GFP gene (Pang et al., 1996) controlled by the 35S promoter (Kay et al., 1987) and nopaline synthase (nos) polyadenylation region (Fraley et al., 1983). It also contains a maize hsp70 intron in the 5' untranslated region (Brown and Santino, 1995). An nptII gene flanked by loxP sites is inserted within the hsp70 intron sequence. In the absence of Cre protein, the nptII gene remains stably inserted and serves as a plant selectable marker. There is a transcription termination signal as part of the nptII cassette, which prevents transcription of GFP. Upon exposure to active Cre protein, the loxP sites recombine and the nptII-coding sequence and terminator are excised, allowing transcription of GFP.

A total of 284 testcross progeny seeds were generated and planted, and 47 did not germinate. 29 polymorphic markers that spread across maize genome and are informative between the inducer genome and the tester lines were selected to confirm ploidy by endpoint TaqMan PCR assay (Table 1). Haploid seeds were homozygous and diploid seeds were heterozygous for these polymorphic markers. Of the 237 testcross progenies that germinated and produced plants, 233 testcross progenies are diploids. Among the 233 diploids, there was perfect correlation between presence of Cre and GFP expression. 4 out of the 237 testcross progenies were confirmed to be haploid and absent of inducer genome.

In Table 1, "IcM" refers to the map units of the IBM2 2008 Neighbors Genetic Map, which was generated with an intermated recombinant inbred population (syn 4) that resulted in approximately a four-fold increase in the number of meiosies as compared to the typical recombination experiment that is used to generate cM distances (Lee et al., 2002, Plant Mol Biol 48:453 and the Maize Genetics and Genomics Database). "cM" refers to the classical definition of a centimorgan wherein one cM is equal to a 1% chance that a trait at one genetic locus will be separated from a trait at another locus due to crossing over in a single generation (meaning the traits co-segregate 99% of the time during meiosis), and this definition is used herein to delineate map locations pertaining to this invention.

TABLE 1

Primers and probes of 29 polymorphic markers for detection of ploidy
cM = centimorgans, IcM = map units of the IBM2 2008 Neighbors Genetic Map.

| | | | | | | SEQ ID NO. | | | |
|---|---|---|---|---|---|---|---|---|---|
| SEQ ID NO. | Chromosome | MON v5.2 map (cM) | IBM2008 Map (IcM) | SNP Position | Polymorphism | Fwd Primer | Rev Primer | Probe 1 | Probe 2 |
| 1 | 1 | 7.5 | 20.2 | 399 | [A/C] | 30 | 59 | 88 | 117 |
| 2 | 1 | 64.1 | 184.3 | 96 | [A/T] | 31 | 60 | 89 | 118 |
| 3 | 1 | 121.2 | 458.2 | 132 | [C/G] | 32 | 61 | 90 | 119 |
| 4 | 1 | 197.7 | 780.9 | 93 | [C/T] | 33 | 62 | 91 | 120 |
| 5 | 2 | 27 | 57.6 | 501 | [A/C] | 34 | 63 | 92 | 121 |
| 6 | 2 | 140.5 | 468 | 477 | [C/T] | 35 | 64 | 93 | 122 |
| 7 | 2 | 206.8 | 693.1 | 278 | [G/T] | 36 | 65 | 94 | 123 |
| 8 | 3 | 92.2 | 315.8 | 59 | [G/T] | 37 | 66 | 95 | 124 |
| 9 | 3 | 206.6 | 792.3 | 248 | [A/G] | 38 | 67 | 96 | 125 |
| 10 | 4 | 64.9 | 154.8 | 124 | [C/G] | 39 | 68 | 97 | 126 |
| 11 | 4 | 89.3 | 279.9 | 432 | [A/C] | 40 | 69 | 98 | 127 |
| 12 | 4 | 163 | 573.9 | 234 | [A/G] | 41 | 70 | 99 | 128 |
| 13 | 4 | 185.7 | 656.5 | 81 | [C/T] | 42 | 71 | 100 | 129 |
| 14 | 5 | 42.2 | 163.6 | 299 | [A/G] | 43 | 72 | 101 | 130 |
| 15 | 5 | 66 | 222.5 | 247 | [A/G] | 44 | 73 | 102 | 131 |
| 16 | 5 | 109.3 | 376.5 | 571 | [A/G] | 45 | 74 | 103 | 132 |
| 17 | 6 | 34.5 | 189.7 | 286 | [C/G] | 46 | 75 | 104 | 133 |
| 18 | 6 | 68.3 | 318.7 | 209 | [C/G] | 47 | 76 | 105 | 134 |
| 19 | 6 | 136.7 | 544.4 | 187 | [A/T] | 48 | 77 | 106 | 135 |

TABLE 1-continued

Primers and probes of 29 polymorphic markers for detection of ploidy
cM = centimorgans, IcM = map units of the IBM2 2008 Neighbors Genetic Map.

| | | | | | | SEQ ID NO. | | | |
|---|---|---|---|---|---|---|---|---|---|
| SEQ ID NO. | Chromosome | MON v5.2 map (cM) | IBM2008 Map (IcM) | SNP Position | Polymorphism | Fwd Primer | Rev Primer | Probe 1 | Probe 2 |
| 20 | 7 | 66.4 | 209.6 | 133 | [A/C] | 49 | 78 | 107 | 136 |
| 21 | 7 | 132.2 | 469.1 | 92 | [G/T] | 50 | 79 | 108 | 137 |
| 22 | 7 | 146.4 | 513.1 | 488 | [A/C] | 51 | 80 | 109 | 138 |
| 23 | 8 | 102.5 | 361.9 | 287 | [A/G] | 52 | 81 | 110 | 139 |
| 24 | 8 | 144.9 | 478.5 | 470 | [A/G] | 53 | 82 | 111 | 140 |
| 25 | 9 | 62.7 | 195.7 | 305 | [A/G] | 54 | 83 | 112 | 141 |
| 26 | 9 | 74.7 | 263.6 | 309 | [C/T] | 55 | 84 | 113 | 142 |
| 27 | 9 | 144.9 | 581.4 | 166 | [C/G] | 56 | 85 | 114 | 143 |
| 28 | 10 | 114 | 472.4 | 223 | [A/T] | 57 | 86 | 115 | 144 |
| 29 | 10 | 134.3 | 525.1 | 256 | [A/G] | 58 | 87 | 116 | 145 |

Further molecular analysis was designed to amplify a DNA segment across the excision junction to confirm that NPTII was excised. DNA from the roots and/or tissue were extracted using DNeasy Plant Min Kit (Qiagen) and quantified using Picogreen dsDNA Assay Kit (Thermo Fisher) following manufacturer's instructions. Two PCR primer sets were designed internally to amplify a 551 bp and 801 bp fragment in excided tissue (Table 2). In contrary, if excision did not occur, the expected fragments were 1758 bp and 2108 bp. Approximately 1-10 ng of template DNA was added to a 50 ul reaction using DreamTaq Green mix (Thermo Fisher). Cycling conditions were 95 C for 2 min, and 30 cycles of 95 C (30 s), 57 C (30 s) and 72 C (2 min), followed by a final extension at 72 C for 7 min. Sterile distilled water was used as a negative control. PCR products were analyzed in a 1% agarose gel electrophoresis stained with GelGreen (Biotium). Hi-lo DNA marker (Bionexus) was used as a reference. All reactions were performed using the GeneAmp 9700 thermocycler (Applied Biosystems/Thermo Fisher). Out of 4 haploid plants, the root tissue from 1 haploid plant was confirmed with GFP expression and excision of NPTII cassette. Primers and probes were also designed to detect the presence or absence of Cre by endpoint TaqMan PCR assay (Table 3). The same haploid plant was confirmed to be absent of Cre. In summary, the experiment demonstrated successful genome editing (excision of NPTII), and the elimination of GEC (Cre) and inducer genome in the haploid progeny.

TABLE 2

| Primers for detection of NPTII cassette |
|---|
| Forward Primer:<br>5'-CCC GTT CAC ATC ACC ATC CA-3' |

TABLE 2-continued

| Primers for detection of NPTII cassette |
|---|
| Reverse Primer:<br>5'-GAA CCT ACA CAG CAA TAC GAG AAA-3' |

TABLE 3

| Primers and probes for detection of Cre |
|---|
| Forward Primer:<br>5'-CAAGTGACAGCAATGCTGTTTCA-3' |
| Reverse Primer:<br>5'-GTCGAAATCAGTGCGTTCGAA-3' |
| Probe:<br>5'-CGGTGAACGTGCAAAA-3' |

The same experiment was repeated with homozygous R1 progenies to increase sample size and to extend the initial experiment to demonstrate genome editing in the germline tissue. In this experiment, 5 out of 396 haploid plants were observed with GFP expression in the root and the leaf. Among these 5 haploid plants, 2 plants were also observed with GFP expression in the shoot (germline tissue). Additional cytological and molecular analysis is in progress to confirm that the target region is edited, and GEC and inducer genome are eliminated.

What is claimed is:

1. A method of editing maize genomic DNA, comprising:

a) introducing at least one Genome Editing Component (GEC) into a chloroplast genome of a maize haploid inducer line that comprises an ig1 haploid inducer to produce a first maize plant that comprises the at least one GEC and the ig1 haploid inducer, wherein the at least one GEC comprises at least one recombinase or at least one endonuclease operably linked to a transfer peptide that transfers the at least one recombinase or the at least one endonuclease from the chloroplast to the nucleus, wherein the transfer peptide comprises a Whirly protein or a portion thereof;

b) providing a second maize plant, wherein the second maize plant comprises the maize plant genomic DNA which is to be edited;

c) crossing the second maize plant with the first maize plant; and d) selecting at least one haploid progeny produced by the cross of step (c) wherein the haploid progeny comprises the genome of the second maize plant but lacks the genome of the first maize plant, and wherein the genome of the haploid progeny comprises at least one targeted genome modification.

2. The method of claim 1, wherein the at least one GEC comprises at least one recombinase.

3. The method of claim 1, wherein the at least one endonuclease is selected from the group consisting of a CRISPR associated nuclease, a transcription activator-like effector nuclease (TALEN), a TALE-like protein, a zinc finger nuclease, and a meganuclease.

4. The method of claim 2, wherein the at least one recombinase is selected from the group consisting of a tyrosine recombinase attached to a DNA recognition motif and a serine recombinase attached to a DNA recognition motif.

5. The method of claim 4, wherein the tyrosine recombinase attached to a DNA recognition motif is selected from the group consisting of a Cre recombinase, a Gin recombinase, a FLP recombinase, and a Tnp1 recombinase.

6. The method of claim 4, wherein the serine recombinase attached to a DNA recognition motif is selected from the group consisting of a Bxb1 integrase, a phiC31 integrase, an R4 integrase, and a TP-901 integrase.

7. The method of claim 1, wherein the edited haploid progeny is treated with a chromosome doubling agent, thereby creating an edited doubled haploid progeny.

8. The method of claim 7, wherein the chromosome doubling agent is colchicine, pronamide, and trifluralin.

9. The method of claim 1, wherein the first maize plant expresses a marker gene.

10. The method of claim 9, wherein the marker gene is selected from the group consisting of GFP and anthocyanin pigments.

11. The method of claim 1, wherein the maize haploid inducer line comprises a knock-out mutation in a patatin-like phospholipase gene.

12. The method of claim 1, wherein the haploid inducer line further comprises a high-oil or redroot trait.

13. The method of claim 1, wherein the endonuclease is Cpf1.

14. The method of claim 1, wherein the GEC is introduced into the chloroplast genome of the maize haploid inducer line by crossing a maize plant that comprises the ig1 haploid inducer with a maize plant that comprises the GEC in the chloroplast genome.

15. The method of claim 14, wherein the haploid progeny comprises the maternal mitochondrial and plastid genomes.

* * * * *